United States Patent
Bennett-Guerrero

(10) Patent No.: US 9,028,407 B1
(45) Date of Patent: May 12, 2015

(54) METHODS AND APPARATUS FOR MONITORING PATIENT CONDITIONS

(71) Applicant: Safer Care LLC, Chapel Hll, NC (US)

(72) Inventor: Elliott Bennett-Guerrero, Chapel Hill, NC (US)

(73) Assignee: Safer Care LLC, Chapel Hill, NC (US)

( * ) Notice: Subject to any disclaimer, the term of this patent is extended or adjusted under 35 U.S.C. 154(b) by 0 days.

(21) Appl. No.: 14/105,552

(22) Filed: Dec. 13, 2013

(51) Int. Cl.
| | |
|---|---|
| *A61B 5/00* | (2006.01) |
| *A61B 5/11* | (2006.01) |
| *A61B 5/0205* | (2006.01) |
| *A61B 5/107* | (2006.01) |
| *G01B 3/56* | (2006.01) |
| *G01B 3/00* | (2006.01) |
| *A61B 5/024* | (2006.01) |

(52) U.S. Cl.
CPC ............. *A61B 5/1121* (2013.01); *A61B 5/0205* (2013.01); *A61B 5/024* (2013.01); *A61B 5/1116* (2013.01); *A61B 5/4094* (2013.01); *A61B 5/42* (2013.01); *A61B 5/4809* (2013.01); *A61B 5/6823* (2013.01); *A61B 5/743* (2013.01); *A61B 5/746* (2013.01); *A61B 5/683* (2013.01); *A61B 5/1071* (2013.01); *A61B 5/0002* (2013.01); *G01B 3/56* (2013.01); *A61B 5/6813* (2013.01); *A61B 2562/24* (2013.01); *Y10S 224/929* (2013.01); *Y10S 224/93* (2013.01)

(58) Field of Classification Search
CPC .. A61B 5/1071; A61B 5/6813; A61B 5/6823; A61B 5/683; A61B 5/6835; A61B 5/1116; A61B 2505/03; A61B 2562/24; A61B 2562/247; G01B 3/56
See application file for complete search history.

(56) References Cited

U.S. PATENT DOCUMENTS

| | | | |
|---|---|---|---|
| 4,348,562 A | 9/1982 | Florin | |
| 5,914,660 A | 6/1999 | Mesibov et al. | |
| 5,941,836 A | 8/1999 | Friedman | |
| 6,049,730 A * | 4/2000 | Kristbjarnarson | 600/509 |
| 6,095,991 A * | 8/2000 | Krausman et al. | 600/595 |

(Continued)

FOREIGN PATENT DOCUMENTS

| | | | |
|---|---|---|---|
| WO | WO 2010035187 A1 * | 4/2010 | |
| WO | WO 2010105045 A2 * | 9/2010 | |

OTHER PUBLICATIONS

Chuo, Y, et al; "Mechanically Flexible Wireless Multisensor Platform for Human Physical Activity and Vitals Monitoring"; IEEE Transactions on Biomedical Circuits and Systems, vol. 4, No. 5, Oct. 2010; p. 281-294.*

(Continued)

*Primary Examiner* — Gary Jackson
*Assistant Examiner* — Marie Archer
(74) *Attorney, Agent, or Firm* — Muir Patent Law, PLLC

(57) ABSTRACT

Some embodiments are directed to an apparatus for monitoring patient orientation. A reusable sensor is configured to detect inclination angles of an anterior region of the patient. An elongated disposable attachment device is configured for removable attachment to both the sensor and the patient's anterior region such that the direction of elongation of the attachment device extends along the patient's sternum. The attachment device includes a sensor attachment portion configured for removable attachment to the sensor such that the sensor is prevented from direct contact with the patient, and a patient attachment portion configured for removable attachment to the patient's anterior region.

30 Claims, 20 Drawing Sheets

(56) References Cited

U.S. PATENT DOCUMENTS

| | | | |
|---|---|---|---|
| 6,129,686 A | 10/2000 | Friedman | |
| 6,307,481 B1 | 10/2001 | Lehrman et al. | |
| 6,356,203 B1* | 3/2002 | Halleck et al. | 340/689 |
| 6,501,386 B2 | 12/2002 | Lehrman et al. | |
| 6,575,916 B2 | 6/2003 | Halleck et al. | |
| 6,605,046 B1* | 8/2003 | Del Mar | 600/507 |
| 6,661,347 B2 | 12/2003 | Lehrman et al. | |
| 6,864,796 B2 | 3/2005 | Lehrman et al. | |
| 7,002,482 B2 | 2/2006 | Callaway | |
| 7,066,894 B2 | 6/2006 | Halleck et al. | |
| 7,145,461 B2 | 12/2006 | Lehrman et al. | |
| 7,226,422 B2* | 6/2007 | Hatlestsad et al. | 600/534 |
| 7,423,537 B2 | 9/2008 | Bonnet et al. | |
| 7,479,890 B2 | 1/2009 | Lehrman et al. | |
| 7,610,094 B2 | 10/2009 | Stahmann et al. | |
| 7,661,200 B2 | 2/2010 | Bonnet et al. | |
| 7,698,830 B2 | 4/2010 | Townsend et al. | |
| 7,833,188 B2 | 11/2010 | Gerber | |
| 7,857,088 B2 | 12/2010 | Field et al. | |
| 7,987,069 B2 | 7/2011 | Rodgers et al. | |
| 8,002,465 B2 | 8/2011 | Ahn | |
| 8,025,632 B2 | 9/2011 | Einarsson | |
| 8,121,673 B2 | 2/2012 | Tran | |
| 8,200,321 B2 | 6/2012 | McCombie et al. | |
| 8,204,597 B2 | 6/2012 | Gerber et al. | |
| 8,204,786 B2 | 6/2012 | LeBoeuf et al. | |
| 8,217,795 B2 | 7/2012 | Carlton-Foss | |
| 8,221,323 B2 | 7/2012 | Zhang et al. | |
| 8,226,571 B2 | 7/2012 | Landesberg et al. | |
| 8,397,393 B2* | 3/2013 | Johnson et al. | 33/333 |
| 8,401,666 B2 | 3/2013 | Skelton et al. | |
| 8,489,192 B1 | 7/2013 | Hlavka et al. | |
| 8,531,291 B2 | 9/2013 | Tran | |
| 8,606,592 B2 | 12/2013 | Hyde et al. | |
| 8,668,643 B2* | 3/2014 | Kinast | 600/300 |
| 2005/0126026 A1 | 6/2005 | Townsend et al. | |
| 2005/0142070 A1 | 6/2005 | Hartley et al. | |
| 2005/0237209 A1 | 10/2005 | Van Dongen | |
| 2006/0021240 A1* | 2/2006 | Horgan | 33/366.11 |
| 2006/0195051 A1* | 8/2006 | Schnapp et al. | 600/595 |
| 2008/0275349 A1 | 11/2008 | Halperin et al. | |
| 2008/0287748 A1 | 11/2008 | Sapounas et al. | |
| 2008/0294022 A1 | 11/2008 | Sharf et al. | |
| 2009/0018407 A1 | 1/2009 | Jung et al. | |
| 2009/0024065 A1 | 1/2009 | Einarsson | |
| 2010/0145235 A1 | 6/2010 | Goldbeck et al. | |
| 2010/0298651 A1* | 11/2010 | Moon et al. | 600/301 |
| 2011/0014954 A1 | 1/2011 | Dossas et al. | |
| 2011/0144526 A1 | 6/2011 | Stahmann et al. | |
| 2011/0275942 A1 | 11/2011 | Stahmann et al. | |
| 2012/0065524 A1 | 3/2012 | Morren et al. | |
| 2012/0172681 A1* | 7/2012 | Sun et al. | 600/301 |
| 2012/0179005 A1 | 7/2012 | Mccool | |
| 2012/0196623 A1* | 8/2012 | Kwong | 455/456.3 |
| 2012/0197323 A1 | 8/2012 | Elferri et al. | |
| 2012/0298105 A1 | 11/2012 | Osorio | |
| 2013/0116584 A1* | 5/2013 | Kapoor | 600/513 |
| 2013/0116602 A1* | 5/2013 | Van Den Heuvel et al. | 600/595 |
| 2013/0238049 A1 | 9/2013 | Simon et al. | |
| 2014/0051946 A1* | 2/2014 | Arne et al. | 600/301 |

OTHER PUBLICATIONS

Boonstra, M.C. et al; "The accuracy of measuring the kinematics of rising from a chair with accelerometers and gyroscopes"; Journal of Biomechanics 39 (2006) 354-358.*
Godfrey, A. et al; "Comparison of the performance of the activPALTM Professional physical activity logger to a discrete accelerometer-based activity monitor"; Medical Engineering & Physics 29 (2007) 930-934.*
Godfrey, A. et al; "Activity classification using a single chest mounted tri-axial accelerometer"; Medical Engineering & Physics 33 (2011) 1127-1135.*
Najafi, B. et al; "Measurement of Stand-Sit and Sit-Stand Transitions Using a Miniature Gyroscope and Its Application in Fall Risk Evaluation in the Elderly"; IEEE Transactions on Biomedical Engineering, vol. 49, No. 8, Aug. 2002; p. 843-851.*
Technical Data Sheet: "Sleep Image." D-1008-035 Rev. 3.0.
Drakulovic et al. "Supine body position as a risk factor for nosocomial pneumonia in mechanically ventilated patients: a randomized trial". The Lancet, vol. 354:1851-1858. Nov. 27, 1999.
Collard et al. "Prevention of Ventilator-Associated Pneumonia: An Evidence-Based Systematic Review." American College of Physicians—American Society of Internal Medicine, vol. 138, No. 6, pp. 494-501, Mar. 18, 2003.
Park et al. "An Ultra-Wearable, Wireless, Low Power ECG Monitoring System." Proc. IEEE BioCAS, Nov. 29-Dec. 1, 2006 (all pages), p. 1-4.
Jallon et al. "Detection system of motor epileptic seizures through motion analysis with 3D accelerometers." 31$^{st}$ Annual International Conference of the IEEE EMBS, pp. 2466-2469, Sep. 2-6, 2009.
"Variation in Critical Care Beds Per Capita in the United States: Implications for Pandemic and Disaster Planning." JAMA, vol. 303, No. 14, pp. 1371-1372, Apr. 14, 2010.
Hummel et al., "Continuous measurement of backrest elevation in critical care: A research strategy." Crit Care Med vol. 28, pp. 2621-2625, No. 7, 2000.
Technical Data Sheet: "iMONNIT: Wireless Sensor Monitoring and Notification Systems." Jul. 2011 (all pages), p. 1-2.
Technical Data Sheet: "Monnit WIT, Wireless Accelerometer." Feb. 2012 (all pages), p. 1-2.
Mizell, David. "Using Gravity to Estimate Accelerometer Orientation." Proceedings of the Seventh IEEE International Symposium on Wearable Computers (ISWC'03), p. 252, 2003.
Hall et al. "National Hospital Discharge Survey: 2007 Summary." National Health Statistic Reports, No. 29, pp. 1-20, Oct. 26, 2010.
Zhang et al. "An New Filtering Methods in the Wavelet Domain for Bowel Sounds." (IJACSA) International Journal of Advanced Computer Science and Applications, vol. 1, No. 5, pp. 26-31, Nov. 2010.
Phan et al. "Estimation of respiratory waveform and heart rate using an accelerometer." 30th Annual International IEEE EMBS Conference, Vancouver, British Columbia, Canada, pp. 4916-4919, Aug. 20-24, 2008.
Van Nieuwenhoven et al. "Feasibility and effects of the semirecumbent position to prevent ventilator-associated pneumonia: A randomized study." Crit Care Med vol. 34, No. 2, pp. 396-402, 2006.
Scanlon, Michael. "Acoustic Sensors in the Helmet Detect Voice and Physiology." Sensors, and Command, Control, Communications, and Intelligence (C3I) Technologies for Homeland Defense and Law Enforcement II, Edward M. Carapezza, Editor, Proceedings of SPIE vol. 5071, pp. 41-50, 2003.
Shever et al. "Fall Prevention Practices in Adult Medical-Surgical Nursing Units Described by Nurse Managers." Western Journal of Nursing Research XX(X), 33(3):385-397, Apr. 2011.
Williams et al. "A simple device to increase rates of compliance in maintaining 30-degree head-of-bed elevation in ventilated patients." Crit Care Med, vol. 36, No. 4, pp. 1155-1157, Apr. 2008.
Salhuana, Laura. "Tilt Sensing Using Linear Accelerometers." Freescale Semiconductor Application Note, Document Number: AN3461 Rev. 4, pp. 1-21, Feb. 2012.
Narayanan et al, "Falls Management: Detection and Prevention, using a Waistmounted Triaxial Accelerometer." Proceedings of the 29th Annual International Conference of the IEEE EMBS, pp. 4037-4040, Aug. 23-26, 2007.
Pattison et a, "Sonography of Intraabdominal Gas Collections." AJR:169, pp. 1559-1564, Dec. 1997.
Balonov et al. "A novel method of continuous measurement of head of bed elevation in ventilated patients". Intensive Care Med 33:1050-1054, 2007.
Technical Data Sheet: "Bean Device AX-3D Wireless Triaxal Accelerometer."
Alexiou et al. "Impact of patient position on the incidence of ventilator-associated pneumonia: A meta-analysis of randomized controlled trials". Journal of Critical Care, 24, 515-522, 2009.
Becker et al. "Respiratory Monitoring: Physiological and Technical Considerations." Anesthesia Programs, American Dental Society of Anesthesiology, 56: 14-22, 2009.

(56) References Cited

OTHER PUBLICATIONS

Drakulovic et al. "Supine body position as a risk factor for nosocomial pneumonia in mechanically ventilated patients: a randomized trial". The Lancet, vol. 354. Nov. 27, 1999.

Bos et al. "Lower-Extremity Local Flaps." Journal of the American Academy of Orthopaedic Surgeons, vol. 2, No. 6, Nov./Dec. 1994.

Collard et al. "Prevention of Ventilator-Associated Pneumonia: An Evidence-Based Systematic Review." American College of Physicians—American Society of Internal Medicine, vol. 138, No. 6, Mar. 18, 2003.

Dimoulas et al. "Bowel-sound pattern analysis using wavelets and neural networks with application to long-term, unsupervised, gastrointestinal motility monitoring." Expert Systems with Applications 34, 26-41, 2008.

Carlson et al. "Detecting nocturnal convulsions: Efficacy of the MP% monitor." Seizure 18, 225-227, 2009.

Park et al. "An Ultra-Wearable, Wireless, Low Power ECG Monitoring System."

Jallon et al. "Detection system of motor epileptic seizures through motion analysis with 3D accelerometers." 31st Annual International Conference of the IEEE EMBS, Sep. 2-6, 2009.

"Variation in Critical Care Beds Per Capita in the United States: Implications for Pandemic and Disaster Planning." JAMA, vol. 303, No. 14, Apr. 14, 2010.

Grap et al. "Predictors of backrest elevation in critical care." Intensive and Critical Care Nursing, 19, 68-74, 2009.

Grap et al. "Effect of Backrest Elevation on the Development of Ventilator-Associated Pneumonia." American Journal of Critical Care, 14: 325-332, 2005.

Fleming et al. "Normal ranges of heart rate and respiratory rate in children from birth to 18 years of age: a systematic review of observational studies." Lancet, 377: 1011-18, 2011.

Hummel et al., "Continuous measurement of backrest elevation in critical care: A research strategy." Crit Care Med vol. 28, No. 7, 2000.

Technical Data Sheet: "iMONNIT: Wireless Sensor Monitoring and Notification Systems."

Liu et al. "Oscillating Gas Bubbles as the Origin of Bowel Sounds: A Combined Acoustic and Imaging Study." Chinese Journal of Physiology 53(4): 245-253, 2010.

Technical Data Sheet: "Monnit WIT, Wireless Accelerometer."

Luinge et al. "Measuring orientation of human body segments using miniature gyroscopes and accelerometers." Medical & Biological Engineering & Computing, vol. 43, 2005.

Lee et al. "Detection of falls using accelerometers and mobile phone technology." Age and Ageing, 40: 690-696, 2011.

Kangas et al. "Sensitivity and specificity of fall detection in people aged 40 years and over." Gait & Posture 29, 571-574, 2009.

Orozco-Levi et al. "Semirecumbent Position Protects from Pulmonary Aspiration but not Completely from Gastroesophageal Reflux in Mechanically Ventilated Patients." Am J Respir Crit Care Med vol. 152. pp. 1387-1390, 1995.

Metheny et al. "Tracheobronchial aspiration of gastric contents in critically ill tube-fed patients: Frequency, outcomes, and risk factors." Crit Care Med; 34(4): 1007-1015, Apr. 2009.

Mizell, David. "Using Gravity to Estimate Accelerometer Orientation." Proceedings of the Seventh IEEE International Symposium on Wearable Computers (ISWC'03), 2003.

Hall et al. "National Hospital Discharge Survey: 2007 Summary." National Health Statistic Reports, No. 29, Oct. 26, 2010.

Zhang et al. "An New Filtering Methods in the Wavelet Domain for Bowel Sounds." (IJACSA) International Journal of Advanced Computer Science and Applications, vol. 1, No. 5, Nov. 2010.

Phan et al. "Estimation of respiratory waveform and heart rate using an accelerometer." 30th Annual International IEEE EMBS Conference, Vancouver, British Columbia, Canada, Aug. 20-24, 2008.

Van Nieuwenhoven et al. "Feasibility and effects of the semirecumbent position to prevent ventilator-associated pneumonia: A randomized study." Crit Care Med vol. 34, No. 2, 2006.

Scanlon, Michael. "Acoustic Sensors in the Helmet Detect Voice and Physiology." Sensors, and Command, Control, Communications, and Intelligence (C3I) Technologies for Homeland Defense and Law Enforcement II, Edward M. Carapezza, Editor, Proceedings of SPIE vol. 5071, 2003.

Shever et al. "Fall Prevention Practices in Adult Medical-Surgical Nursing Units Described by Nurse Managers." Western Journal of Nursing Research XX(X) 1-13, 2010.

Williams et al. "A simple device to increase rates of compliance in maintaining 30-degree head-of-bed elevation in ventilated patients." Crit Care Med, vol. 36, No. 4, 2008.

Salhuana, Laura. "Tilt Sensing Using Linear Accelerometers." Freescale Semiconductor Application Note, Document Number: AN3461 Rev. 4, Feb. 2012.

Naranayan et al., "Falls Management: Detection and Prevention, using a Waistmounted Triaxial Accelerometer." Proceedings of the 29th Annual International, Conference of the IEEE EMBS, Aug. 23-26, 2007.

Pattison et al., "Sonography of Intraabdominal Gas Collections." AJR 169, Dec. 1997.

* cited by examiner

SINUS ARRHYTHMIA

METHODS AND APPARATUS FOR MONITORING PATIENT CONDITIONS

BACKGROUND

Some of the disclosed embodiments monitor patient orientation and/or movement, such as patient incline angles and changes of those angles for various purposes. Some of these and/or other embodiments monitor various types of patient movement, including movements caused by respiration and/or heartbeats.

The related art includes various apparatus for monitoring patient incline angles. A few such examples are disclosed below.

I. US 2005/0237209 to Van Dongen

Van Dongen provides a very short disclosure that is directed to improving posture awareness for the purpose of preventing back pain. A device 10 is strapped around a patient's sternum. The device includes an inclinometer 26, which is disclosed as a being an accelerometer (paragraphs [0015] and [0033]), and in particular like the one "marketed under the reference ADXL202EB by the firm Analog Device."

The inclinometer 26 supplies a signal representing the angle of inclination of the sternum relative to a vertical line to a calculator 28. The calculator 28 measures the angle of inclination, compares the measurement with two stored threshold values of the angle, which correspond to forward leaning and backward leaning positions that constitute a pathological risk for the patient, and produces an indication of the threshold values being exceeded. An indicating means can include a light, acoustic, and/or vibrating alarm. The device can also include memory that enables the calculator 28 to count the number of breaches of the forward and backward threshold values observed during a certain time slot.

II. US 2008/0294022 to Sharf et al.

Sharf provides a moderately detailed disclosure that is directed to a medical monitor for measuring patient physiological parameters relating to the progress of birthing, and providing an output based on the measurements. The output is modified based on a patient's posture, i.e., lying on back, lying on side, walking, etc., in order to take into account maternal geometry changes caused by changes in the mother's position.

The posture is determined using an inclination sensor 130 (380), which can be a tilt meter (such as an acceleration meter, beam with strain gauge, or gravity direction detector) or known inclinometer such as is disclosed in Chapter 15 of "The measurement, Instrumentation and Sensors Handbook (ISBN: 0-8493-8347-1)," dated 1999. See paragraphs [0007] and [0087]. Multiple sensors 130 can be used and positioned on any part of the patient's body, including the abdomen, trunk, spine, arm, leg, etc. The sensor 130 can notify a monitor 120 (such as by initiating an alarm, displaying measurements, etc.) when a change in position occurs, such as a change in inclination by more than 30 or 45 degrees relative to the normal. Alternatively, the sensor 130 can notify the monitor 120 of patient inclination periodically, continuously, when a significant change occurs, at set intervals, etc.

III. US 2010/0145235 to Goldbeck et al.

Goldbeck provides a very short disclosure that is directed to a device for fixing at least one fibrous strip FB to a patient's body part for the purpose of measuring bending angles (flexions and torsions), such as the bending angle of the patient's spine. The fibrous strip includes at least one fibre-optic sensor with multiple sensitive zones. Bending angles are determined based on variance of light attenuation as a function of the bending angle of the fiber optic sensor.

A fixing unit includes a fixing part BM for applying part of the fibrous strip to the body part, and a fixing loop BS for guiding the fibrous strip along an axis of three-dimensional space. This sensor provides reliable measurements because the fibre sensor follows the curvature of the body and the fixing unit avoids slippage even during patient movement.

IV. U.S. Pat. No. 8,401,666 to Skelton et al.

Skelton provides a very detailed disclosure that is directed to adjusting parameter values for stimulation therapy based on detected patient activity, such as a change in the patient's posture. In other words, certain therapy modifications are applied for different changes in the patient's detected posture. An implantable medical device (IMD) 14, such as an implantable neuro-stimulator, is implanted within a patient's body to provide neuro-stimulation therapy. The IMD 14 may operate with implantable leads, or alternatively be a leadless stimulator that operates with one or more arrays of electrodes arranged on an external housing.

A posture state module 86 allows the IMD 14 to sense the patient's posture state, e.g., posture, activity or any other static position or motion of the patient 12. The posture state module 86 includes one or more accelerometers, such as three-axis accelerometers and/or micro-electro-mechanical accelerometers, capable of detecting static orientation or vectors in three dimensions. Alternatively, the posture state module 86 can include one or more gyroscopes, piezoelectric crystals, pressure transducers or other sensors to sense the patient's posture state. The generated posture state information may correspond to an activity and/or posture undertaken by the patient 12 or a gross level of physical activity. The posture state module 86 may also be configured to sense one or more physiological parameters, i.e., heart rate, temperature, respiratory rate, pH, etc. (See Col. 18, posture state module 86 lines 50-64; and col. 19, line 64-col. 20, line 7. In response to the posture state information received from the posture state module 86, the IMD 14 may change program groups, stimulation amplitudes, pulse widths, pulse rates, etc. (See col. 10, lines 24-39).

V. U.S. Pat. No. 8,002,465 to Ahn

Ahn provides a very detailed disclosure that is directed to real time targeted delivery of radiation or nuclear medicines for diagnostic or therapeutic purposes by accurately measuring patient position. A plurality of sensors are arranged, such as in an array, on a table or flat surface, or in a mask or mold of the abdomen and/or pelvis, to assess the patient's position. The sensors can be removably attached with an adhesive or permanently attached to an immobilization device. The sensors are directed to ensuring that the patient is positioned during treatment in an orientation that is identical to the original planning scan.

VI. U.S. Pat. No. 7,833,188 to Gerber

Gerber provides a very short disclosure that is directed to a patient angle sensor that is used with gastric feeding devices to shut off or reverse the flow of fluid in a tube when the angle of a bed ridden patient becomes sufficient to allow gastric juices to percolate up through the esophagus and into the lungs, which can result in aspiration pneumonia. A sensor senses when a patient slides down below a certain predetermined angle, and turns off a pump to prevent further fluid from entering the stomach and hence the esophagus. When the device senses that the patient's orientation is below a certain angle, the hospital staff can be alerted, and the head or foot portion of the bed may be raised to prevent further downward sliding.

A sensor 200 is placed at the patient's chest, and can be affixed to the patient directly (such as by adhesives) or to the patient's clothing. The sensor 200 can be any device that senses angles, and can include a wide range of sensing technologies, such as mercury filled insulative containers with electrical contacts, magnetic sensors, optical sensors, etc. More sophisticated sensors can be used that provide a signal indicative of the actual angle of orientation of the patient, as opposed to the angle merely exceeding a threshold value, which may provide early warning of a patient sliding downward.

VII. U.S. Pat. No. 7,002,482 to Callaway

Callaway provides a very short disclosure that is directed to remote monitoring of bedridden patients to prevent injurious falls should the patient attempt to get out of bed. A mercury switch is only actuated when the patient moves a certain way. An internal cavity of the switch controls movement of a mercury ball 15 into and out of engagement with two electrical contacts. The internal cavity has a truncated cone for receipt of the mercury ball, a surface of revolution sloping outward from the opening of the truncated cone, and an interruption ramp 19 in the surface of revolution to guide the mercury ball into the truncated cone for actuation of a switch when a critical angle of the switch has been exceeded. (See col. 1, lines 43-54; and col. 3, lines 46-55).

VIII. U.S. Pat. No. 4,348,562 to Florin

Florin provides a very short disclosure that is directed to a mercury switch assembly that is secured to an anterior horizontal surface of a patient for the purpose of detecting certain angular deviations of the patient's body. The switch is connected to an electrical alarm system to warn an attendant of certain patient movements that may precede a fall, i.e., change from a horizontal position of an anterior surface of the chest or thigh to a more vertical position.

SUMMARY

However, the related art fails to provide methods and apparatus for monitoring patient orientation and/or movement that address at least one of a variety of issues, including but not limited to enhanced accuracy, patient comfort, reducing costs (apparatus costs and/or service costs), enhancing ease of use, enhancing data collection and use of such data for a variety of purposes related or unrelated to issues related to patient orientation and/or movement, etc.

For example, some of the disclosed embodiments are directed to: 1) varying the frequency of chest incline measurements, such as based on changing patient conditions; 2) certain applications of monitoring patient inclines over time, such as addressing seizures, SIDS, sleep related conditions, etc., and generating various types of relevant reports, e.g., indicating a percentage of time in which the patient chest incline angle is less than a certain angle (e.g., 30 degrees) over a certain period (e.g., over 24 hours); and 3) using the same accelerometer that measures patient incline to also measure other patient conditions, i.e., respiration, heart rate, gastrointestinal function, and related applications.

A few such embodiments are disclosed below for exemplary purposes. However, the following disclosure is not intended to be an exhaustive or complete listing of all embodiments disclosed herein or otherwise covered by the invention.

One such exemplary embodiment is directed to an apparatus for monitoring patient orientation. A reusable sensor is configured to detect inclination angles of an anterior region of the patient. An elongated disposable attachment device is configured for removable attachment to both the sensor and the patient's anterior region such that the direction of elongation of the attachment device extends along the patient's sternum. The attachment device includes a sensor attachment portion configured for removable attachment to the sensor such that the sensor is prevented from direct contact with the patient, and a patient attachment portion configured for removable attachment to the patient's anterior region.

In some of these embodiments, the sensor attachment portion is elongated, and the patient attachment portion includes two separate attachment portions that are each disposed at opposite ends of the elongated sensor attachment portion. In some such embodiments, at least a part of the sensor attachment portion is hollow and configured for disposing the sensor therein. In other embodiments, the sensor attachment portion defines a pouch that is configured for disposing the sensor therein. In some of these embodiments, the pouch is defined at an upper surface of the sensor attachment portion.

In some embodiments, the sensor is an accelerometer. In some of these and/or other embodiments, the sensor also detects at least one of heart rate, respiratory rate, and gastrointestinal function.

Some embodiments also include a controller that is spaced from the sensor, and a transmitter that transmits signals between the sensor and the controller. In some of these embodiments, the controller includes an indicator that enables viewing of the incline angles detected by the sensor. In some of these and/or other embodiments, the controller controls the sensor to vary the frequency of incline measurements.

In some of these or other embodiments, the controller provides an alarm indication if the sensor detects certain incline angles. In some of these embodiments, the controller enables overrides the alarm indication for a certain period regardless of the detected inclination angle. In some of these and/or other embodiments, the controller provides an alarm indication if the sensor detects that the patient's incline angle falls below a certain angle. In some of these and/or other embodiments, the controller provides an alarm indication if the sensor detects that the patient's incline angle falls below 30 degrees. In some of these and/or other embodiments, the controller provides an alarm indication if the sensor detects that the patient's incline angle indicates that the patient is attempting to stand. In some of these and/or other embodiments, the controller provides an alarm indication if the sensor detects that the patient's incline angle exceeds a certain angle.

In some of these and/or other embodiments, the controller provides historical data of detected inclination angles in the form of inclination angle ranges versus periods of time. However, the controller of other embodiments can be configured to provide any useful representation of such historical data.

In some of these and/or other embodiments, the controller provides a sensor calibration function. In some of these embodiments, the controller is configured such that the calibration function includes receiving a supine detected inclination angle when the patient is oriented in a supine position, and calibrating the supine detected inclination angle as 0 degrees. In some of these or other embodiments, the controller is configured such that the calibration function includes receiving an erect detected inclination angle when the patient is oriented in an erect position, and calibrating the erect detected inclination angle as 90 degrees.

A few other exemplary embodiments are disclosed below for exemplary purposes.

I. Setpoint and Threshold Functionalities

A. Deviating From Setpoint By Predetermined Amount

B. Deviating From Chest Incline Threshold

II. Measurement Frequency
III. Monitoring/Recording Inclines Over Time
IV. Fall Prevention Monitoring
V. Respiratory Monitoring
  A. Only Respiration
  B. Combining Measured Respiration With Other Data
  C. Monitoring Respiration Over Time
VI. Heart Rate Monitor
VII. Monitoring For Movement and Orientation Based Conditions Including Seizures, SIDS, etc.
VIII. Monitoring Conditions Related To Sleep
IX. Gastrointestinal Monitoring
  A. Assessing Gastrointestinal Motility via Accelerometer(s)
  B. Assessing Other Aspects Of Gastrointestinal Function and Motility via Accelerometer(s)
I. Setpoint and Threshold Functionalities
  A. Deviating from Setpoint by Predetermined Amount Some embodiments provide an indication of deviation from a certain incline setpoint or setpoints, i.e., determining whether the measured patient chest incline exceeds or decreases below the incline setpoint by a predetermined angle. In one example, if the incline setpoint is 30 degrees, and the predetermined magnitude of deviation is 10 degrees, then the sensor and/or sensor system will provide an alarm or other type of indication upon receipt of data indicating that the sensor has measured a patient incline angle that is less than 20 degrees and/or greater than 40 degrees.

Other embodiments cover subsets and/or variations from the above functionality. For example, some embodiments provide the alarm/indication only if the measured patient chest incline is less than the incline setpoint by an amount exceeding a predetermined magnitude. Other embodiments provide the alarm/indication only if the measured patient chest incline is greater than the incline setpoint by an amount exceeding the predetermined magnitude. Still other embodiments, such as the example provided in the preceding paragraph, provide the alarm/indication if the measured patient chest incline is either greater than or less than the incline setpoint by an amount exceeding the predetermined magnitude.

B. Deviating from Chest Incline Threshold

Other embodiments monitor deviations in patient incline differently than the above embodiments that determine whether a measured patient chest incline deviates from a chest incline setpoint by a certain magnitude. For example, some embodiments monitor whether a measured patient incline is less than or greater than a certain patient chest incline threshold. For example, as currently recommended by SCCM/ASPEN, it may be beneficial for the angle of inclination of certain patients, such as those at risk of reflux, to maintain an angle of incline of at least 30 degrees, i.e., 30 degrees or more. In these exemplary embodiments, the sensor and/or sensor system would provide an alarm/indication upon receipt of data indicating that the sensor has measured a patient chest incline angle that is less than 30 degrees.

This embodiment is particularly applicable for patients at risk for aspiration of gastric contents, e.g., gastric secretions and/or tube feeds, where it is beneficial for the patient's upper chest to be inclined by at least 30 degrees relative to the patient's abdomen. This procedure uses gravity to reduce, minimize and/or prevent columnar reflux of gastric contents. Patients at increased risk may include, but are not limited to: 1) patients with a history of aspiration; 2) patients at increased risk for aspiration, e.g., receiving enteral tube feeds, such as gastric or post-pyloric feeding; 3) ICU patients paralyzed with a neuromuscular blocker to facilitate their care, e.g., mechanical ventilation in extreme hypoxemia; 4) patients with a history of stroke or other neurological condition which could impair ability to protect their airway, e.g., cough, swallow, etc.; and/or 5) patients with decreased mental status due to drugs (e.g., sedatives, narcotics) or due to an underlying condition, e.g., head injury, stroke, or coma that may also impair the ability to protect the patient's airway.

II. Measurement Frequency

In some embodiments, the frequency of chest incline measurements is preset, such as every one minute. Thus, in these embodiments, the sensor and/or sensor system measures the patient chest incline every one minute. However, other embodiments vary the frequency of chest incline measurements. In one such embodiment, a change in the patient's condition changes the frequency of subsequent measurements. In some of these embodiments, if the chest incline angle is within normal or substantially normal parameters, then an operation can be performed wherein the chest incline angle is measured less frequently, such as only once every ten minutes, which may be beneficial for various reasons, such as to enhance, improve, or even optimize battery life.

In one such embodiment, the sensor, such as an accelerometer, only performs the chest incline measurement operation once every ten minutes, if the immediately previously measured chest incline angle was within normal parameters. In some of these embodiments, a processor cooperates with an accelerometer to trigger the accelerometer to perform the chest incline measurement only once every 10 minutes. However, if the measured chest incline is concerning (e.g., a measurement of 10 degrees if a 30 degree chest incline is prescribed), then the processor increases the rate of measurement, such as once every one or two minutes.

In another embodiment, a processor that is incorporated into, or otherwise in communication with, the sensor or sensor system can use additional information to change the frequency of measurements. For example, if data is obtained that indicates an increased risk of occurrence of an unwanted condition, such as a dangerous condition, then the chest incline can be measured relatively more frequently. This operation may be beneficial because the increased data obtained by the relatively more frequent chest incline measurements may be used to avoid, prevent or reduce the impact of the unwanted or potentially dangerous condition. Contrarily, if data is obtained that indicates a decreased risk of occurrence of an unwanted or dangerous condition, then the chest incline can be measured relatively less frequently. This operation may be beneficial for other reasons, such as to conserve battery life or increase longevity of the sensor or sensor system.

For example, the processor can take into account several factors that may predict whether a patient is likely to be sleeping or heavily sedated, e.g., late at night, such as at 2 a.m. In this condition, the patient's heart rate and respiratory rates slow, such as 10% lower than the median value obtained during day time, and the patient is subject to minimal movement as is consistent with sleep. In such a condition, the frequency of measurements of the patient chest incline can be reduced, such as every 15 minutes, in order to conserve battery life, enhance sensor longevity, etc.

III. Monitoring/Recording Inclines Over Time

Some embodiments use the patient chest incline sensor or sensor system to monitor deviations in patient chest incline for reasons other than those discussed above. The incline sensor of some of these embodiments transmits patient incline data to a recorder, controller, processor, or other device, for the purpose of showing or otherwise indicating a trend in degree of incline over time. One such embodiment enables the indication of patient incline data over various periods. For example, in this embodiment, an operator can indicate the patient incline data over a first period (e.g., over one hour), over a second period (e.g., over 6 hours), over a third period (e.g., over 12 hours), over a fourth period (e.g., over 24 hours), etc.

In another embodiment, more than one deviation in position is monitored, and an indication/alarm is provided to indicate occurrence of the requisite deviations in positions. For example, for a patient being enterally fed into the stomach, an indication/alarm may provide an indication as to whether the incline of the upper chest/abdomen is less than 30 degrees, or approximately 30 degrees, such as +/−5 degrees, for example, relative to the floor. Alternatively, or in addition to the above, an indication/alarm may provide an indication as to whether the upper chest/abdomen is greater than 75 degrees, or approximately 75 degrees, such as +/−5 degrees, which may indicate that the patient is attempting to sit up, stand and/or possibly leave the hospital bed, which could predispose the patient to injury. In yet another embodiment, a recorder, monitor, or other device provides different types of indications, such as different sounds, to enable medical care providers, such as clinicians, to quickly and/or easily differentiate one type of patient condition deviation from another type.

Still other embodiments include or otherwise utilize any relevant or beneficial use or manipulation of the patient chest incline data. For example, some embodiments generate and/or supply a report of patient incline data as a function of certain parameters. One such embodiment generates and supplies a report indicating a percentage of time in which the patient chest incline angle is less than a certain angle (e.g., 30 degrees) over a certain period (e.g., over 24 hours). Other embodiments provide a report indicating a percentage of time in which the patient chest incline angle is greater than a certain angle (e.g., 45 degrees) over a certain period (e.g., over 6 hours). However, the above manipulations and/or uses of data are merely provided for exemplary purposes, and embodiments are intended to cover any relevant or beneficial use or manipulation of the patient chest incline data.

Some embodiments include other alternative or additional functions or operations. For example, some embodiments include a pause feature that temporarily interrupts monitoring, tracking, etc., of the patient chest incline data. This interruption can be performed in any manner, such as by interruption of the transmission of the patient chest incline data to the recorder, controller, processor, or other device. As an alternative, the interruption can by performed by the recorder, controller, processor, or other device.

The pause/interruption feature disclosed above can be beneficial for a variety of reasons. For example, this feature may enable a medical care provider, such as a doctor, nurse, physical therapist, etc., to interrupt patient incline monitoring during events where the monitoring is not relevant or would lead to ambiguous or erroneous results. In one example, the medical care provider may interrupt or otherwise disable the patient incline monitoring during a temporary period where the patient: 1) needs to be moved, such as during physical therapy, 2) is removed from a hospital bed, 3) is placed in a horizontal position to perform a certain procedure, etc. The patient chest incline monitoring can then be resumed after termination of the temporary period.

IV. Fall Prevention Monitoring

Some embodiments provide an indication/alarm if the patient's incline increases to above a certain threshold, such as 85 degrees, which would occur if a patient is standing or attempting to stand. The patient inline can be determined or based on any relevant measurements. For example, the patient incline can be based on measurements taken at ends of the patient's body, such as the patient's head and feet. Alternatively, this determination can be based on measurements taken along the patient's chest, abdomen, back, etc. For example, measurement at the upper leg may reduce false positive alarms that may occur with other sensor positions. Position on the upper leg will not be affected by the patient sitting upright, since even while in the sitting position the upper leg will still be largely perpendicular to the floor (0 degrees incline), and only with standing will the upper leg be at an incline of approximately 90 degrees.

However, other embodiments do not make the above determinations based on patient incline, and instead focus on other measurements. For example, some embodiments use a sensor, such as an accelerometer, to detect a type of movement, such as a significant movement characteristic, of a patient indicative of an attempt to ambulate, i.e., walk. Some of these embodiments combine the accelerometer's measurement of movement with patient incline measurements to detect a patient's attempt to get up or ambulate.

V. Respiratory Monitoring

A. Only Respiration

Many of the disclosed embodiments are directed to respiratory monitoring, i.e., respiration rate, depth of breath, etc. Some of the embodiments use sensors, such as accelerometers, to measure patient chest incline angles to measure certain physiological conditions relevant to aspects of respiration. For example, some of these accelerometers and sensor systems use the measured chest inclines to determine the movement of the chest up and down that occurs during breathing (respiration). However, not all of the embodiments focus on chest incline monitoring, and instead measure other conditions. For example, some embodiments include sensor(s), such as other types of accelerometers, that measure changes in position or motion of the sensor and/or chest to measure certain physiological conditions relevant to aspects of respiration.

Some of these embodiments use computer algorithms to diagnose different pathologic conditions of breathing using the respiration rate data. For example, in some embodiments, a default indication/alarm is set to indicate certain conditions, such as a condition where the respiratory rate is less than a certain number, such as 10, or greater than a certain number, such as 30. Indication/alarm thresholds can be graded so that different types of indications/alarms are provided depending on the sensed conditions. As one example, a low respiratory rate indication/alarm can be provided if the respiratory rate is less than 10 but greater than 4, while a very loud critical indication/alarm can be provided if the respiratory rate is 4 or less to indicate impending respiratory arrest. Indication/alarm thresholds can also be graded based on the trend of sensed conditions. Specific sensed conditions may initiate additional one time and periodic measurements to better determine the patient's condition. As one example, a low respiratory rate below 15 may initiate more frequent measurements, such as respiration rate, respiration depth, heart rate, and other exemplary measurements, to monitor the patient more closely and determine if the condition changes. If the subsequent measurements indicate the patient condition is improving, the frequency and type of measurements may be decreased to conserve battery life. Alternatively, if the subsequent measurements indicate the patient condition is not improving, in one exemplary embodiment the device may initiate a command to interact directly with the patient. As one example, the device may initiate a verbal message or loud buzzer to wake the patient in an effort to increase breathing or otherwise improve their condition. In another example, the device may initiate an electric shock, vibration, or other type of stimulation to wake the patient to increase breathing or otherwise improve their condition.

Some of these embodiments use accelerometer(s) to monitor respiration by measuring magnitude of chest excursion, i.e., a relatively large breath (tidal volume) results in a relatively large movement of the accelerometer, whereas a relatively small breath results in a relatively small movement of the accelerometer.

Some embodiments measure both the respiratory rate as well as the depth of respiration. Embodiments are intended to include any methods and apparatus to perform this dual monitoring and/or use or apply the data obtained thereby. For example, a computer algorithm can be provided to use or apply both the respiratory rate as well as depth of respiration data for any purpose. This dual monitoring can be useful for hospitalized patients at risk for apnea or respiratory depression, e.g., patients in a non-ICU setting who are receiving respiratory depressants (e.g., opiate type pain medications). For example, it is common in some hospitals for patients with a history of severe obstructive sleep apnea to need ICU care after routine surgery due to potential adverse effects of opiates on respiration. Therefore, the above dual monitoring is beneficial by enabling patients to be located in a non-ICU setting (e.g., hospital ward) soon after surgery, such as the first night after surgery, thereby reducing costs and making the ICU available for patients in greater need of ICU care.

B. Combining Measured Respiration with Other Data

Some embodiments combine the use of respiration data with other data for a variety of useful purposes. As one example, patient mobility can be taken into account with the respiratory data to arrive at a certain diagnosis or to make some other determination. Heart rate is another source of data that can similarly be taken into account with the respiratory data. In fact, multiple types of data, e.g., both mobility data and heart rate data, can be taken into account with respiratory data to arrive at a certain diagnosis or to make some other determination. Some of these determinations relate directly or indirectly to certain physiological conditions of the patient, such as gastric health, adequacy of resuscitation, etc. Contrarily, other determinations relate to or otherwise facilitate the interpretation of other data, such as to achieve an enhanced interpretation of respiratory data.

As one example, in some scenarios, a patient can tolerate a lower heart rate and respiratory rate if the patient is immobile. Thus, the sensor(s) and/or sensor system(s) of some embodiments monitor the above physiological conditions and provide diagnoses or make other determinations based on the combined data.

Physiological conditions of the patient, as well as factors external to the patient, can be taken into account, such as by a processor's algorithm of the sensor(s) or sensor system(s), for any useful purpose, such as to provide or facilitate an enhanced or improved interpretation of respiratory monitoring. An example of a physiological condition of the patient that can be taken into account as disclosed above is the patient's heart rate. Another example of such a condition is evidence of patient movement, such as walking, based on a signature of acceleration and/or deceleration in the vertical and horizontal directions that are consistent with the type of movement at issue, such as walking. In these examples, if the patient appears to be walking in the hospital based on an increase in movement and heart rate, then an increase in respiratory rate would be expected. However, the above scenarios are merely provided for exemplary purposes, and are not intended to be an exhaustive listing of physiological conditions of the patient that can be taken into account for any beneficial reason, such as to facilitate an enhanced interpretation of respiratory data.

An example of an external factor is the time of the day. For example, at night, such as 3:00 am, it is more likely that the patient is in bed and sleeping, therefore, one would predict there to be less movement, a lower heart rate, and a lower respiratory rate consistent with normal patterns of respiration during sleep versus awake states. However, the above scenario is merely provided for exemplary purposes, and is not intended to be an exhaustive listing of external of the patient that can be taken into account for any beneficial reason, such as to facilitate an enhanced interpretation of respiratory data.

In some embodiments, an indication/alarm is provided if the patient's respiratory rate drops below a certain lower setpoint or threshold. In some of these embodiments, or other embodiments, an indication/alarm is provided if the patient's respiratory rate rises above a certain higher setpoint or threshold. These embodiments are beneficial in various respects, such as by providing an alert or indication, such as to a caregiver, that the patient's respiratory rate has deviated from a respiratory rate or range of rates that are desired. However, other data, such as data relating to the patient's physiological conditions and/or external factors, can be used to modify the above lower and/or higher setpoints or thresholds.

In one embodiment, the lower respiratory rate setpoint or threshold is modified based on the patient's level of activity. For example, the lower respiratory rate setpoint may be reduced if the patient is inactive, such as asleep, while the lower respiratory rate setpoint may be increased if the patient is engaged in some activity. This embodiment may be beneficial because a reduced lower respiratory rate may be acceptable, or at least not sufficiently undesirable so as to warrant communication of an indication/alarm, if the patient is inactive. Contrarily, an increased respiratory rate may be necessary if the patient is engaged in a certain activity. In one such embodiment, a lower respiratory rate threshold, such as a rate of 15, may trigger an indication/alarm if the sensor(s)/sensor system(s) determines that the patient to be awake and/or moving. On the other hand, if the sensor(s)/sensor system(s) determines that the patient is asleep and/or not moving, then a more appropriate lower respiratory rate threshold may be set, such as a respiratory rate of 10, to account for slower respirations during sleep, and to reduce of avoid "alarm fatigue," such as by nursing staff.

C. Monitoring Respiration Over Time

Some embodiments include sensor(s) and sensor system(s) that monitor, record, and utilize/apply respiratory and other data, including but not limited to data relating to other physiological conditions, over time. This data is referred to herein as historical data. Some embodiments include a processor that utilizes algorithms to provide indications/alarms, such as "smart alarms," based on historical data for a particular patient. For example, if the patient is monitored for a certain period, such as 72 hours, data relating to patterns of movement (incline, acceleration, etc.), heart rate, respiratory rate, etc., over time and at different times, can be monitored and applied for various beneficial uses/applications.

In some embodiments, this data is used to enhance or improve the discrimination of the sensor(s) and/or sensor system(s) to detect relevant conditions, such as potentially dangerous conditions. For example, mean and 1 and 2 standard deviations for heart rate and respiratory rate can be calculated for periods in which the patient is not moving (immobile), as opposed to periods in which accelerometer data makes clear that the patient is moving. These "normal values" for the patient for the moving and immobile states can be used to determine appropriate but different thresholds for indication/alarm triggers in different states, for example, moving versus immobile.

Similar use of patient historical data can be used in other contexts, such as different states of consciousness, e.g., awake versus asleep, or even different states of sleep. In one such example, data relating to the time of day (e.g., period of 1:00-4:00 am) can be used with data relating to patient movement (e.g., immobility—lack of patient movement) to make certain determinations. In the above example, i.e., period of 1:00-4:00 am and patient immobility, the sensor(s) and/or sensor system(s) can determine that the patient is likely asleep, and modify measured and/or calculated relevant physiological conditions accordingly, e.g., calculate normal (e.g., mean+/−2 SD) values for respiratory rate and heart rate that would be appropriate or otherwise desirable for the patient being asleep. Such calculated values can be used as above to set indication/alarm thresholds for the patient in the likely sleep state.

In addition, historical data for the patient during the above periods can be used to further modify the measured and/or calculated relevant physiological conditions. For example, historical data for the patient's awake and sleep states can be monitored, analyzed and taken into account in determinations/applications, such as the setting of acceptable parameters or indication/alarm thresholds of different physiological conditions, including but not limited to respiratory rate parameters. This feature may be especially beneficial because it personalizes determinations/applications that are more consistent with normal, acceptable, unacceptable, etc., physiological conditions for each specific patient, including but not limited to respiratory rate parameters.

VI. Heart Rate Monitor

Some or all of the sensor(s) and/or sensor system(s) disclosed above can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different or overlapping physiological conditions to measure different aspects of heart rate, i.e., number of beats, strength of beats, regularity of beats, beat anomalies, etc.

VII. Monitoring for Movement and Orientation Based Conditions Including Seizures, SIDS, Etc.

Some of all of the sensor(s) and/or sensor system(s) disclosed above can be applied in the context of monitoring for movement based conditions, including seizures, SIDS, etc., i.e., conditions that are defined by, closely related to, or otherwise affiliated with, certain type(s) of movement (or a lack thereof). Embodiments are intended to measure, directly or indirectly, any other or additional physiological condition from which the specific type(s) of movement (or a lack thereof) at issue can be gleaned or otherwise better understood. For example, some of the embodiments measure different or overlapping physiological conditions to measure the specific type(s) of movement (or a lack thereof) at issue.

Some of the embodiments directed to monitoring physiological conditions indicative of certain type(s) of movement (or a lack thereof) include sensor(s) and/or sensor system(s) having accelerometer(s) that measure dynamic acceleration, i.e., vibration. Some of these sensor(s) and/or sensor system(s) include processor(s) with algorithms to differentiate the body movement(s) at issue, such as body movements caused by seizures, from other types of body movements, such as body movements caused by breathing, beating of the heart, etc. Some of these embodiments can further include algorithms to differentiate between different types or states of the body movement(s) at issue, such as different types or states of seizures.

The above applications are disclosed in the context of different types of body movements, such as occur during seizures, etc. However, other embodiments are directed to detecting, directly or indirectly, lack of certain or all types of body movements. Still other embodiments are directed to detecting physiological conditions, such as certain types of body movements, that may place a patient at risk for certain undesirable and/or harmful conditions, including those that result in a lack of body movement.

VIII. Monitoring Conditions Related to Sleep

Some embodiments have been disclosed above in the context of monitoring different aspects of sleep, such as: 1) to diagnose sleep-related conditions, including but limited to sleep apnea, 2) determining whether a patient is asleep or awake for the purpose of setting parameters relating to respiration, heart rate, etc. However, other embodiments include sensor(s) and/or sensor system(s) that can be applied in the context of monitoring other aspects of, or conditions directly or indirectly related to, sleep, including but not limited to duration, position, movements, quality, etc. A summary of these embodiments, as well as a few specific applications, are disclosed below for exemplary purposes, and are intended as an exhaustive disclosure of all usages of monitoring aspects of sleep or sleep conditions covered by the embodiments.

IX. Gastrointestinal Monitoring

Some of all of the sensor(s) and/or sensor system(s) disclosed above can be applied in the context of monitoring various aspects of gastrointestinal function. Embodiments are intended to measure, directly or indirectly, any physiological condition from which any relevant aspect of gastrointestinal function can be gleaned. For example, some of the embodiments measure different or overlapping physiological conditions to measure the same aspect of gastrointestinal function. Alternatively, some embodiments measure the same, different or overlapping physiological conditions to measure different aspects of gastrointestinal function, i.e., motility, perfusion, etc.

A. Assessing Gastrointestinal Motility Via Accelerometer(s)

Some of the embodiments are directed to monitoring physiological conditions enabling assessment of gastric and/or intestinal motility. These embodiments are intended to include any type of sensor enabling monitoring of these physiological conditions, including but not limited to accelerometer(s), such as those that measure dynamic acceleration, i.e., vibration. There may be a number of vibration sources in the gastrointestinal tract related to motility. For example, the rhythmic motion of peristalsis in the stomach and small intestines produces vibrations. By measuring these vibrations and then correlating over time, there is an opportunity to capture the time and duration of specific phases of digestion. There is evidence the bowel sounds are correlated with motility. Another source of vibrations is the result of oscillating gas bubbles in the small intestine. There is evidence these gas bubbles are continually present in the small intestine.

Embodiments are intended to monitor any physiological condition enabling assessment of gastrointestinal motility. For example, an increase of intestinal contractions/motility may be used as evidence of a healthy or reasonably healthy gastric function, or vice versa, and care may be provided accordingly. Thus, some embodiments include sensor(s)/sensor system(s) that measure/monitor intestinal contractions/ motility over time, determine whether an increase has occurred or is occurring, or vice versa, and provide indications/alarms accordingly.

In an exemplary embodiment, bowel sounds can be auscultated, and the presence of bowel sounds (in conjunction with results from changes in gastric pH changes after pharmacological challenge) can be used to guide decisions to initiate, modify, or terminate enteral feeding. Auscultation of bowel sounds can be performed directly, e.g., with a stethoscope, however, in one exemplary embodiment, bowel sounds are recorded with an electronic stethoscope or microphone, which is coupled with a recorder that can monitor, record, and enable display of continuous data. This exemplary embodiment enables detection of less intense sounds compared with direct auscultation. In other words, direct auscultation is more likely to only allow detection of bowel sounds that are louder, and the sampling period is shorter due to the need for the person listening to be tethered to the patient via the stethoscope.

The various measures of motility can be combined with alerts and other mechanisms to help the clinician monitor the status of the patient. In one exemplary embodiment, an alarm can be set to alert the clinician if a specific level of motility was not reached in any of the above measurement techniques. By comparing the measured level of motility with specific targets and patterns, an assessment can be determined and an alarm triggered if the measured motility is to not sufficient. An alarm can take many exemplary forms, such as an audible or visual alert at the nurse's station, a visual alert integrated into the enteral feeding machine, or an alert directly to the clinician via a text message or other electronic messaging technologies.

An exemplary alerting mechanism may combine measured motility data with other measured data, such as heart or respiration data. In this exemplary embodiment, an indication of insufficient motility combined with abnormal heart and respiratory measurements may indicate the patient's condition is worsening and alert the clinician. In another exemplary embodiment, insufficient motility combined with evidence of esophageal reflux may indicate the patient is not tolerating nutrition and alert the nurse or clinician to adjust care.

B. Assessing Other Aspects of Gastrointestinal Function Via Accelerometer(s)

Embodiments are intended to cover or otherwise include accelerometers for measuring, directly or indirectly, any physiological condition from which any relevant aspect of gastrointestinal function can be gleaned or condition diagnosed. For example, as disclosed in more detail below, some embodiments include accelerometers to measure vibrations in or around a patient's gastrointestinal system for the purpose of diagnosing various conditions, including but not limited to Small Intestinal Bacterial Overgrowth (SIBO), Irritable Bowel Syndrome (IBS), diarrhea, constipation, malabsorption, etc.

An accelerometer can measure patterns and frequency of bowel sounds and correlate these sounds with specific indications such as SIBO, IBS, diarrhea, constipation and malabsorption. In an exemplary embodiment, this could be accomplished by the measurement of gas bubble oscillations as described by Liu. The measurement of gas bubbles may vary by indication and/or type of bacteria that is causing the excess gas excretion. These measurements of bowel sounds could be correlated with the results of a hydrogen breath test, which is used to determine a relative amount of bacteria that may be present the GI tract of a patient. In another exemplary embodiment, the measurements of bowel sounds could be correlated with the results of bacterial cultures of various locations in the small bowel. The result is the measurement of bowel sounds in a patient may then be able to help the clinician more quickly and easily identify specific types and quantities of bacteria that may be present in the patient.

DETAILED DESCRIPTION

Figure 1:
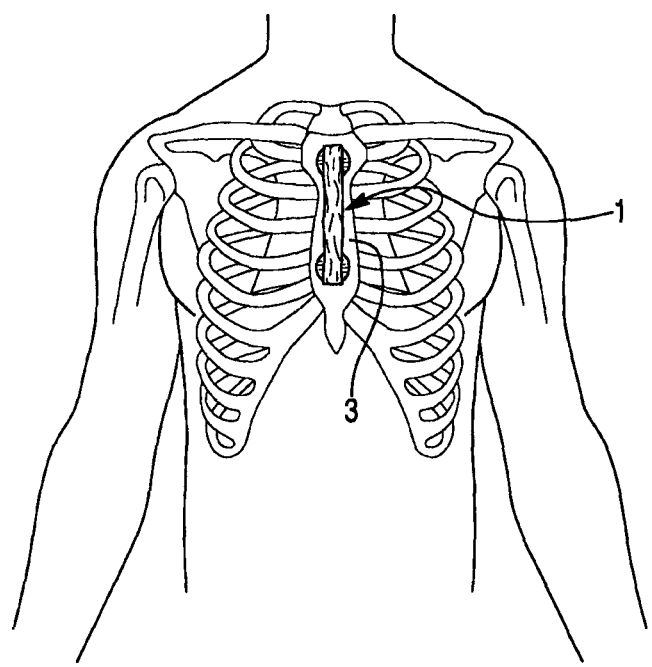
FIG. 1 is a schematic of an apparatus in accordance with an exemplary first embodiment that includes an incline sensor and attachment mechanism attached to an anterior portion of a patient to determine an angle of incline of the patient.

I. Disclosure Summary
II. Accelerometers
III. Incline Sensor Monitoring
  A. Incline Summary
    1. Patient Incline
    2. Incline Sensors
  B. Chest Monitoring
    1. Patient Conditions
    2. Monitoring
      a. Overall Structure(s)
      b. Setpoint and Threshold Functionalities
        i. Deviating From Setpoint By Predetermined Amount
        ii. Deviating From Chest Incline Threshold
      c. Measurement Frequency
      d. Indicator(s) and/or Alarms
      e. Monitoring/Recording Inclines Over Time
      f. Other Applications
  C. Extremity Monitoring
  D. Neck Monitoring
IV. Fall Prevention Monitoring
V. Respiratory Monitoring
  A. General Monitoring and Indications/Alarms
  B. Combining Measured Respiration With Other Data
  C. Monitoring Respiration Over Time
  D. Specific Applications
    1. Conscious Sedation Application
    2. Quantification of Respiratory Depth Variable
    3. Determining Whether Patient is Becoming Tired
    4. Diagnosis of Pathologic Respiratory Conditions
    5. Determining Respiratory Obstructions
VI. Heart Rate Monitor
  A. Summary
  B. Specific Applications
VII. Monitoring For Movement Based Conditions Including Seizures, SIDS, etc.
  A. Summary
  B. Specific Applications
VIII. Monitoring Conditions Related To Sleep
  A. Summary
  B. Specific Applications
IX. Gastrointestinal Monitoring
  A. Assessing Gastrointestinal Motility via Accelerometer(s)
  B. Assessing Gastrointestinal Motility via Substance Indicator(s)
  C. Assessing Other Aspects Of Gastrointestinal Function via Accelerometer(s)
X. Sensor(s) and Sensor System(s)
  A. Exemplary Sensor(s), Indicator(s), and Controller(s)
    1. Exemplary Sensor(s) and/or Attachment Mechanisms
      a. Summary
      b. Anterior Attachment
      c. Posterior Attachment
    2. Exemplary Indicator(s)/Controller(s)
    3. Alternative Indicator(s)/Controller(s)
      a. Dedicated Inputs/Outputs
      b. Touchscreen Display
      c. Exemplary Operation
  B. Exemplary Equipment Packaging
    1. Kit
    2. Processor
    3. Computer Program

I. DISCLOSURE SUMMARY

Exemplary embodiments include methods and apparatus for monitoring patient conditions, i.e., physiological aspects of patients, and in particular enhanced monitoring techniques to facilitate, accelerate and/or otherwise improve patient recovery and/or patient conditions. Some of the disclosed embodiments apply monitoring techniques to previously unmonitored patient conditions, while other embodiments apply monitoring techniques to currently monitored patient conditions in order to monitor these conditions more accurately, completely and/or differently.

Exemplary embodiments are intended to cover any and all patient conditions that are relevant to facilitating, accelerating and/or otherwise improving patient recovery and/or the patient conditions at issue. Some of the disclosed embodiments involve monitoring static or substantially static aspects of patient conditions, such as patient orientation; while other embodiments involve monitoring dynamic or substantially dynamic aspects of patient conditions, such as patient respiration, heart rate, as well as many other physiological patient conditions.

Exemplary embodiments are intended to include or otherwise cover currently known, related art, and/or later developed technologies to perform the disclosed monitoring. Many of the disclosed embodiments perform some or all of the monitoring using accelerometers, which are disclosed in more detail below. However, some embodiments do not use accelerometers to perform any of the monitoring, and instead rely on, or otherwise use, technologies to perform the monitoring that are related to, or even unrelated to, accelerometers.

II. ACCELEROMETERS

Exemplary embodiments include any and all currently known, related art, and/or later developed accelerometer technologies that can be implemented to provide the requisite patient monitoring. A few specific examples of certain applicable accelerometer technologies are discussed below for exemplary purposes only, and are not intended to be an exhaustive list of types of accelerometers that can be used in accordance with the various inventive aspects disclosed herein.

Some of the embodiments disclosed herein include one, two and/or three-axis accelerometers. In some such embodiments, a patient's level of incline is measured using a single axis accelerometer. For example, an accelerometer, such as an accelerometer chip, that measures static acceleration is positioned so as to measure a patient's angle of incline relative to gravity.

In other embodiments, a patient's level of incline is measured using a dual axis accelerometer, where the accelerometer, e.g., accelerometer chip, measures acceleration via two axes. As one example, this dual axis apparatus is used to measure the angle of incline of the patient's upper abdomen/chest in the context of facilitating or ensuring adequate head of bed elevations for certain patients, such as those receiving mechanical ventilation, patients being enterally fed, etc.

However, the above disclosure is merely provided for exemplary purposes, and other types of patient orientations or positioning can be monitored or otherwise determined using the above dual axis accelerometer or other types of sensors. In some embodiments, the patient's orientation or positioning is monitored or determined relative to an axis perpendicular to the first axis. Measurement or monitoring of the second axis can be used to determine whether the patient changes positions, such as the patient deviating from a supine position (i.e., anterior part of body, such as eyes and nipples, facing toward the ceiling) to a prone position (i.e., anterior part of body, such as eyes and nipples, facing toward the floor). This feature may be beneficial or otherwise important for some patients, such as infants at risk for Sudden Infant Death Syndrome (SIDS), to alert clinicians, parents or other care providers to movement of the patient/infant to a prone position that could indicate, cause, facilitate or increase the risk of certain complications.

Other embodiments include accelerometers that measure dynamic acceleration, i.e., based on vibration or movement. The disclosed embodiments are intended to include or otherwise cover any accelerometer technologies that can perform these measurements. For example, accelerometers of the three-axis variety can be used to measure dynamic acceleration, although other configurations are possible. Some embodiments use piezoelectric accelerometers to measure dynamic accelerations, such as vibrations.

Exemplary embodiments are intended to cover accelerometers of any level of sensitivity that may be useful or beneficial. For example, some embodiments include high sensitivity three-axis piezoelectric accelerometers, such as those having sensitivities as low as 0.3 Hz or less. These very sensitive accelerometers can be used to monitor various aspects of a patient's physiology, such as human heart rate, which has a waveform with a frequency in the range of 0-2 Hz. However, other embodiments use less sensitive accelerometers.

Many of the accelerometers used in the disclosed embodiments are in the form of accelerometer chips that include pins for connection to circuit boards. In these embodiments, the pins can be connected directly or indirectly to wires for hard-wired communications, or contrarily to wireless chips or other devices for wireless communications. In many of the hard-wired applications, the accelerometer receives power via wires, while many of the accelerometers used in wireless applications receive power via batteries, such as small watch-type batteries or AAA (triple A) batteries.

Some embodiments include accelerometers that are configured or otherwise made to be disposable after a single or limited number of uses, while other embodiments include accelerometers configured or made to be reusable. In some embodiments, the disposable accelerometers are structured or otherwise configured to facilitate certain beneficial characteristics, such as inexpensive manufacture. In other embodiments, the reusable accelerometers are structured or otherwise configured to enhance certain beneficial characteristics, such as accuracy, durability, and avoiding cross contamination between patients.

Embodiments are intended to cover any positioning (and/or physical nexus) of the accelerometer relative to the patient. In some embodiments, there is no physical attachment between the accelerometer and the patient. However, in many other embodiments, the accelerometers are attached, via an attachment mechanism, directly or indirectly to the patient being monitored. Many but not all of the disclosed accelerometers are attached to a strip (or other device) for direct or indirect connection to the patient being monitored. In other words, the flexibility of the strip (or other device) of many of the embodiments is not so high that it would prevent the accelerometer from providing sufficiently accurate results, even though a certain amount of flexibility may be beneficial for other reasons.

Embodiments are intended to cover any method or apparatus for connecting the strip (or other device) to the patient, either directly or indirectly. For example, the strip (or other device) can be directly attached to the patient via adhesive, or include a mechanical attachment apparatus, such as a clip, for connection to the patient's clothing. Embodiments are also intended to cover any method or apparatus for connecting the accelerometer to the strip (or other device). For example, the strip (or other device) can define a pocket in which the accelerometer is disposed. In another embodiment, the accelerometer is disposed within a waterproof casing, such as a casing formed of synthetic resin, and the casing is attached to the strip (or other device).

The above accelerometer configurations are merely provided for exemplary purposes, and are not intended to be an exhaustive listing of all accelerometer configurations that can be used with the various inventive aspects.

III. INCLINE SENSOR MONITORING

A. Incline Summary

An explanation of patient inclines as well as a few examples of patient incline monitoring in accordance with the present disclosure are provided below. However, the following explanations are merely provided for exemplary purposes and are not intended to be an exhaustive list of patient inclines and/or applications of patient incline monitoring according to the inventive concepts of the present disclosure.

1. Patient Incline

For the purposes of at least some of the disclosed embodiments, an incline level of 0 degrees refers to a position that is parallel to the floor or other ground surface relevant to the patient. In other words, at 0 degrees, the area being measured can be referred to as "flat" and not inclined. For example, a patient in which the head, chest, pelvis, and feet are approximately equal distances from the floor would be considered "flat" and at a 0 degree incline level with respect to the floor. In this context in the present disclosure, unless otherwise indicated, all incline levels are disclosed relative to the floor, and are not disclosed relative to the hospital bed or other object. Therefore, a patient standing straight up would be considered to be at an incline level of 90 degrees, i.e., the patient's direction of extension is perpendicular to the floor surface.

Figure 12:
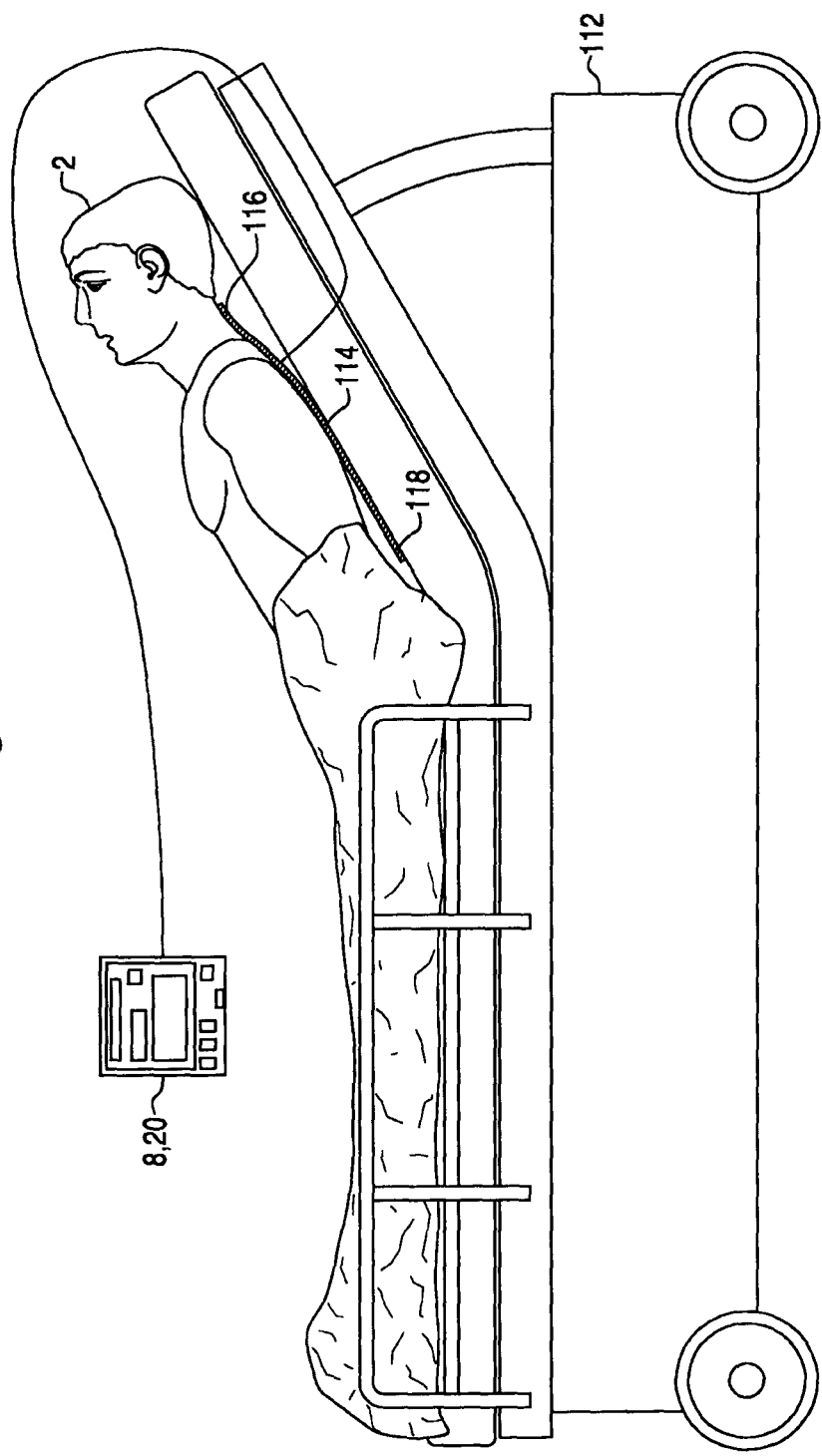
FIG. 12 is a schematic of an apparatus that includes a second exemplary embodiment of an incline sensor and attachment mechanism attached to a posterior portion of a patient to determine an angle of incline of the patient, and a second exemplary embodiment of an indicator and/or controller.

However, many of the disclosed embodiments are configured to address a patient who is in a flexed position, where some part of the patient's body is flexed, i.e., bent, relative to other parts of the patient's body. In this context, it is often relevant to monitor the incline level of a specific body part relative to a certain surface such as the floor. For example, FIG. 12 shows a patient where the lower (i.e., inferior) part of the patient's body is at a 0 degree incline, while the top (i.e., superior) part of the patient's body is at approximately a 30 degree incline with respect to the floor. In still other situations, a patient's neck may be flexed so that the head is at an incline, such as an incline of approximately at 45 degrees relative to the floor, while the rest of the patient's body (including the patient's chest) is at a 0 degree incline.

The patient positioning or orientation may be very important in certain situations, such as in the context of various types of care of hospitalized patients. In one such example, Society of Critical Care Medicine guidelines recommend a "head of bed elevation" of 30 degrees, which is designed or otherwise intended to enable or insure that the patient's stomach is closer to the floor than the mid and upper esophagus in order to use gravity to reduce, minimize or prevent the likelihood of reflux of gastric contents (e.g., tube feeds or acid) into the esophagus. Movement of these contents far enough retrograde (i.e., backward) through the esophagus can result in aspiration of these gastric contents, potentially causing lung injury, including but not limited to aspiration pneumonitis and aspiration pneumonia [e.g., often referred to as hospital acquired pneumonia (HAP) or ventilator association pneumonia (VAP)].

However, positioning or maintaining the positions of patients at orientations that are beneficial, such as pursuant to the guidelines discussed above, can be problematic. For example, in practice, a patient's head may appear to be in a sufficiently elevated position, when in fact the critical area of the chest and upper abdomen (which contain the esophagus and stomach, respectively) may actually be flat (at a 0 degree incline), thereby predisposing the patient to a higher risk of reflux of stomach contents, aspiration, etc.

In addition, as disclosed in more detail below, the level of incline of a patient's bed is often significantly different from the incline of the patient's specific body part, e.g., the upper abdomen and chest, which can be relevant in numerous contexts, such as with regard to reducing or preventing reflux and/or aspiration. For example, the "head of the bed" may be elevated 30 degrees, which is consistent with guidelines for the position of most mechanically ventilated patients, patients receiving gastric tube feeds, and/or patients with impaired mental status or ability to protect their airway. However, such patients are typically prone to sliding downward toward the foot of the bed to such an extent that they no longer comply with the above or other guidelines. For example, this sliding may result in the patient's head being inclined at 30 degrees, with the relevant body part (e.g., upper abdomen/chest area) being actually or substantially flat, i.e., at an approximately 0 degree incline. The above situation is merely provided for exemplary purposes, i.e., as one example of a patient incline issue addressed by the present disclosure, and is not intended to be an exhaustive listing of patient incline situations addressed by the various embodiments.

2. Incline Sensors

Exemplary embodiments are intended to cover any and all related art, currently known, and/or later developed technologies for sensing and/or otherwise monitoring patient incline, such as patient inclines of 10, 20, 30, 40, etc. degrees. Some of the incline sensing technologies utilized by some of the disclosed embodiments are discussed below for exemplary purposes only, and the following disclosure is not intended to be an exhaustive listing of inkling sensing technologies covered by the various inventive aspects.

Embodiments are intended to include incline sensors that utilize any type of power source. For example, the sensors of some embodiments are connected to external power sources, such as by wiring, while other sensors utilize batteries or other internal or locally disposed power sources. Some incline sensors do not require separate power sources, such as local or remote electric power sources, and can merely be attached to a patient's chest, back, neck, etc. A separate powered receiving device can access the conditions sensed by the passive power-free sensor. These power-free sensors can be advantageous for various reasons, such as by being easy to install, operate, etc. However, as discussed above, sensors included in other embodiments require separate power sources, such as local or remote electric power sources, and can be advantageous for other reasons, such as enhanced operability, accuracy, etc.

Exemplary embodiments are intended to cover incline sensors having all relevant levels of precision. The levels of precision of certain embodiments may depend on various criteria, such as the particular application of the incline sensor. For example, some criteria, such as criteria that is application based, may only require precisions of +/−2.5 or 5 degrees, while other applications may require precisions of +/−0.1 degrees. As one example, the sensor can have a relatively large tolerance, such as a precision of +/−5 degrees, if it is being used merely to monitor whether the patient has left a hospital bed. Contrarily, it may be helpful for the sensor to have a tighter tolerance, such as +/−0.5 degrees, for other applications, such as for reflux monitoring.

In addition to different precisions, exemplary embodiments are intended to include sensors including different technologies, and in some embodiments multiple different technologies, including but not limited to all accelerometer technologies. For example, some embodiments utilize technologies enabling patient inclination measurements in two-dimensional space. These embodiments are useful in determining patient inclination angle, such as confirming a patient incline of 30 degrees. Other embodiments utilize technologies to determine patient orientation in three-dimensional space. The three-dimensional embodiments may be useful in determining whether a patient is in a prohibitive position, such as an infant being face down. The three-dimensional embodiments may also be useful to detect patient movement, such a determining whether a patient who is likely to fall is walking or attempting to walk. Other embodiments utilize still other technologies, such as vibration detectors, to determine patient movement.

The disclosed incline sensors, regardless of their form or configuration, can be integrated into, or otherwise used in conjunction with, other apparatus for any useful or beneficial purpose or application. For example, the incline sensor of some embodiments transmits periodic, semi-continuous and/or continuous patient incline data to a recorder, controller, processor, and/or other device. The data transmission can be accomplished in accordance with any known, related art or later developed technique or technology, including data transmitted via wires, wirelessly, etc. Embodiments are intended to cover any relevant incline data, such as an incline measured between a patient's upper chest, e.g., sternal notch, and the patient's lower chest, e.g., xiphoid process.

Some embodiments use the incline sensor to monitor deviations in patient incline. The incline sensor of some of these embodiments transmits patient incline data to a recorder, controller, processor, or other device, for the purpose of determining whether a measured patient incline exceeds or decreases below an incline set point by a predetermined magnitude of deviation.

Some embodiments involving incline monitoring are disclosed above, such as in the context of aspiration reduction and/or prevention. However, other embodiments are not limited to these contexts, and various embodiments focus on broader and/or other applications of incline monitoring, some of which are disclosed below for exemplary purposes.

B. Chest Monitoring

The Incline Angle of a patient's chest is directly or indirectly relevant to a number of patient conditions. Monitoring this incline angle to ensure or facilitate maintenance of a proper target chest incline angle may improve or otherwise address these patient conditions. A few such patient conditions and chest incline angle monitoring techniques are discussed below for exemplary purposes only, and are not intended to be an exhaustive listing of such conditions and monitoring techniques covered by the various embodiments.

1. Patient Conditions

Numerous patient conditions are affected by the chest incline angle. Some of these conditions are discussed below for exemplary purposes. However, the various embodiments are intended to address conditions in addition to those discussed below, including currently known and later discovered conditions.

Acutely ill patients undergoing enteral feeding in hospitals are at a high risk for suffering aspiration, which can ultimately result in lung injury including pneumonia. In fact, pneumonia is the most common infection acquired during the intensive care unit (ICU) stay by patients, occurring in 9% to 40% of all patients. This statistic is confirmed in Williams Z, et al. A Simple Device to Increase rates of Compliance in Monitoring 30-Degree Head-Of-Bed Elevation in Ventilated Patients. *Crit Care Med.* 2008; 36(4):1155-1157 ("Williams"), which is hereby incorporated by reference in its entirety.

Other studies have supported the above data, including Metheny N A, et al. Tracheobronchial Aspiration of gastric Contents in Critically Ill Tube-Fed Patients: Frequency, Outcomes, and Risk Factors. *Crit Care Med.* 2006; 34(4):1007-1015 ("Metheny"), which is hereby incorporated by reference in its entirety. The Metheny study included 360 adult patients who were receiving mechanical ventilation assistance and tube feeding, and showed that 88.9% of the patients suffered at least one aspiration event in the four days each patient was studied. When the study began, no patient had pneumonia, yet on the fourth day, 48% of patients had pneumonia. Correspondingly, the most significant risk factor for pneumonia of patients in the study was aspiration. Those involved in conducting the study identified a low backrest elevation as exposing patients to a higher risk of aspiration and pneumonia.

Contracting pneumonia lengthens the time patients stay in ICU and often extends the need for ventilator support. According to the Williams study, each case of pneumonia contracted by hospital patients costs between $40,000 and $50,000, and increases mortality by 15% to 45%. With the current rate of pneumonia occurring in 5 to 35 cases per 1000 ventilator days, hospitals have an opportunity to significantly reduce mortality and costs by decreasing the incidence of pneumonia in mechanically ventilated and tube-fed patients.

Studies have shown a correlation between a higher head-of-bed elevation and a reduction in pneumonia in ventilated and tube-fed patients, including Drakulovic M B, et al. Supine Body Position as a Risk Factor for Nosocomial Pneumonia in Mechanically Ventilated Patients: A Randomized Trial. *The Lancet.* 1999; 354:1851-1858 ("Drakulovic"), which is hereby incorporated by reference in its entirety. This study focused on 86 patients and observed that patients positioned semi-recumbently at a head of bed ("HOB") elevation of 45 degrees experienced a 75% reduction in the rate of pneumonia as compared to those patients in the supine position.

Another relevant study is Alexiou V G, et al. Impact of Patient Position on the Incidence of Ventilator-Associated Pneumonia: A Meta-Analysis of Randomized Controlled Trials. *Journal of Critical Care.* 2009; 24:515-522 ("Alexiou"), which is hereby incorporated by reference in its entirety. The Alexiou study focused on three relevant randomized trials involving 337 patients. The meta-analysis confirmed previous findings and showed a statistically significant reduction in clinically diagnosed pneumonia (OR=0.47; 95% CI, 0.27-0.82).

However, compliance with the prescribed head of bed elevation can be difficult to achieve, as evidenced by Van Nieuwenhoven C A, et al. Feasibility and Effects of the Semi-recumbent Position to Prevent Ventilator-Associated Pneumonia: A Randomized Study. *Crit Care Med.* 2006; 34(2): 396-402 ("Van Nieuwenhoven"), which is hereby incorporated by reference in its entirety. This study showed that clinicians were not successful in keeping patients at the prescribed HOB elevation of 45 degrees for 85% of the time. In another example, the Williams study focused on 268 bed measurements of ICU patients, wherein an experimental device to display HOB elevation was attached to the hospital beds to discern whether it would help nurses maintain more accurate HOB elevations. Beds with the device had an average HOB elevation of 30.9 degrees, while bed measurements for those without the device showed an average of approximately 9 degrees less, at 21.8 degrees. This study suggests that the issue of HOB maintenance is due to several factors, one of which being uncertainty in the mind of the caregivers as to whether the HOB needs to be adjusted based on the lack of any definitive angle indicator.

The Williams study disclosed shortcomings in the monitoring and maintenance of HOB elevation in hospitals, but failed to identify a modern and flexible solution, and in particular a method or apparatus for measuring/monitoring the incline of the patient. This lack of disclosure is significant because the angle of the bed cannot be equated with the angle of the patient. Another study that focused on the methods of measuring HOB elevation is Hummel R, et al. Continuous Measurement of Backrest Elevation in Critical Care: A research Strategy. *Crit Care Med.* 2000; 28(7):2621-2625 ("Hummel"), which is hereby incorporated by reference in its entirety. The Hummel experimenters implemented a method of attaching transducers to the bed to continuously monitor ICU beds and thereby provide display angles similar to the Williams study. While this measurement technique could be used for continuous measurement for research or for continuous monitoring of patients, the researchers admitted that it is limited by the assumption that the patient is positioned at the same angle as the bed.

Another such study is Balonov K, et al. A novel Method of Continuous Measurement of Head of Bed Elevation in Ventilated Patients. *Intensive Care Med.* 2007; 33:1050-1054 ("Balonov"), which is hereby incorporated by reference in its entirety. The Balonov study further illustrated the difficulty of maintaining proper HOB elevation under current methods and practices when 29 ventilated patients were studied, and all patients were shown to have HOB elevation of less than 30 degrees over the course of three days of 24-hour studies. Further support for the above data is provided by Grap M J, et al. Effect of Backrest Elevation on the Development of Ventilator-Associated Pneumonia. *Am J Crit Care.* 2005; 14:325-332 Grap (2005) ("Grap"), which is hereby incorporated by reference in its entirety. The Grap study continuously monitored head of bed incline using transducers in 66 ICU subjects (276 pt days), and found that mean backrest elevation for the entire study period was only 21.7°, and further that backrest elevations were less than 10° 39% of the time.

Based on the above and other data, the Society of Critical Care Medicine (SCCM) and other prominent medical organizations provide clear guidelines to maintain a HOB elevation. However, in spite of the guidelines, a number of factors cause the HOB elevation of mechanically ventilated and enterally fed patients to be lower than the guidelines. First, the related art fails to provide a clear measurement on the patient incline to determine whether the bed is positioned at the correct incline, e.g. 30 or 45 degrees. Second, patients often slide down an elevated bed over time based on gravity and low friction. To reposition these patients, nurses need to first lower the bed given the difficulty in moving a patient. This regular lowering of beds for adjustment, combined with no accurate measure of bed elevation, results in a wide distribution of HOB angles. Furthermore, the related art fails to continuously record the incline of the patient in order to determine compliance with established guidelines over time. Although the Williams study indicated that the disclosed device improved compliance, it did not measure the actual patient's incline level, and importantly this device lacked any capability for electronic recording by hospital data systems, which would facilitate beneficial uses of patient incline data over time.

The related art fails to address much less solve the difficulties in effectively monitoring and then maintaining appropriate HOB elevations is an unsolved problem for ventilated and tube-fed patients, which unfortunately is quite pervasive in hospitals today, resulting in higher rates of hospital acquired pneumonia and generating additional healthcare costs. Although much of the focus of the above studies has been in ICU patients, an unmet need also arises in other settings, such as non-ICU hospital wards for patients at risk for aspiration of gastric contents including those being enterally fed and/or with poor mental status or dysphagia. Similarly, high risk patients are also found in other settings, such as nursing homes and rehabilitation facilities for patients after stroke, trauma, surgery, or other conditions. However, the above listing of potentially beneficial recipients of incline monitoring is merely provided for exemplary purposes, and not intended as an exhaustive listing.

2. Monitoring a. Overall Structure(s)

Exemplary embodiments are intended to cover or otherwise include any structure to implement the chest incline monitoring discussed below, including but not limited to the structures disclosed in Section X (Exemplary Sensor Structure(s)) of the present disclosure.

Some embodiments only include a sensor directly or indirectly attached to a patient, such as to a patient's chest. In some such embodiments, the sensor itself and/or the sensor housing includes an indicator providing an indication of the current incline and/or a log or history of past inclines. Further, in some of these embodiments, the sensor itself and/or the sensor housing includes other devices/apparatus for providing other functionalities, including but not limited to an indicator providing an indication of deviation from a certain incline setpoint or setpoints, such as in the form of an auditory and/or visual alarm.

Some embodiments include other devices or apparatus in addition to the sensor and/or sensor housing, such as in the form of an incline sensor system. In one such embodiment, a recorder, controller, processor, or other device, structurally or functionally in communication with the sensor, provides an indication to a user of the patient's current incline angle. In some of these embodiments, the recorder, controller, processor, or other device provides a log or history of past inclines. In some of these embodiments, the recorder, controller, processor, or other device provides other functionalities, including but not limited to providing an indication of deviation from a certain incline setpoint or setpoints, i.e., determining whether the measured patient chest incline exceeds or decreases below the incline setpoint by a predetermined angle, such as in the form of an auditory and/or visual alarm.

The sensor and sensor system operations can be implemented using any currently known, related art, or later developed technologies. For example, actuation of any or all of the operations, such as various settings, can be performed in any relevant or beneficial manner using currently known or later developed technologies, including but not limited to buttons, touch screen displays, etc.

The chest incline sensors and/or sensor systems can be used with or integrated into other types of apparatus, such as other types of monitoring apparatus and/or diagnostic type apparatus. In some embodiments, the sensors and/or sensor systems are used with or integrated into apparatus related to patient conditions that are related or relevant to patient inclines.

For example, as disclosed above, it is common for patients lying in inclined hospital beds to slide down, which prevents a desired portion of the patient's body (such as the patient's chest) from being maintained at a certain desired incline angle. Thus, the incline sensors and sensor systems can be used in conjunction with or incorporated into apparatus for reducing or preventing patients from sliding down inclined hospital beds.

In some embodiments, chest incline measurements can be used to indicate unwanted patient sliding so that patients can be moved to hospital beds equipped with apparatus for reducing or preventing patients from sliding down inclined hospital beds, such as a platform extending generally perpendicular to the bed surface at the foot of the bed for contacting the bottom of the patient's feet to thereby prevent patient sliding. In other embodiments, upon detecting prohibited patient sliding, the chest incline sensors and sensor systems are used to activate mechanisms for reducing or preventing further sliding and/or automatically to place the patient back at the appropriate incline angle. For example, the chest incline sensors and sensor systems can send a control signal to activate a platform to extend from the bed to contact the bottom of the patient's feet to thereby reduce or prevent further patient sliding, and/or send a control signal to change the bed inclination to place appropriate portions of the patient's body at the desired incline.

b. Setpoint and Threshold Functionalities

A few exemplary functionalities or operations of the above apparatus are discussed below for exemplary purposes only, and are not intended as an exhaustive listing of chest incline measurement operations performed by the various embodiments. In fact, the various embodiments are intended to include any beneficial or otherwise useful functionality associated directly or indirectly with chest incline angle measurement.

i. Deviating from Setpoint by Predetermined Amount

As discussed above with regard to monitoring structure(s), some embodiments provide an indication of deviation from a certain incline setpoint or setpoints, i.e., determining whether the measured patient chest incline exceeds or decreases below the incline setpoint by a predetermined angle. In one example, if the incline setpoint is 30 degrees, and the predetermined magnitude of deviation is 10 degrees, then the sensor and/or sensor system will provide an alarm or other type of indication upon receipt of data indicating that the sensor has measured a patient incline angle that is less than 20 degrees and/or greater than 40 degrees.

Other embodiments cover subsets and/or variations from the above functionality. For example, some embodiments provide the alarm/indication only if the measured patient chest incline is less than the incline setpoint by an amount exceeding a predetermined magnitude. Other embodiments provide the alarm/indication only if the measured patient chest incline is greater than the incline setpoint by an amount exceeding the predetermined magnitude. Still other embodiments, such as the example provided in the preceding paragraph, provide the alarm/indication if the measured patient chest incline is either greater than or less than the incline setpoint by an amount exceeding the predetermined magnitude.

ii. Deviating from Chest Incline Threshold

Other embodiments monitor deviations in patient incline differently than the above embodiments that determine whether a measured patient chest incline deviates from a chest incline setpoint by a certain magnitude. For example, some embodiments monitor whether a measured patient incline is less than or greater than a certain patient chest incline threshold. For example, as currently recommended by SCCM/ASPEN, it may be beneficial for the angle of inclination of certain patients, such as those at risk of reflux, to maintain an angle of incline of at least 30 degrees, i.e., 30 degrees or more. In these exemplary embodiments, the sensor and/or sensor system would provide an alarm/indication upon receipt of data indicating that the sensor has measured a patient chest incline angle that is less than 30 degrees.

The above exemplary embodiment is particularly applicable for patients at risk for aspiration of gastric contents, e.g., gastric secretions and/or tube feeds, where it is beneficial for the patient's upper chest to be inclined by at least 30 degrees relative to the patient's abdomen. This procedure uses gravity to reduce, minimize and/or prevent columnar reflux of gastric contents.

Exemplary embodiments are intended to apply the above procedure in any beneficial context. For example, this procedure may be beneficial for ICU patients as well as other at risk patients, such as those in a step down unit, hospital ward, nursing home, rehabilitation center, or long term care facility. Patients at increased risk may include, but are not limited to: 1) patients with a history of aspiration; 2) patients at increased risk for aspiration, e.g., history of dysphagia or receiving enteral tube feeds, such as gastric or post-pyloric feeding; 3) ICU patients paralyzed with a neuromuscular blocker to facilitate their care, e.g., mechanical ventilation in extreme hypoxemia; 4) patients with a history of stroke or other neurological condition which could impair ability to protect their airway, e.g., cough, swallow, etc.; and/or 5) patients with decreased mental status due to drugs (e.g., sedatives, narcotics) or due to an underlying condition, e.g., head injury, stroke, or coma that may also impair the ability to protect the patient's airway.

However, the above 30 degree patient incline threshold is merely provided for exemplary purposes, and other embodiments can use multiple and/or different thresholds. In fact, the sensor and/or sensor system of some embodiments can be operated to change the threshold under certain circumstances, for certain patient(s), etc. For example, it may be desirable for the incline threshold for some patients to be 45 degrees, such that the sensor and/or sensor system would not provide an alarm/indication until receiving data indicating that the sensor has measured a patient chest incline angle that is less than 45 degrees.

c. Measurement Frequency

In some embodiments, the frequency of chest incline measurements is preset, such as every one minute. Thus, in these embodiments, the sensor and/or sensor system measures the patient chest incline every one minute.

However, other embodiments vary the frequency of chest incline measurements. In one such embodiment, a change in the patient's condition changes the frequency of subsequent measurements. In some of these embodiments, if the chest incline angle is within normal or substantially normal parameters, then an operation can be performed wherein the chest incline angle is measured less frequently, such as only once every ten minutes, which may be beneficial for various reasons, such as to enhance, improve, or even optimize battery life.

In one such embodiment, the sensor, such as an accelerometer, only performs the chest incline measurement operation once every ten minutes, if the immediately previously measured chest incline angle was within normal parameters. In some of these embodiments, a processor cooperates with an accelerometer to trigger the accelerometer to perform the chest incline measurement only once every 10 minutes. However, if the measured chest incline is concerning (e.g., a measurement of 10 degrees if a 30 degree chest incline is prescribed), then the processor increases the rate of measurement, such as once every one or two minutes. A significant acceleration of the patient, as would be observed by a patient moving from the sitting to the standing position, could similarly trigger an increase in the rate of subsequent measurements.

However, the above examples of measuring frequency are provided for exemplary purposes, and are not intended as limiting. In fact, embodiments are intended to cover any frequencies of measurement that are beneficial or useful.

In another embodiment, a processor that is incorporated into, or otherwise in communication with, the sensor or sensor system can use additional information to change the frequency of measurements. For example, if data is obtained that indicates an increased risk of occurrence of an unwanted condition, such as a dangerous condition, then the chest incline can be measured relatively more frequently. This operation may be beneficial because the increased data obtained by the relatively more frequent chest incline measurements may be used to avoid, prevent or reduce the impact of the unwanted or potentially dangerous condition. Contrarily, if data is obtained that indicates a decreased risk of occurrence of an unwanted or dangerous condition, then the chest incline can be measured relatively less frequently. This operation may be beneficial for other reasons, such as to conserve battery life or increase longevity of the sensor or sensor system.

For example, the processor can take into account several factors that may predict whether a patient is likely to be sleeping or heavily sedated, e.g., late at night, such as at 2 a.m. In this condition, the patient's heart rate and respiratory rates slow, such as 10% lower than the median value obtained during day time, and the patient is subject to minimal movement as is consistent with sleep. In such a condition, the frequency of measurements of the patient chest incline can be reduced, such as every 15 minutes, in order to conserve battery life, enhance sensor longevity, etc. Subsequent detection of increased patient movement and increases in heart rate and/or respiratory rate may suggest that the patient is now awake, warranting more frequent chest incline measurements, because an awake patient may be more likely to move into an incorrect position. In this example, external factors, such as the time of day, or even manual input of data by caregivers may provide data that is helpful to determine whether more or less frequent measurements would be needed or otherwise beneficial.

d. Indicator(s) and/or Alarm(s)

Embodiments are intended to include or otherwise cover any beneficial or useful apparatus and/or method for performing an indication or alarm relating to the patient conditions disclosed herein, incorporating known, related art, and/or later developed technologies. For example, embodiments are intended to utilize any medium for providing the indication/alarm, including but not limited to the following mediums that are perceivable or otherwise recognizable to a user, such as a caregiver: visual, audible, vibration, etc. In fact, some embodiments are not limited to providing indications(s)/alarm(s) in a medium that is perceivable or otherwise recognizable to a human user. For example, some of these embodiments provide indication(s)/alarm(s) to a machine, such as a hardware processor. Some embodiments also utilize multiple mediums for providing the indication/alarm either concurrently, sequentially, and/or selectively.

Embodiments are also intended to include or otherwise cover any beneficial or useful functionalities or operations associated (directly or indirectly) with performing an indication or alarm relating to relevant patient conditions. These embodiments are intended to incorporate known, related art, and/or later developed technologies. A few such functionalities/operations are discussed below for exemplary purposes only, and are not intended to be an exhaustive listing of all functionalities included in or performed by the embodiments.

Some embodiments immediately provide an indication/alarm upon occurrence of an alarm condition, such as immediately upon receipt of data indicating that a patient's chest incline angle falls below a certain threshold angle, such as 30 degrees. These embodiments may be beneficial in numerous situations, such as those where it may be immediately disadvantageous for a patient to adopt a certain orientation, such as the patient's chest falling below the 30 degree elevation.

However, other embodiments do not immediately provide the indication/alarm upon occurrence of an alarm condition or immediately following a single alarm condition. For example, some embodiments delay providing the indication/alarm until after occurrence of the alarm condition, or only provide the indication/alarm after occurrence of multiple alarm conditions. Some of these embodiments may be beneficial by reducing, minimizing or even preventing alarms of limited utility, or unnecessary alarms that can contribute to "alarm fatigue" present in some settings, such as an ICU.

In some of these embodiments, an indication/alarm is only provided after a patient remains at an elevation angle below a set threshold for a certain amount of time, rather than as soon as the patient's HOB angle drops below the threshold. For example, in one embodiment, an indication/alarm is only provided after the patient has been in an undesirable position or orientation for a period, such as more than one minute. These embodiments may be especially beneficial to avoid the indication/alarm in certain situations, such as where minimal or no disadvantageous effects occur if the patient assumes an undesirable position or orientation for a limited time. For example, this situation may apply if a caregiver needs to reorient a patient for a limited period for a certain reason, e.g., where a caregiver needs to flatten a patient's bed for a period less than one minute, such as 30 seconds, to pull the patient up in the bed or for some other reason.

In some embodiments, the medium or type of indication/alarm is preset, such that a certain preset medium and/or type of indication/alarm is provided upon occurrence of the indication/alarm condition. For example, in one such embodiment, the indication/alarm is always provided in the form of a beeping sound upon the occurrence of the alarm condition.

Contrarily, other embodiments enable a user to select the medium or type of indication/alarm that is provided upon occurrence of the indication/alarm condition. For example, in one such embodiment, the user can set the indication/alarm to be a flashing light. In other words, the indication/alarm feature can be customized so that users, such as clinicians, can chose, for example, no alarm, audible alarm only (with options for magnitude of the alarm sound/volume), visual alarm only, or a combination of an audio and visual alarm. In some ICUs, it may be desirable to use the visual alarm only (e.g., blinking red symbol on the monitor), which can catch the attention of the caregiver, e.g., nurse, but not promote "alarm fatigue." However, the above customizations are merely provided for exemplary purposes, and embodiments are intended to cover any such customizations of the medium or type of indication/alarm that are beneficial or otherwise useful/relevant.

In other embodiments, different mediums or types of indications/alarms can be provided to correspond to different indication/alarm conditions. In some of these embodiments, the indications/alarms are tiered so that occurrence of one condition results in a visual indication/alarm only, while another, possibly more serious condition, results instead or an additional audio indication/alarm. In one example, if the prescribed angle of patient chest incline is 30 degrees, then the visual alarm may be triggered by chest inclines of 20-29 degrees, with the addition of an audio alarm if the chest incline drops below 20 degrees, indicating a more serious/risky condition. In another embodiment, a visual alarm is provided upon occurrence of an incorrect patient incline, while an audio alarm is provided upon detection that the patient is attempting to stand or is already standing. This feature may be especially relevant in certain situations, such as ICUs, because unsupervised standing ICU patients are at greater risk for falls and other injury, e.g., pulling out intravenous, arterial, and/or urinary catheters. However, the above customizations are merely provided for exemplary purposes, and embodiments are intended to cover any other customizations that are beneficial or otherwise useful/relevant.

Other embodiments enable customization of the recipient of the indication/alarm. In other words, some embodiments enable the operator to determine the recipient of the indication/alarm. For example, at least one of a patient, nurse, nurse's station, doctor, centralized monitoring area, etc., can be designated to receive the indication/alarm. It may be beneficial to vary the recipient of the indication/alarm condition depending on circumstances. For example, it may be beneficial to provide the indication/alarm directly to the patient if the chest incline varies slightly from a preset level to prompt the patient to change position/orientation without requiring participation by a caregiver. These embodiments are beneficial by alerting the patient to change orientation/position as soon as possible.

In fact, some embodiments vary the recipient of the indication/alarm based on the type of condition or other criteria. For example, the patient may receive the indication/alarm for conditions that are not immediately serious/dangerous, while a nurse may receive the indication/alarm for conditions that may be more immediately serious/dangerous.

In some embodiments, the indications/alarms that are directed to the patient are in the form of verbal messages, some of which may be tailored to provide the patient with instructions. These embodiments may be beneficial because it obviates or at least reduces the amount of training required for the patient. For example, if it appears that the patient is attempting to get out of bed and stand, based on a significant acceleration in the vertical axis, an audible message from the sensor/system can be provided, e.g., "It seems like you are trying to get up. Please stay down and call for assistance."

Embodiments are intended to cover any variation of the above message(s) that may be beneficial or useful. For example, a menu (accessible by the caregiver, patient, etc.) may be provided that includes multiple suggested statements, e.g., "Please sit down", or "Do not stand up", in male or female voices, or in different languages (e.g., English, Spanish, etc.). A specific message may also be recorded, such as by the caregiver, or specific default messages can be selected.

Some embodiments tier the above audio messages based on relevant criteria, such as perceived patient risk. For example, upon detection of intermittent small vertical accelerations consistent with a debilitated patient attempting to get out of bed or a chair, the following message may be provided: "Please do not get up now." Upon detection or receipt of data reflecting a very large horizontal and/or vertical acceleration, consistent with the patient having stood up, or even walking, then the a louder of higher volume message can be provided that is otherwise more severe, e.g., "STOP—DO NOT MOVE—WAIT FOR ASSISTANCE."

The sensor/system can include inputs, such as for use by the caregiver, to pause any or all of the above patient directed indications/alarms. For example, a caregiver, nurse, physical therapist, doctor, etc., can pause/override all alarms for a certain period, such as 15 minutes, for any relevant reason. These embodiments may be beneficial in situations where the caregiver needs to move or otherwise manipulate the patient.

The above patient targeted alarms are particularly useful in settings where the caregiver may not be with the patient all of the time, e.g., in an ICU with 1:2 nursing, where one nurse cares for 2 patients in different ICU rooms; or on a hospital ward of nursing or rehabilitation facility where a nurse or other caregiver supervises multiple, e.g., 10-20 patients, at the same time. However, embodiments that include patient directed indications/alarms are not limited to the above situations, and are applicable in other scenarios, such as for use in a patient's home without a caregiver.

In other embodiments, the indications/alarms are directed to the caregiver, such as a doctor, nurse, therapist, etc. For example, if it appears that the patient is attempting to stand up based on a significant acceleration in the vertical axis, an indication/alarm can be provided, either locally (by the bedside monitor) or centrally (e.g., nursing or similar station). This indication can be communicated to any other location or individual that may be useful using known, related art, or later developed technologies, such as via wires or wirelessly. Embodiments are intended to cover or include any medium or type of indication/alarm, such as audible and/or visual (e.g., blinking red light).

Alternatively, or in addition, the indication/alarm provided to the caregiver can be in the form of verbal messages, some of which may be tailored to provide the caregiver with instructions. In some embodiments, the indication/alarm is in the form of a message that is transmitted or otherwise communicated to a pager or other telecommunications device. This message can include any information that is useful, such as information indicating that the patient is in a certain position/orientation/condition.

The above indications/alarms can be used to indicate any patient condition that is useful, including but not limited to patient chest incline or position, patient movement, e.g., attempts to stand or walk, and/or potentially serious changes in vital signs. Exemplary vital signs that may be monitored include heart rate, and in particular whether the heart rate drops to less than a default value, e.g., 40 beats per minute, or respiratory rate, and in particular whether the respiratory rate is less than a default value, e.g., 6 breaths per minute. The above and other indication/alarm parameters or limits can be customized based on various criteria, such as the institution as well as patient characteristics.

As another example, some embodiments include sensors that monitor various patient conditions or data that are necessary to determine whether the patient is subject to or suffering from a certain condition. The sensor or sensor system van include a processor that uses algorithms to determine whether the patient is subject to or suffering from this condition based on the data received. If this condition is determined to exist, an appropriate indication/alarm can be communicated to a caregiver. For example, if there is evidence of pulmonary edema (detected by inspiratory crackles/rales), or bronchospasm (high frequency expiratory sounds consistent with wheezing), an indication/alert can be provided to the caregiver in any form that effectively or accurately communicates the condition, such as in the form of a verbal message. These embodiments may be beneficial by providing caregivers with early warning of a new or worsening condition. Indication/alarm thresholds can also be graded based on the trend of sensed conditions. Specific sensed conditions may initiate additional one time and periodic measurements to better determine the patient's condition. As one example, a low respiratory rate below 15 may initiate more frequent measurements, such as respiration rate, respiration depth, heart rate, and other exemplary measurements, to monitor the patient more closely and determine if the condition changes. If the subsequent measurements indicate the patient condition is improving, the frequency and type of measurements may be decreased to conserve battery life. Alternatively, if the subsequent measurements indicate the patient condition is not improving, in one exemplary embodiment the device may initiate a command to interact directly with the patient. As one example, the device may initiate a verbal message or loud buzzer to wake the patient in an effort to increase breathing or otherwise improve their condition. In another example, the device may initiate an electric shock, vibration, or other type of stimulation to wake the patient to increase breathing or otherwise improve their condition.

The sensor/system can include, or otherwise cooperate with, apparatus not directly related to, or even unrelated to, providing an indication/alarm. For example, in some embodiments, the sensor/system includes, or otherwise cooperates with, a light disposed locally relative to the patient, such as in the patient's room, that illuminates the room upon occurrence of a certain condition, such as the patient attempting to get out of bed. This light may be especially beneficial at night in an otherwise relatively dark environment where it would be dangerous for a debilitated patient to attempt to stand or walk without assistance.

e. Monitoring/Recording Inclines Over Time

Some embodiments use the patient chest incline sensor or sensor system to monitor deviations in patient chest incline for reasons other than those discussed above. The incline sensor of some of these embodiments transmits patient incline data to a recorder, controller, processor, or other device, for the purpose of showing or otherwise indicating a trend in degree of incline over time. One such embodiment enables the indication of patient incline data over various periods. For example, in this embodiment, an operator can indicate the patient incline data over a first period (e.g., over one hour), over a second period (e.g., over 6 hours), over a third period (e.g., over 12 hours), over a fourth period (e.g., over 24 hours), etc.

The above periods are merely provided for exemplary purposes, and embodiments are intended to provide for the indication of any period that is relevant or potentially beneficial. Exemplary embodiments are also intended to cover any relevant currently known or later developed technology or method of indicating the patient chest incline data. In some embodiments, the patient chest incline data is shown visually, such as via a graph, with time representing one axis and patient chest incline angle representing the other axis.

In another embodiment, more than one deviation in position is monitored, and an indication/alarm is provided to indicate occurrence of the requisite deviations in positions. For example, for a patient being enterally fed into the stomach, an indication/alarm may provide an indication as to whether the incline of the upper chest/abdomen is less than 30 degrees, or approximately 30 degrees, such as +/−5 degrees, for example, relative to the floor. Alternatively, or in addition to the above, an indication/alarm may provide an indication as to whether the upper chest/abdomen is greater than 75 degrees, or approximately 75 degrees, such as +/−5 degrees, which may indicate that the patient is attempting to sit up, stand and/or possibly leave the hospital bed, which could predispose the patient to injury. In yet another embodiment, a recorder, monitor, or other device provides different types of indications, such as different sounds, to enable medical care providers, such as clinicians, to quickly and/or easily differentiate one type of patient condition deviation from another type.

Still other embodiments include or otherwise utilize any relevant or beneficial use or manipulation of the patient chest incline data. For example, some embodiments generate and/or supply a report of patient incline data as a function of certain parameters. One such embodiment generates and supplies a report indicating a percentage of time in which the patient chest incline angle is less than a certain angle (e.g., 30 degrees) over a certain period (e.g., over 24 hours). Other embodiments provide a report indicating a percentage of time in which the patient chest incline angle is greater than a certain angle (e.g., 45 degrees) over a certain period (e.g., over 6 hours). However, the above manipulations and/or uses of data are merely provided for exemplary purposes, and embodiments are intended to cover any relevant or beneficial use or manipulation of the patient chest incline data.

Some embodiments include other alternative or additional functions or operations. For example, some embodiments include a pause feature that temporarily interrupts monitoring, tracking, etc., of the patient chest incline data. This interruption can be performed in any manner, such as by interruption of the transmission of the patient chest incline data to the recorder, controller, processor, or other device. As an alternative, the interruption can by performed by the recorder, controller, processor, or other device.

The pause/interruption feature disclosed above can be beneficial for a variety of reasons. For example, this feature may enable a medical care provider, such as a doctor, nurse, physical therapist, etc., to interrupt patient incline monitoring during events where the monitoring is not relevant or would lead to ambiguous or erroneous results. In one example, the medical care provider may interrupt or otherwise disable the patient incline monitoring during a temporary period where the patient: 1) needs to be moved, such as during physical therapy, 2) is removed from a hospital bed, 3) is placed in a horizontal position to perform a certain procedure, etc. The patient chest incline monitoring can then be resumed after termination of the temporary period.

In some embodiments, the recorder, controller, processor, or other device can be pre-set to perform some or all of the above operations. In one such embodiment, the recorder, controller, processor, or other device has multiple settings to perform some of the above operations. For example, a first setting can help ensure that the patient remains in an inclined position, i.e., provides an indication if the patient's chest incline angle falls below a certain amount, such as 30 degrees. The first setting may be relevant during enteral feeding. A second setting can help ensure that the patient remains in a flat, supine and/or horizontal position, and that patient's chest is not inclined. The second setting may be relevant for certain types of neurological patients. A third setting may be the pause/interruption feature disclosed above. However, the above settings are merely provided for exemplary purposes, and embodiments are intended to cover or otherwise include any such settings that may be beneficial or otherwise useful.

f. Other Applications

Embodiments are intended to cover or otherwise include any other beneficial use or application of the patient chest incline monitoring data discussed above. A few other exemplary applications of the data are discussed below for exemplary purposes, and are not intended as an exhaustive listing of other such applications.

Some embodiments use the patient chest incline monitoring for some neurosurgical patients or other patients at risk for brain ischemia requiring elevation of the head of the bed to decrease intracranial pressure (ICP). Many patients are at increased risk of brain damage due to brain ischemia, e.g., after head trauma, neurosurgery, ischemic or hemorrhagic stroke. In many of these patients, it is desirable to enhance, improve or even optimize perfusion pressure to the brain, which can be characterized as systemic mean arterial pressure minus ICP. Lowering of ICP increases perfusion pressure, which enhances, improves or even optimizes the delivery of cerebral blood flow and oxygen to brain cells. Lowering of ICP can also be relevant in conditions with significant brain swelling.

Thus, current guidelines recommend HOB elevation of at least 30 degrees in many patients, e.g., in a neuro ICU or trauma ICU. In some very high risk patients, the magnitude of head of bed elevation is changed (titrated) depending on direct measurements of ICP, e.g., intracranial pressure transducer. For example, 30 degrees HOB elevation may be increased to 45 degrees if ICP is not sufficiently low.

Some embodiments therefore include patient chest incline sensor(s) or sensor system(s) over time, such as continuously or semicontinuously, to monitor the patient's chest incline to determine whether the patient needs to be kept semirecumbent for the purpose of reducing ICP. As discussed above, some of the disclosed sensor(s) and sensor system(s) are beneficial because they measure the chest incline of the actual patient rather than the bed, which is merely a surrogate and sometimes a misleading surrogate for the patient's actual position/orientation. In addition, some of the disclosed sensor(s) and system(s) allow for electronic capture of these critical data for beneficial uses, such as by hospital data record systems. This data can be used for any beneficial purpose, such as to insure compliance with existing guidelines, enhance or improve care through analyses of these data as it relates to factors that influence patient outcome, etc.

As another example, it may be beneficial to monitor patient chest incline to determine whether the angle of incline exceeds a threshold lower than 45 degrees, such as 0 degrees or 5 degrees, for certain patients. For example, some patients need to remain in a horizontal or nearly horizontal position due to medical or surgical issues, such as patients with a cerebrospinal fluid leak in which it is desirable for the position to be supine, i.e., no elevation of the head of the bed. In another example, it is generally desirable to maintain patients with spinal cord injury in a supine position. Regardless of the medical indication for a supine position, some embodiments enable the settings to be changed to provide an indication/alarm if the patient's chest incline increases above 0 or 5 degrees.

C. Extremity Monitoring

Embodiments are intended to include sensor(s) and/or sensor system(s) that monitor inclines, orientations, positions, and/or movements of parts of a patient's body other than the chest, such as the patient's extremities, including but not limited to the patient's leg(s), feet, toe(s), arm(s), hand(s), finger(s), hip(s), etc. In fact, some and/or all of the monitoring apparatus, techniques, applications, etc., disclosed above in the context of a patient's chest can be applied in the context of a patient's extremities. Some of these applications for a patient's extremities are disclosed below for exemplary purposes, and are not intended as an exhaustive listing of such applications.

As one example, it is often desirable for a patient's leg to be elevated, such as after an orthopedic injury. In some of these situations, the incline angle of most of the patient's body is not relevant to treatment for orthopedic injuries, while in other situations it is beneficial for most of the patient's body, such as the patient's chest and/or abdomen, to be "flat." Importantly, it is often relevant or important for treatment of these injuries for the patient's leg to be inclined relative to the floor, and this incline maintained for a specified period.

Thus, some embodiments monitor or otherwise measure the level of incline of the patient's leg relative to the floor. Embodiments are intended to cover or otherwise include any apparatus and/or method for performing these measurements, including but not limited to attaching any of the sensor(s) and/or sensor system(s), disclosed above in the context of chest monitoring, to the patient's leg and/or to any other part of the patient's body to enable measurement and/or monitoring of the leg incline angle.

Some embodiments do not focus on the incline angle of a patient's extremity relative to the floor. For example, in some embodiments that focus on a patient's extremities, it may be desirable to measure the level of incline of one part of the body with respect to another part of the body, rather than relative to the floor. For example, in some situations, it may be desirable for there to be no flexion at the level of the hip. In such a case, one sensor can be attached to the patient's abdomen, and another sensor can be attached to the patient's upper leg. These two sensors can perform measurements in order to determine the angle defined by these body parts. In the above example, it would be desirable for this angle to be as close to 0 degrees as possible.

In another example, it may be desirable to maintain the leg in an elevated position relative to the patient's torso. In this scenario, sensors can be attached to both the patient's leg and torso, perform measurements in order to determine the angle defined by these body parts. However, the above scenarios are merely provided for exemplary purposes, and embodiments are intended to cover measuring incline angles between any parts of a patient's body that are beneficial or otherwise useful.

Some other embodiments do not focus on the incline angle of a patient's extremity relative to the floor or another body part, and instead focus on the incline angle of a patient's extremity relative to something else. For example, in some embodiments that focus on a patient's extremities, it may be desirable to measure the level of incline of a body part relative to a hospital bed. In some such cases, it may be desirable for there to be a 45 degree elevation of a patient's leg relative to the hospital bed. In this case, one sensor can be attached to the patient's leg and another sensor attached to the lower part of the patient's bed, e.g., toward the foot end of the bed. These two sensors can perform measurements in order to determine the angle defined between the patient's leg and the bed. In this example, it would be desirable for the angle to be as close to 45 degrees as possible. However, the above scenario is merely provided for exemplary purposes, and embodiments are intended to cover measuring incline angles between a patient's extremity and anything else that may beneficial or otherwise useful.

Other embodiments are not directed to determining incline angles between patients' extremities and something else, and instead focus directly or indirectly on movement of the extremity. Some of these embodiments specifically focus on determining whether the extremity has moved, especially in situations where immobility of the patient's extremity is desirable. For example, after surgery or other injury, there may be significant swelling of a patient's lower extremity for which leg elevation and/or leg immobility is prescribed. Another example is discussed in Bos G D, et al. Lower-Extremity Local Flaps. *J Am Acad Orthop Surg*. November 1994; 2(6):342-351 ("Bos"), which is hereby incorporated by reference in its entirety. As confirmed in Bos, surgery to create a flap in the lower extremity may necessitate a period of immobility in order to reduce or even minimize disruption of the flap or its blood flow. In these settings, the capability of sensing movement and/or decrease in leg elevation may be critical to the patient's recovery.

Thus, some embodiments include a sensor and/or sensor system for monitoring movement of a patient's extremity, and in particular, for determining whether the extremity that had been immobile has moved or is moving. As discussed above, any and all of the methods and apparatus discussed above in the context of chest inclines are applicable to monitoring movement of a patient's extremity, including but not limited to those methods and apparatus relating to mediums or types of indications/alarms, recipients thereof, etc.

D. Neck Monitoring

Embodiments are intended to include sensor(s) and/or sensor system(s) that monitor inclines, orientations, positions, and/or movements of parts of a patient's body other than the chest and extremities discussed above, such as the patient's neck. In fact, embodiments are intended to cover monitoring of positions and/or orientations of any part of a patient's body that is beneficial or otherwise useful. Some and/or all of the monitoring apparatus, techniques, applications, etc., disclosed above in the context of a patient's chest and extremities can be applied in the context of monitoring any part of a patient's body, such as the patient's neck. Some applications for a patient's neck are disclosed below for exemplary purposes, and are not intended as an exhaustive listing of such applications.

In some situations, it is desirable to ensure or otherwise maintain immobility of a patient's head/neck region, and/or ensure or otherwise maintain a certain prescribed position/ orientation of the head/neck relative to the torso. A "cervical collar" is often used in these patients. However, this collar may provide for suboptimal splinting of the neck region, such as may be the case if it is or becomes too loose. This situation can lead in some cases to injury, e.g., of the spinal cord, with disastrous sequellae in some patients.

Thus, some embodiments include sensor(s) and/or sensor system(s) that measure and/or otherwise monitor the position, orientation, and/or incline angle of a patient's neck relative to something else, such as the floor, bed, patient's torso, etc. For embodiments that measure the patient's neck incline relative to the floor, it may only be necessary to attach a sensor or multiple sensors to the patient's neck or to the vicinity thereof. Other embodiments that measure the patient's neck incline relative to something else, such as the patient's bed or another part of the patient's body, may attach sensor(s) to the patient's neck as well as to the other object, i.e., the patient's bed or other body part.

As discussed above, embodiments for monitoring neck inclines are intended to include any and all sensors disclosed above in the context of a patient's chest and extremities. However, embodiments are also intended to include sensors having structure(s) that specifically facilitate measuring neck incline, position, and/or orientation monitoring. For example, the sensor and/or attachment mechanism can be customized or otherwise include a structure specifically directed to placement directly on the neck (e.g., with adhesive). In some other embodiments, the sensor is structured to attach to, or otherwise cooperate with, other apparatus disposed in the vicinity of a patient's neck. For example, in some embodiments, the sensor is disposed in an aperture, such as a slot or channel, defined in a cervical collar worn by a patient.

Some of the above embodiments are disclosed in the context of measuring neck incline, position, and/or orientation. However, embodiments are intended to apply any and all of the above apparatus and methods in the context of determining neck motion. For example, some embodiments utilize the above and other apparatus to determine neck movement, such as to monitor whether the neck has remained immobile. In one example, the sensor and/or sensor system provides an indication/alarm if the patient's neck moves at all or moves in a certain way.

IV. FALL PREVENTION MONITORING

The apparatus and methods disclosed above can also be applied in the context of fall prevention, and monitoring events and conditions relevant thereto. For example, some embodiments include a sensor, such as an accelerometer, to detect types of movement that may be indicative of behavior that is likely to result in a person, such as a patient, falling. For example, an accelerometer can be attached, directly or indirectly, to a patient to detect angle of incline and types of movement indicative of the patient leaving the patient's resting area, such as the patient's bed, chair, etc. In other words, the sensor(s) can be used to determine whether a patient is in an erect position consistent with standing and is attempting to ambulate (move around), which may be especially beneficial in situations where such movement is likely to result in the patient falling or otherwise injuring himself or herself.

Embodiments are intended to cover or otherwise include any beneficial use or application of the data obtained by the sensor(s) and/or monitoring discussed above. For example, some embodiments communicate this data to a caregiver, such as a medical care provider, nurse, clinician, etc., indicating that a certain patient is attempting to get out of the patient's resting place, i.e., bed, chair, etc. This can be a frequent occurrence for many patients, and especially unrestrained patients, and can result in serious patient injury, e.g., injury due to a fall and/or loss of important tubes or monitors, e.g., endotracheal tube, central line, due to the patient attempting to get up, stand, and/or walk. Communicating this information to the caregiver may enable the caregiver, or someone else, to intervene and prevent the patient from falling or otherwise injuring himself or herself.

Communicating this information may be especially useful in a hospital ward or other care facility where one, or a relatively small number of, caregivers are providing care for a relatively large number of patients. This may especially be the case at night where one hospital ward nurse may be responsible for twenty or more patients. Thus, some embodiments monitor several or all such patients as disclosed above, and communicate or otherwise transmit the relevant data to the nurse or central station (e.g., nurses' station). Communicating this data can thereby alert the caregiver to a situation where a patient is attempting to ambulate, leave their room or hospital ward, etc.

However, embodiments are intended to include sensor(s) and sensor system(s) that communicate this data to anyone or anything to provide beneficial results. For example, the data may be communicated to the patient to remind the patient not to leave the patient's resting place, such as the bed, chair, etc., without assistance. Alternatively, or in addition to the above, the data may be communicated to a machine, such as a processor, for performance of some beneficial operation, such as alerting certain individuals of the situation.

Embodiments are intended to include any method and/or apparatus for making the determinations discussed above. For example, some embodiments provide an indication/alarm if the patient's incline increases to above a certain threshold, such as 75 degrees, which would occur if a patient is standing or attempting to stand. In other exemplary embodiments, the threshold for an indication/alarm could be 85 degrees or 90 degrees. The patient inline can be determined or based on any relevant measurements. For example, the patient incline can be based on measurements taken at ends of the patient's body, such as the patient's head and feet. Alternatively, this determination can be based on measurements taken along the patient's chest, abdomen, back, etc. For example, measurement at the upper leg may reduce false positive alarms that may occur with other sensor positions. Position on the upper leg will not be affected by the patient sitting upright, since even while in the sitting position the upper leg will still be largely perpendicular to the floor (0 degrees incline), and only with standing will the upper leg be at an incline of approximately 90 degrees.

However, other embodiments do not make the above determinations based on patient incline, and instead focus on other measurements. For example, some embodiments use a sensor, such as an accelerometer, to detect a type of movement, such as a significant movement characteristic, of a patient indicative of an attempt to ambulate, i.e., walk. Some of these embodiments combine the accelerometer's measurement of movement with patient incline measurements to detect a patient's attempt to get up or ambulate.

V. RESPIRATORY MONITORING

Many of the disclosed embodiments are directed to respiratory monitoring. Embodiments are intended to measure, directly or indirectly, any physiological condition from which any relevant aspect of respiration can be gleaned. For example, some of the embodiments measure different or overlapping physiological conditions to measure the same aspect of respiration. Alternatively, some embodiments measure the same, different or overlapping physiological conditions to measure different aspects of respiration, i.e., respiration rate versus depth of breath.

Any and all of the embodiments disclosed above can be used in any beneficial context, such as at any applicable location. For example, embodiments can be used in homes, workout facilities, physical therapy facilities, or medical care facilities, including but not limited to hospitals, retirement facilities, rehabilitation facilities, etc.

However, some of the above embodiments are more applicable at certain locations. For example, embodiments that measure respiration for monitoring sleep apnea are typically more applicable at the home or medical care facilities in which patients spend the night or otherwise sleep, such as in hospitals, retirement facilities, etc. This respiratory monitoring may be used as routine monitoring in a hospital or nursing home, as well as in homes, e.g., to monitor adults, children, or infants, who are at risk for apnea (breath holding).

In fact, as disclosed above in other contexts, some embodiments include sensor(s) and sensor systems(s) having elements and/or functionalities at different locations. For example, data obtained by the disclosed sensor(s) and sensor systems(s) can be transmitted to other locations. Some of the locations receiving this data may be relatively local or proximal to the patient, such as at a nurses station in the hospital in which the patient is receiving treatment. Alternatively, this data may be transmitted more remotely from the patient, such as to a central receiving station or medical information repository, that is disposed hundreds or thousands of miles from the patient.

Embodiments are intended to cover or otherwise include any known, related art, or later developed technologies usable to perform the disclosed respiratory monitoring. Some of these embodiments use or otherwise include apparatus and methods disclosed herein in different contexts, such as incline monitoring, fall prevention monitoring, etc., and apply them, in whole or in part, to respiratory monitoring. For example, many of the disclosed embodiments include an accelerometer to measure various physiological conditions indicative of various aspects of respiration. Other embodiments use or otherwise include apparatus and methods different than those disclosed above, and instead include and/or use apparatus and methods specifically tailored to respiratory monitoring.

Some of the embodiments use sensors, such as accelerometers, to measure patient chest incline angles to measure certain physiological conditions relevant to aspects of respiration. For example, some of these accelerometers and sensor systems determine the movement of the chest up and down that occurs during breathing (respiration). However, not all of the embodiments focus on chest incline monitoring, and instead measure other conditions. For example, some embodiments include sensor(s), such as other types of accelerometers, that measure changes in position or motion of the sensor and/or chest to measure certain physiological conditions relevant to aspects of respiration.

Various aspects of respiration monitoring according to some embodiments are disclosed below for exemplary purposes. However, these aspects are not intended as an exhaustive listing of all aspects of respiratory monitoring covered by the various embodiments.

A. General Monitoring and Indications/Alarms

As disclosed above, some embodiments measure certain physiological conditions to monitor different aspects of respiration, i.e., respiration rate versus depth of breath. These embodiments are intended to cover or otherwise include any useful or beneficial application of this data, including any useful or beneficial indications or alarms.

Embodiments that monitor respiration rate, i.e., number of breaths taken over a period, are intended to include or otherwise use any technology applicable to measure the corresponding physiological condition. These embodiments are also intended to include any and all methods and apparatus for applying this data in any useful or beneficial manner.

Some of these embodiments use computer algorithms to diagnose different pathologic conditions of breathing using the respiration rate data. For example, in some embodiments, a default indication/alarm is set to indicate certain conditions, such as a condition where the respiration rate is less than a certain number, such as 10, or greater than a certain number, such as 30. Indication/alarm thresholds can be graded so that different types of indications/alarms are provided depending on the sensed conditions. As one example, a low respiratory rate indication/alarm can be provided if the respiratory rate is less than 10 but greater than 4, while a very loud critical indication/alarm can be provided if the respiratory rate is 4 or less to indicate impending respiratory arrest. Indication/alarm thresholds can also be graded based on the trend of sensed conditions. Specific sensed conditions may initiate additional one time and periodic measurements to better determine the patient's condition. As one example, a low respiratory rate below 15 may initiate more frequent measurements, such as respiration rate, respiration depth, heart rate, and other exemplary measurements, to monitor the patient more closely and determine if the condition changes. If the subsequent measurements indicate the patient condition is improving, the frequency and type of measurements may be decreased to conserve battery life. Alternatively, if the subsequent measurements indicate the patient condition is not improving, in one exemplary embodiment the device may initiate a command to interact directly with the patient. As one example, the device may initiate a verbal message or loud buzzer to wake the patient in an effort to increase breathing or otherwise improve their condition. In another example, the device may initiate an electric shock, vibration, or other type of stimulation to wake the patient to increase breathing or otherwise improve their condition.

Embodiments that monitor depth of breath, i.e., the magnitude of breath(s) taken, are intended to include or otherwise use any technology applicable to measure the corresponding physiological condition. These embodiments are also intended to include any and all methods and apparatus for applying this data in any useful or beneficial manner.

Some of these embodiments use accelerometer(s) to monitor respiration by measuring magnitude of chest excursion, i.e., a relatively large breath (tidal volume) results in a relatively large movement of the accelerometer, whereas a relatively small breath results in a relatively small movement of the accelerometer. However, embodiments are intended to include any apparatus to perform this measurement.

Some embodiments measure both the respiratory rate as well as the depth of respiration. Embodiments are intended to include any methods and apparatus to perform this dual monitoring and/or use or apply the data obtained thereby. For example, a computer algorithm can be provided to use or apply both the respiratory rate as well as depth of respiration data for any purpose.

This dual monitoring can be useful for hospitalized patients at risk for apnea or respiratory depression, e.g., patients in a non-ICU setting who are receiving respiratory depressants (e.g., opiate type pain medications). For example, it is common in some hospitals for patients with a history of severe obstructive sleep apnea to need ICU care after routine surgery due to potential adverse effects of opiates on respiration. Therefore, the above dual monitoring is beneficial by enabling patients to be located in a non-ICU setting (e.g., hospital ward) soon after surgery, such as the first night after surgery, thereby making the ICU available for patients in greater need of ICU care.

As another example, respiratory depression caused by opiates (e.g., morphine, fentanyl, dilaudid) is typically characterized by slow and deep breathing, e.g., respiratory rate of 4 to 6, with very large tidal volumes. A processor or other device can measure trends/changes over time, and even take into account other physiological conditions, and provide indications/alerts accordingly. For example, a patient's heart rate decreasing from 18 to 16 to 14 to 12 to 10 over 1 hour may indicate progressive respiratory depression, and an indication/alert can be provided, such as to the caregivers, at this early stage. In contrast, it may not be necessary to provide such an indication/alert for a patient whose respiratory rate is 10 and not decreasing.

However, the above scenarios are only provided for exemplary purposes, and not intended as an exhaustive listing of applications of the embodiments that focus on respiration monitoring.

B. Combining Measured Respiration with Other Data

As disclosed above, some embodiments combine the use of respiration data with other data for a variety of useful purposes. As one example, patient mobility can be taken into account with the respiratory data to arrive at a certain diagnosis or to make some other determination. Heart rate is another source of data that can similarly be taken into account with the respiratory data. In fact, multiple types of data, e.g., both mobility data and heart rate data, can be taken into account with respiratory data to arrive at a certain diagnosis or to make some other determination. Some of these determinations relate directly or indirectly to certain physiological conditions of the patient, such as gastric health, adequacy of resuscitation, etc. Contrarily, other determinations relate to or otherwise facilitate the interpretation of other data, such as to achieve an enhanced interpretation of respiratory data.

As one example, in some scenarios, a patient can tolerate a lower heart rate and respiratory rate if the patient is immobile. Thus, the sensor(s) and/or sensor system(s) of some embodiments monitor the above physiological conditions and provide diagnoses or make other determinations based on the combined data.

Physiological conditions of the patient, as well as factors external to the patient, can be taken into account, such as by a processor's algorithm of the sensor(s) or sensor system(s), for any useful purpose, such as to provide or facilitate an enhanced or improved interpretation of respiratory monitoring. An example of a physiological condition of the patient that can be taken into account as disclosed above is the patient's heart rate. Another example of such a condition is evidence of patient movement, such as walking, based on a signature of acceleration and/or deceleration in the vertical and horizontal directions that are consistent with the type of movement at issue, such as walking. In these examples, if the patient appears to be walking in the hospital based on an increase in movement and heart rate, then an increase in respiratory rate would be expected. However, the above scenarios are merely provided for exemplary purposes, and are not intended to be an exhaustive listing of physiological conditions of the patient that can be taken into account for any beneficial reason, such as to facilitate an enhanced interpretation of respiratory data.

An example of an external factor is the time of the day. For example, at night, such as 3:00 am, it is more likely that the patient is in bed and sleeping, therefore, one would predict there to be less movement, a lower heart rate, and a lower respiratory rate consistent with normal patterns of respiration during sleep versus awake states. However, the above scenario is merely provided for exemplary purposes, and is not intended to be an exhaustive listing of external of the patient that can be taken into account for any beneficial reason, such as to facilitate an enhanced interpretation of respiratory data.

Embodiments are intended to cover or otherwise include any beneficial use and/or application of the combined data disclosed above, not only in the context of providing diagnoses and/or making other determinations, but also in the form of different types of communicating the diagnoses and/or other determinations, such as via indications/alarms. A few such indications/alarms are provided below for exemplary purposes, and are not intended to be an exhaustive listing of indications/alarms covered by the embodiments.

In some embodiments, an indication/alarm is provided if the patient's respiratory rate drops below a certain lower setpoint or threshold. In some of these embodiments, or other embodiments, an indication/alarm is provided if the patient's respiratory rate rises above a certain higher setpoint or threshold. These embodiments are beneficial in various respects, such as by providing an alert or indication, such as to a caregiver, that the patient's respiratory rate has deviated from a respiratory rate or range of rates that are desired. However, other data, such as data relating to the patient's physiological conditions and/or external factors, can be used to modify the above lower and/or higher setpoints or thresholds.

In one embodiment, the lower respiratory rate setpoint or threshold is modified based on the patient's level of activity. For example, the lower respiratory rate setpoint may be reduced if the patient is inactive, such as asleep, while the lower respiratory rate setpoint may be increased if the patient is engaged in some activity. This embodiment may be beneficial because a reduced lower respiratory rate may be acceptable, or at least not sufficiently undesirable so as to warrant communication of an indication/alarm, if the patient is inactive. Contrarily, an increased respiratory rate may be necessary if the patient is engaged in a certain activity.

In one such embodiment, a lower respiratory rate threshold, such as a rate of 15, may trigger an indication/alarm if the sensor(s)/sensor system(s) determines that the patient to be awake and/or moving. On the other hand, if the sensor(s)/sensor system(s) determines that the patient is asleep and/or not moving, then a more appropriate lower respiratory rate threshold may be set, such as a respiratory rate of 10, to account for slower respirations during sleep, and to reduce of avoid "alarm fatigue," such as by nursing staff.

In addition, or as an alternative to the above, an upper threshold for respiratory rate can be adjusted based on patient physiological conditions and/or external factors, such as the patient's level of activity. For example, the upper respiratory rate setpoint may be reduced if the patient is inactive, such as asleep, while the upper respiratory rate setpoint may be increased if the patient is engaged in some activity. This embodiment may be beneficial because a reduced upper respiratory rate may be acceptable, or at least not sufficiently undesirable so as to warrant communication of an indication/alarm, if the patient is inactive. Contrarily, an increased upper respiratory rate may be desirable if the patient is engaged in a certain activity.

In one such embodiment, it may be desirable to increase the upper threshold for respiratory rate to 30 if the patient's physiological conditions and/or external factors indicate that such an increase is warranted, such as if the patient is active, e.g., walking. On the other hand, if the sensor(s)/sensor system(s) determines that the patient is asleep and/or not moving, then a more appropriate upper respiratory rate threshold may be set, such as a respiratory rate of 20, to account for slower respirations during sleep, and to reduce of avoid "alarm fatigue," such as by nursing staff.

Notwithstanding the above, it may always be desirable to have critical indications/alarms activated in cases of serious or potentially life threatening conditions. For example, the sensor(s) and/or sensor system(s) of some embodiments always provide an indication/alarm under certain circumstances, such as in the case of a heart rate of less than 30 beats per minute, or a respiratory rate less than 4.

The above physiological conditions and external factors are merely provided for exemplary purposes, and embodiments are intended to cover use of any data that is helpful to achieve the advantages disclosed herein. For example, some embodiments involving respiratory rates also take into account one or more other factors, including but not limited to patient age and/or size. For example, the normal magnitude of excursion (movement) of an accelerometer chip disposed on a patient's chest will vary based on the age and size of the patient. Thus, actual data relating to magnitude of excursion (movement) measured by an accelerometer chip disposed on a patient's chest can be compared to data for a normal individual of that age and size. One such embodiment uses the following average respiratory rates ($V_f$) by age: Newborns: 30-40 breaths per minute; Less Than 1 Year: 30-40 breaths per minute; 1-3 Years: 23-35 breaths per minute; 3-6 Years: 20-30 breaths per minute; 6-12 Years: 18-26 breaths per minute; 12-17 Years: 12-20 breaths per minute; and Adults Over 18: 12-20 breaths per minute.

C. Monitoring Respiration Over Time

Some embodiments include sensor(s) and sensor system(s) that monitor, record, and utilize/apply respiratory and other data, including but not limited to data relating to other physiological conditions, over time. This data is referred to herein as historical data.

Embodiments are intended to utilize known, related art, and/or later developed technologies to perform the above. Embodiments are also intended to include or otherwise cover any useful or otherwise beneficial application of the above historical data. A few such embodiments are disclosed below for exemplary purposes, and are not intended to be an exhaustive listing of usages/applications of the historical data covered by the various embodiments.

Some embodiments include a processor that utilizes algorithms to provide indications/alarms, such as "smart alarms," based on historical data for a particular patient. For example, if the patient is monitored for a certain period, such as 72 hours, data relating to patterns of movement (incline, acceleration, etc.), heart rate, respiratory rate, etc., over time and at different times, can be monitored and applied for various beneficial uses/applications.

In some embodiments, this data is used to enhance or improve the discrimination of the sensor(s) and/or sensor system(s) to detect relevant conditions, such as potentially dangerous conditions. For example, mean and 1 and 2 standard deviations for heart rate and respiratory rate can be calculated for periods in which the patient is not moving (immobile), as opposed to periods in which accelerometer data makes clear that the patient is moving. These "normal values" for the patient for the moving and immobile states can be used to determine appropriate but different thresholds for indication/alarm triggers in different states, for example, moving versus immobile. An example for a hypothetical patient is shown in the table below:

Mean (2 Standard Deviation) Shown

|  | Movement | Immobile | Alarm thresholds when moving | Alarm Thresholds when immobile |
| --- | --- | --- | --- | --- |
| Respiratory Rate | 16 (8) | 12 (6) | 8 low, 24 high | 6 low, 18 high |
| Heart Rate | 90 (20) | 70 (10) | 70 low, 110 high | 60 low, 80 high |

Similar use of patient historical data can be used in other contexts, such as different states of consciousness, e.g., awake versus asleep, or even different states of sleep. In one such example, data relating to the time of day (e.g., period of 1:00-4:00 am) can be used with data relating to patient movement (e.g., immobility—lack of patient movement) to make certain determinations. In the above example, i.e., period of 1:00-4:00 am and patient immobility, the sensor(s) and/or sensor system(s) can determine that the patient is likely asleep, and modify measured and/or calculated relevant physiological conditions accordingly, e.g., calculate normal (e.g., mean+/−2 SD) values for respiratory rate and heart rate that would be appropriate or otherwise desirable for the patient being asleep. Such calculated values can be used as above to set indication/alarm thresholds for the patient in the likely sleep state.

In addition, historical data for the patient during the above periods can be used to further modify the measured and/or calculated relevant physiological conditions. For example, historical data for the patient's awake and sleep states can be monitored, analyzed and taken into account in determinations/applications, such as the setting of acceptable parameters or indication/alarm thresholds of different physiological conditions, including but not limited to respiratory rate parameters. This feature may be especially beneficial because it personalizes determinations/applications that are more consistent with normal, acceptable, unacceptable, etc., physiological conditions for each specific patient, including but not limited to respiratory rate parameters.

However, the above use of historical data to personalize diagnoses, treatment, indications/alarms, etc., is merely provided for exemplary purposes, and is not intended to be a complete listing of applications of historical data according to the embodiments.

D. Specific Applications

A few general applications of respiratory monitoring are disclosed above for exemplary purposes, and those of ordinary skill in the art will understand that the embodiments can be applied in other contexts. In other words, the respiratory monitoring can be used or otherwise applied to: 1) diagnose conditions disclosed above, 2) diagnose conditions other than those disclosed above, and/or 3) any other beneficial purpose.

For example, a few such specific applications are disclosed below for exemplary purposes, and are not intended as an exhaustive listing of beneficial applications of the disclosed respiratory monitoring.

1. Conscious Sedation Application

In some embodiments, the described apparatus and methods for monitoring respiratory rates and/or magnitudes of chest movement are performed during medical procedures where it is essential to monitor these critical variables. For example, many patients undergo procedures involving "sedation" or "conscious sedation," where there is risk for apnea, respiratory arrest, and/or hypoventilation. Examples of these situations include, but are not limited to, colonoscopy, cardiac catheterization, dental procedures, diagnostic procedures in children (e.g., CT scan), and surgery under sedation in the operating room.

Respiratory rates and/or magnitudes of chest movement need to be monitored during some or all of all of the above procedures, as well as postoperatively (e.g., as in the Recovery Room), and until the patient has recovered sufficiently from the sedation and procedure. In one embodiment, a strip containing any of the sensor(s) and/or sensor system(s) disclosed above is attached to the patient's anterior chest (e.g., above the sternum, a.k.a. breastbone) using any of apparatus also disclosed above (e.g., adhesive, clips to gown, one or more belts, etc.).

Data from the sensor(s) is transferred, wirelessly, via hard wire, or any other mechanism, to an indicating device, such as a monitor, to ultimately provide relevant data to medical care providers or other relevant personnel. The monitor can include an appropriate alarm or other indicator, and can also be located at a patient's bedside, CT scanner room, at a remote location such as a CT control room, or any other beneficial location. It may be desirable in many applications for the collected data (respiratory rate and/or respiratory depth) to be transferred to a hospital's electronic medical record through an RS-232 connector or any other routinely used connector.

2. Quantification of Respiratory Depth Variable

Some embodiments quantify a respiratory depth variable. For example, it may be beneficial in certain situations to calibrate the respiratory depth monitor to establish an association between a certain size breath (tidal volume) and the degree of excursion (movement) of the patient's chest or in some cases the patient's abdomen.

Exemplary embodiments perform this calibration at any appropriate or beneficial time, such as before a conscious sedation procedure. In some embodiments, the sensor is attached to the patient, either directly or indirectly, and the sensor begins monitoring the patient, and can send the measured data, such as data relating to measured chest movement, to a processor or other device. A medical care provider can then instruct the patient to take a certain number, such as three, large breaths, e.g., "take as large a breath as you can three times." At that point, the processor can be instructed to set the next received measured chest movement data to correspond to "100%" breath depth. In one such embodiment, an actuator, such as a button, is actuated at a monitor so that the processor, via a computer algorithm, corresponds the next received amount of measured chest movement data (e.g., 1 cm up on inspiration and 1 cm down on expiration) to "100%" breath depth.

Some embodiments only include the above calibration, such that no other calibration is necessary. In these embodiments, all future depth of breath data is interpreted as a percentage of the largest possible breath. Alternatively, in other embodiments, a two-point calibration is performed, where after the largest breath is recorded or otherwise communicated to the processor or other device, the patient is instructed to take a certain number, such as three, small breaths, e.g., "take 3 small breaths as small as possible." At that point, the processor can be instructed to record the average, or in some embodiments the smallest, of these small breadths. In one such embodiment, an actuator, such as a button, is actuated at a monitor so that the processor, via a computer algorithm, corresponds to the next received amount of measured chest movement data. With this two-point calibration, the patient's depth of respiration during the procedure, or at any time, can also be expressed in any beneficial or useful manner relative to the average, or in some embodiments, the smallest, of the small breadths.

Embodiments perform all of the above calibration techniques (including but not limited to the single point and two-point calibration techniques disclosed above) in any beneficial or useful setting, such as prior to use of the sensor in a hospitalized patient who will be monitored on the ward (non-ICU setting), or even in an ICU setting for patients receiving or not receiving mechanical ventilation. Calibration in a ventilated patient can be performed by administering a large tidal volume to the patient (e.g., 3 breaths of 10 ml/kg lean body weight), and instructing the processor, such as by actuating a "large breath calibration" actuator (e.g., button), to record the magnitude of chest movement with this large breath.

3. Determining Whether Patient is Becoming Tired

The above respiratory monitoring can be used to determine whether a patient is becoming tired. For example, in some embodiments, the disclosed respiratory apparatus and methods are used to guide the care of an ICU patient not on a ventilator, but who is at risk for becoming tired and needing either invasive or non-invasive ventilatory support. In other embodiments, the disclosed respiratory apparatus and methods are used to guide the care of an ICU patient, typically with a tracheostomy or endotracheal tube, who is very weak and receiving increasing (typically daily) durations with no or less ventilator support in order to work the respiratory muscles.

It may be beneficial or otherwise important in the above settings to determine a point or period in which the patient is tiring and needs to receive more ventilator support. In these settings, determining the change-over time in the respiratory rate and depth of respiration can guide a decision as to whether the patient is tiring (e.g., trend toward increased rate and decreased depth), and may need respiratory support with either non-invasive ventilation or invasive ventilation (e.g., patient intubated with an endotracheal tube that is connected to a ventilator). For example, a condition in which the initial RR is 16, the total movement of the depth sensor is 1 cm (1 cm up and 1 cm down), and there is gradual or rapid increase in RR to 25 with depth decreasing to 0.3 cm, may indicate that the patient is beginning to tire and that more ventilator support is needed.

4. Diagnosis of Respiratory Conditions

Some or all of the above respiratory monitoring methods and apparatus, such as those involving the pattern of timing of movement of the breathing (depth of breath), can be used to help diagnose certain pathologic forms of breathing. For example, the ratio of time in inspiration (chest sensor moves up) to expiration (chest sensor moves back down) is typically 1:2 or approximately 1:2 in adults and 1:3 or approximately 1:3 in children, which is also known as the I:E ratio. Bronchospasm (as seen in asthmatic individuals) typically results in prolonged expiration, because the individual takes longer to exhale the breath due to the obstruction to airflow being more significant during expiration.

Therefore, an increase, and especially an acute and/or sudden decrease, in the I:E ratio (e.g. from 1:2 to 1:4) may suggest or strongly suggest the onset or worsening of bronchospasm, which can be treated with appropriate medications, e.g., bronchodilators. As one example, if a patient monitored as disclosed above has a typical or substantially typical I:E, e.g., 1:2 or approximately 1:2 in adults and 1:3 or approximately 1:3 in children, and the I:E gradually or suddenly decreases, such as to 1:4, then this increase may suggest or even strongly suggest the onset or worsening of bronchospasm, which can be treated with appropriate medications, e.g., bronchodilators. Alternatively, if a patient experiences existing bronchospasm (e.g., I:E of 1:4), then the above monitoring can be performed to quantitate the change in the I:E over time, such that an increasing of the I:E may indicate worsening and a decrease in the I:E may indicate improvement.

Additional pathologic or concerning respiratory conditions can be detected using the sensor(s) and sensor system(s) disclosed above. In one example, fine crackles (rales) during the inspiratory phase is strongly suggestive of pulmonary edema, a common condition in ICU and other hospitalized patients, where the alveoli (air sacs) of the lungs begin to fill with fluid. In another example, coarse rumbling vibrations during inspiration and expiration, my indicate the development of secretions in the airways of the lungs, which can adversely affect breathing and be a warning sign of lung infection, e.g., pneumonia. Early diagnosis of this and other conditions (e.g., pulmonary edema, bronchospasm), using the disclosed sensor(s) and sensor system(s) may result in better patient outcomes. For example, early diagnosis and treatment may reduce or prevent the need for ICU care, or intubation and mechanical ventilation, for common hospital complications, including but not limited to the following:

Pulmonary Edema: Usually treatable at an early stage with diuretics, fluid restriction, and/or nitroglycerin depending on the patient's history and comorbidities.

Bronchospasm/Asthma Attack: Usually treatable at an early stage with bronchodilators (e.g., albuterol), steroids (prednisone), and antibiotics if bacterial infection has been a trigger.

Increased Secretions: In the setting of likely bacterial infection usually can be treated with antibiotics before the condition worsens.

In another embodiment, data on heart rate and respiratory rate obtained by the sensor(s) and/or sensor system(s) disclosed above, such as any of the disclosed accelerometers, can be combined with additional data, e.g., arterial hemoglobin oxygen saturation obtained by pulse oximetry ($SpO_2$), to improve, enhance or even optimize the function and/or application of the sensor(s), sensor system(s), indications/alarms, etc. This procedure may be particularly useful/beneficial if the data for these different measurements are collected and displayed in a common location, such as by a single integrated monitor.

In one such embodiment, if $SpO_2$ decreases from 98% to 94%, at the same time that a possible diagnosis of pulmonary edema is suggested by the sensor(s) and/or sensor system(s) based on the likely signature for pulmonary edema (vibrations from rales during inspiration), then an indication/alarm ("smart alarm"), such as in the form of a higher alert, can be transmitted or otherwise communicated to caregivers, such as nurses, doctors, clinicians, etc., to notify them of the potential life threatening nature of this condition. This procedure/application is beneficial since, in most clinical settings, a change in $SpO_2$ from 98 to 94% would normally not trigger major concern. However, in the setting/context of new inspiratory rales, the change is more concerning, and also reinforces the diagnosis that pulmonary edema is more likely.

Embodiments are intended to include or otherwise utilize any medium or type of indication/alarm that may be beneficial. For example, the above diagnosis can be indicated by an audible alarm due to its severity. In addition, the sensor(s)/sensor system(s) can include a monitor providing an additional indication/alarm, such as a text indication/alarm that describes the likely or possible diagnosis, e.g., in this case "New onset pulmonary edema suspected due to sounds of inspiratory rales and decreasing oxygen saturation."

5. Determining Respiratory Obstructions

Some or all of the above respiratory monitoring methods and apparatus disclosed above, such as those involving the pattern of timing of movement of the breathing (depth of breath), can be used to help diagnose respiratory obstructions. For example, breathing movement of patients suffering from respiratory obstructions is manifested by sharp rocking or jerking movements, as opposed to softer more graceful movements indicative of normal breathing. One or multiple sensors, such as accelerometers, can therefore be placed at various relevant locations(s) to send measurements to other elements of the sensor system, such as a processor or other device with algorithms, to determine whether the breathing movement is indicative of respiratory obstructions.

One embodiment provides a sensor on the patient's chest and another sensor on the patient's stomach. The relative movement of the patient's chest and stomach is transmitted to a processor or other device with algorithms to determine whether the relative breathing movement of the chest and stomach is indicative of respiratory obstructions. Another embodiment replaces the separate sensors of the above embodiment with a single sensor spanning the patient's chest and stomach, such as from the middle of the patient's chest to the patient's belly button.

Embodiments are intended to include any sensor configurations to provide the above data. Embodiments are also intended to include other useful or beneficial uses/applications of the above data relating to relative movement beyond respiratory obstruction detection.

VI. HEART RATE MONITOR

Some of all of the sensor(s) and/or sensor system(s) disclosed above can be applied in the context of monitoring heart rates. A summary of these embodiments as well as a few specific applications are disclosed below for exemplary purposes, and are intended as an exhaustive disclosure of all usages of heart rate monitoring covered by the embodiments.

A. Summary

Many of the disclosed embodiments are directed to heart rate monitoring. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different or overlapping physiological conditions to measure different aspects of heart rate, i.e., number of beats, strength of beats, regularity of beats, beat anomalies, etc.

Any and all of the embodiments disclosed above can be used in any beneficial context, such as at any applicable location. For example, embodiments can be used in homes, workout facilities, physical therapy facilities, or medical care facilities, including but not limited to hospitals, retirement facilities, rehabilitation facilities, etc.

However, some of the above embodiments are more applicable at certain locations. For example, embodiments that measure potentially rather critical aspects of heart rate that may have immediate and severe impacts on patient health are typically more applicable at medical care facilities in which patients housed, such as in hospitals, retirement facilities, etc. Embodiments that measure less critical aspects of heart rate may be especially applicable in homes, e.g., to monitor heart rates of adults, children, or infants.

In fact, as disclosed above in other contexts, some embodiments include sensor(s) and sensor systems(s) having elements and/or functionalities at different locations. For example, data obtained by the disclosed sensor(s) and sensor systems(s) can be transmitted to other locations. Some of the locations receiving this data may be relatively local or proximal to the patient, such as at a nurses station in the hospital in which the patient is receiving treatment. Alternatively, this data may be transmitted more remotely from the patient, such as to a central receiving station or medical information repository, that is disposed hundreds or thousands of miles from the patient.

Embodiments are intended to cover or otherwise include any known, related art, or later developed technologies usable to perform the disclosed heart rate monitoring. Some of these embodiments use or otherwise include apparatus and methods disclosed herein in different contexts, such as incline monitoring, fall prevention monitoring, respiratory monitoring, etc., and apply them, in whole or in part, to heart rate monitoring. For example, many of the disclosed embodiments include an accelerometer to measure various physiological conditions indicative of various aspects of heart rate. Other embodiments use or otherwise include apparatus and methods different than those disclosed above, and instead include and/or use apparatus and methods specifically tailored to heart rate monitoring.

Various applications of heart rate monitoring according to some embodiments are disclosed below for exemplary purposes. However, these aspects are not intended as an exhaustive listing of all aspects of heart rate monitoring covered by the various embodiments.

B. Specific Applications

A few embodiments that include sensor(s) and/or sensor system(s) having accelerometer(s) usable as heart rate monitors are disclosed below for exemplary purposes. In some of these embodiments, the accelerometer is attached to a patient's chest or area near the patient's chest, e.g., at or on (or substantially at or on) the patient's breastbone. Each heartbeat causes a vibration due to movement of the heart, closure of the heart valves, and/or in some instances movement of blood through the vessels, etc. This vibration is typically transmitted to the surface of the chest in most patients. Thus, an accelerometer disposed as disclosed above can measure heart rate in adults, children, animals (e.g., veterinary hospital), etc.

The dynamic acceleration properties of the accelerometer can be used to measure the heart rate, and as with the depth of respiration monitor, the measured data can be transmitted to a processor and/or monitor (either bedside, remotely as in central monitoring station, etc.), and appropriate indication/alarm thresholds can be used. The indication/alarm thresholds can be adjusted based on patient age (see normal range of heart rates based on age) or any other patient condition. In one example, for a patient with significant coronary artery disease or critical aortic stenosis, it may be desirable to set a lower indication or alarm threshold, e.g., 90 beats per minute, in order to detect even modest increases in heart rate that can be deleterious in these types of patients.

Additional embodiments include algorithms that allow for a more rapid diagnosis of certain cardiac disorders, since earlier diagnosis of these complications in hospitalized patients can improve the likelihood of a good outcome.

In some examples, the development of a new cardiac rhythm, e.g atrial fibrillation, is a manifestation of another more serious condition, such as an evolving myocardial infarction (heart attack). In this case it is important to diagnose the atrial fibrillation earlier as this will trigger ordering of a 12 lead ECG, which will lead to the earlier diagnosis of the myocardial infarction. This would be particularly helpful in a patient on a hospital ward (non-ICU) who is not on continuous ECG telemetry, and where standard vital signs (heart rate, respiratory rate) are monitored every 4 hours. In an exemplary embodiment, measurements of heart rate and other vital signs can occur much more frequently. As one example, heart rate, respiratory rate, respiratory depth, and other vital signs can be taken every 15 minutes. Specific sensed conditions may initiate additional one time and periodic measurements to better determine the patients' condition. As one example, a high or irregular heart rate may initiate more frequent measurements to monitor the patient more frequently and determine if the condition changes. If the subsequent measurements indicate the patient condition is improving, the frequency and type of measurements may be decreased to conserve battery life. Alternatively, if the subsequent measurements indicate the patient condition is not improving, in one exemplary embodiment the device may initiate a command to interact directly with the patient. As one example, if the heart rate is too low the device may initiate a verbal message or loud buzzer to wake the patient in an effort to increase the heart rate or otherwise improve their condition. In another example, the device may initiate an electric shock, vibration, or other type of stimulation to wake the patient to increase the heart rate or otherwise improve their condition.

In another example, the development of the new cardiac rhythm, e.g. atrial fibrillation, is clinically serious in and of itself. For example, atrial fibrillation can lead to decreased stroke volume, cardiac output, and systemic blood pressure, which can lead to organ ischemia, e.g. stroke, kidney failure, myocardial ischemia. In this example, earlier detection of the atrial fibrillation will trigger other routine testing (e.g. more frequent blood pressure measurements, 12 lead ECG, possibly a transthoracic echocardiogram) all of which can confirm the diagnosis and lead to the initiation of definitive treatment.

Data generated by an accelerometer using different sampling rates, e.g. 25-100 Hz, can distinguish between different types of heart sounds that occur in both health and disease. Closing (and in some cases opening) of the heart valves at different times in the cardiac cycle results in vibrations, which can be auscultated with a stethoscope, or detected using an accelerometer. For example, at 50 Hz sampling rate one can distinguish the normal cardiac sounds of S1 followed by S2, where S1 is the first heart sound produced by closing of the AV valves (mitral valve and tricuspid valve), and S2 is the second heart sound produced by closing of the semilunar valves (aortic valve and pulmonary valve). Other sounds, including murmurs, and gallop rhythms such as S3 and S4 can also be detected based on their specific signature. It has previously been described that an accelerometer can be used to determine the heart rate, however, in a preferred embodiment the sensor's processor can detect the normal heart sounds S1 and S2 in a hospitalized patient as well as different pathologic cardiac conditions.

Figure 23A:
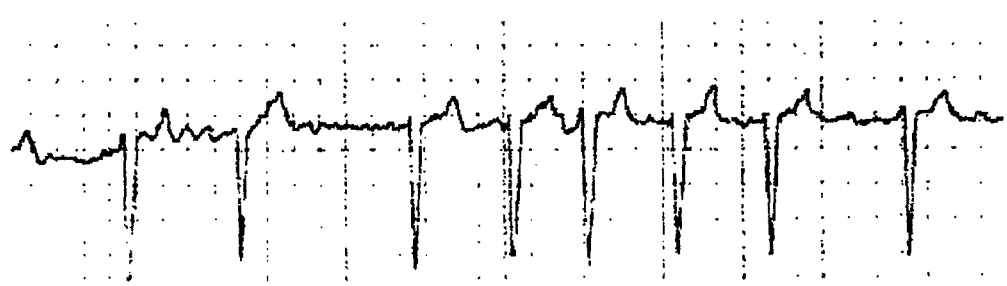
FIG. 23A is a waveform of irregularly irregular rhythm.

In the course of the hospital stay, the processor can detect a change in the cardiac rhythm, for example, to atrial fibrillation, which is one of the most common cardiac arrhythmias that develop in hospitalized patients. Atrial fibrillation is detected by the development of an irregularly irregular rhythm (in contrast to sinus arrhythmia) with development of significant variability in the intensity of the first heart sound (S1). FIG. 23A shows irregularly irregular rhythm. Note the absence of p-waves.

Figure 23B:
FIG. 23B is a waveform of sinus arrhythmia.

In addition, the heart rate (ventricular response) is often elevated in patients who are in atrial fibrillation. It should be noted that atrial fibrillation has a very characteristic pattern which is distinct from sinus arrhythmia, which is a normal mild acceleration and slowing of the heart rate that occurs with breathing in and out. See FIG. 23B.

The heart rate monitoring or measurement can be performed alone or in addition to respiratory monitoring, incline monitoring, and/or any other type of monitoring. In fact, embodiments are intended to cover or otherwise include combining the above heart rate monitoring with any other data, including but not limited to other data disclosed herein, that may provide beneficial or desirable results.

VII. MONITORING FOR MOVEMENT BASED CONDITIONS INCLUDING SEIZURES, SIDS, ETC

Some of all of the sensor(s) and/or sensor system(s) disclosed above can be applied in the context of monitoring for movement based conditions, including seizures, SIDS, etc., i.e., conditions that are defined by, closely related to, or otherwise affiliated with, certain type(s) of movement (or a lack thereof). A summary of these embodiments as well as a few specific applications are disclosed below for exemplary purposes, and are intended as an exhaustive disclosure of all usages of monitoring for these movement based conditions covered by the embodiments.

A. Summary

Many of the disclosed embodiments directly monitor/measure the specific type(s) of movement (or a lack thereof) at issue. However, embodiments are intended to measure, directly or indirectly, any other or additional physiological condition from which the specific type(s) of movement (or a lack thereof) at issue can be gleaned or otherwise better understood. For example, some of the embodiments measure different or overlapping physiological conditions to measure the specific type(s) of movement (or a lack thereof) at issue.

Any and all of the embodiments disclosed above can be used in any beneficial context, such as at any applicable location. For example, embodiments can be used in homes, workout facilities, physical therapy facilities, or medical care facilities, including but not limited to hospitals, retirement facilities, rehabilitation facilities, etc.

However, some of the above embodiments are more applicable at certain locations. For example, embodiments that measure potentially rather critical aspects of the specific type(s) of movement (or a lack thereof) that may have immediate and severe impacts on patient health are typically more applicable at medical care facilities in which patients housed, such as in hospitals, retirement facilities, etc. Embodiments that measure less critical aspects of the specific type(s) of movement (or a lack thereof) may be especially applicable in homes.

In fact, as disclosed above in other contexts, some embodiments include sensor(s) and sensor systems(s) having elements and/or functionalities at different locations. For example, data obtained by the disclosed sensor(s) and sensor systems(s) can be transmitted to other locations. Some of the locations receiving this data may be relatively local or proximal to the patient, such as at a nurses station in the hospital in which the patient is receiving treatment. Alternatively, this data may be transmitted more remotely from the patient, such as to a central receiving station or medical information repository, that is disposed hundreds or thousands of miles from the patient.

Embodiments are intended to cover or otherwise include any known, related art, or later developed technologies usable to perform the disclosed monitoring for certain type(s) of movement (or a lack thereof). Some of these embodiments use or otherwise include apparatus and methods disclosed herein in different contexts, such as incline monitoring, fall prevention monitoring, respiratory monitoring, heart rate monitoring, etc., and apply them, in whole or in part, to monitoring for certain type(s) of movement (or a lack thereof). For example, many of the disclosed embodiments include an accelerometer to measure, directly or indirectly, physiological conditions indicative of certain type(s) of movement (or a lack thereof). Other embodiments use or otherwise include apparatus and methods different than those disclosed above, and instead include and/or use apparatus and methods specifically tailored to monitoring physiological conditions indicative of certain type(s) of movement (or a lack thereof).

Various applications of monitoring physiological conditions indicative of certain type(s) of movement (or a lack thereof) according to some embodiments are disclosed below for exemplary purposes. However, these aspects are not intended as an exhaustive listing of all aspects of such monitoring covered by the various embodiments.

B. Specific Applications

Some of the embodiments directed to monitoring physiological conditions indicative of certain type(s) of movement (or a lack thereof) include sensor(s) and/or sensor system(s) having accelerometer(s) that measure dynamic acceleration, i.e., vibration. Some of these sensor(s) and/or sensor system(s) include processor(s) with algorithms to differentiate the body movement(s) at issue, such as body movements caused by seizures, from other types of body movements, such as body movements caused by breathing, beating of the heart, etc. Some of these embodiments can further include algorithms to differentiate between different types or states of the body movement(s) at issue, such as different types or states of seizures.

Embodiments are intended to cover or otherwise include any useful or beneficial utilization of this data. For example, an indication/alarm can be provided upon detection of the body movement at issue, or lack thereof. This indication/alarm can be provided local/proximal to the sensor(s)/sensor system(s) and/or the patient, or can be provided remotely therefrom. For example, this data can be communicated to a processor or other device to provide an indication/alarm to medical care providers, such as at a nurse's station, to indicate that the patient is experiencing a seizure. In an exemplary embodiment, coinciding with an alarm condition for a seizure, additional measurements of heart rate and other vital signs can also occur. This additional measurement information can be provided to help treat the patient.

The above applications are disclosed in the context of different types of body movements, such as occur during seizures, etc. However, other embodiments are directed to detecting, directly or indirectly, lack of certain or all types of body movements. Still other embodiments are directed to detecting physiological conditions, such as certain types of body movements, that may place a patient at risk for certain undesirable and/or harmful conditions, including those that result in a lack of body movement.

For example, some of these embodiments can include sensor(s) and/or sensor system(s) having accelerometer(s) that measure static and/or dynamic acceleration with algorithms to differentiate body movement(s) that may place the patient at risk of SIDS or other condition. As discussed with the other embodiments, these embodiments are intended to cover or otherwise include any useful or beneficial utilization of this data. For example, an indication/alarm can be provided upon detection of the body movement at issue, or lack thereof. This indication/alarm can be provided local/proximal to the sensor(s)/sensor system(s) and/or the patient, or can be provided remotely therefrom, such as to provide an indication that the patient is at risk of SIDS or other condition.

VIII. MONITORING CONDITIONS RELATED TO SLEEP

Some embodiments have been disclosed above in the context of monitoring different aspects of sleep, such as: 1) to diagnose sleep-related conditions, including but not limited to sleep apnea, 2) determining whether a patient is asleep or awake for the purpose of setting parameters relating to respiration, heart rate, etc. However, other embodiments include sensor(s) and/or sensor system(s) that can be applied in the context of monitoring other aspects of, or conditions directly or indirectly related to, sleep, including but not limited to duration, position, movements, quality, etc. A summary of these embodiments, as well as a few specific applications, are disclosed below for exemplary purposes, and are intended as an exhaustive disclosure of all usages of monitoring aspects of sleep or sleep conditions covered by the embodiments.

A. Summary

Embodiments are intended to measure, directly or indirectly, any physiological condition from which any relevant aspect of sleep or sleep condition can be gleaned or otherwise better understood. For example, some of the embodiments measure different or overlapping physiological conditions to measure the aspect of sleep or sleep condition at issue.

Any and all of the embodiments disclosed above can be used in any beneficial context, such as at any applicable location. For example, embodiments can be used in homes, workout facilities, physical therapy facilities, or medical care facilities, including but not limited to hospitals, retirement facilities, rehabilitation facilities, etc.

However, some of the above embodiments are more applicable at certain locations. For example, embodiments that measure potentially rather critical aspects of sleep or sleep conditions that may have immediate and severe impacts on patient health are typically more applicable at medical care facilities in which patients housed, such as in hospitals, retirement facilities, etc. Embodiments that measure less critical aspects of sleep or sleep conditions may be especially applicable in homes.

In fact, as disclosed above in other contexts, some embodiments include sensor(s) and sensor systems(s) having elements and/or functionalities at different locations. For example, data obtained by the disclosed sensor(s) and sensor systems(s) can be transmitted to other locations. Some of the locations receiving this data may be relatively local or proximal to the patient, such as at a nurses station in the hospital in which the patient is receiving treatment. Alternatively, this data may be transmitted more remotely from the patient, such as to a central receiving station or medical information repository, that is disposed hundreds or thousands of miles from the patient.

Embodiments are intended to cover or otherwise include any known, related art, or later developed technologies usable to perform the disclosed monitoring for aspects of sleep or sleep conditions. Some of these embodiments use or otherwise include apparatus and methods disclosed herein in different contexts, such as incline monitoring, fall prevention monitoring, respiratory monitoring, heart rate monitoring, monitoring for certain type(s) of movement (or a lack thereof), etc., and apply them, in whole or in part, to monitoring for aspects of sleep or sleep conditions. For example, many of the disclosed embodiments include an accelerometer to measure, directly or indirectly, physiological conditions indicative of certain type(s) or aspects of sleep or sleep conditions. Other embodiments use or otherwise include apparatus and methods different than those disclosed above, and instead include and/or use apparatus and methods specifically tailored to monitoring physiological conditions indicative of certain type(s) or aspects of sleep or sleep conditions.

Various applications of monitoring physiological conditions indicative of certain type(s) or aspects of sleep or sleep conditions according to some embodiments are disclosed below for exemplary purposes. However, these aspects are not intended as an exhaustive listing of all aspects of such monitoring covered by the various embodiments.

B. Specific Applications

Some of the embodiments directed to monitoring physiological conditions indicative of certain type(s) or aspects of sleep or sleep conditions include sensor(s) and/or sensor system(s) having accelerometer(s) that measure dynamic acceleration, i.e., vibration.

Embodiments are intended to cover or otherwise include any useful or beneficial utilization of the data obtained by the above sensor(s)/sensor system(s). For example, an indication/alarm can be provided upon detection of the aspect of sleep or sleep condition at issue. This indication/alarm can be provided local/proximal to the sensor(s)/sensor system(s) and/or the patient, or can be provided remotely therefrom. For example, this data can be communicated to a processor or other device to provide an indication/alarm to medical care providers, such as at a nurse's station, to indicate that the patient is experiencing the aspect of sleep or sleep condition at issue. In an exemplary embodiment, an alarm condition for a sleep condition can also include measurements of heart rate, respiratory rate, respiratory depth, and other vital signs. Specific sensed conditions may initiate additional one time and periodic measurements to better determine the patients' condition. As one example, a low heart rate or respiration may initiate more frequent measurements to monitor the patient more frequently and determine if the condition changes. If the subsequent measurements indicate the patient condition is improving, the frequency and type of measurements may be decreased to conserve battery life. Alternatively, if the subsequent measurements indicate the patient condition is not improving, in one exemplary embodiment the device may initiate a command to interact directly with the patient. As one example, if the heart rate or respiratory rate is too low the device may initiate a verbal message or loud buzzer to wake the patient in an effort to increase the heart rate or otherwise improve their condition. In another example, the device may initiate an electric shock, vibration, or other type of stimulation to wake the patient to increase the heart rate or otherwise improve their condition.

IX. GASTROINTESTINAL MONITORING

Some of all of the sensor(s) and/or sensor system(s) disclosed above can be applied in the context of monitoring various aspects of gastrointestinal function. A summary of these embodiments as well as a few specific applications are disclosed below for exemplary purposes, and are not intended as an exhaustive disclosure of all usages of monitoring gastrointestinal function covered by the embodiments.

Embodiments are intended to measure, directly or indirectly, any physiological condition from which any relevant aspect of gastrointestinal function can be gleaned. For example, some of the embodiments measure different or overlapping physiological conditions to measure the same aspect of gastrointestinal function. Alternatively, some embodiments measure the same, different or overlapping physiological conditions to measure different aspects of gastrointestinal function, i.e., motility, perfusion, etc.

Any and all of the embodiments disclosed above can be used in any beneficial context, such as at any applicable location. For example, embodiments can be used in homes, workout facilities, physical therapy facilities, or medical care facilities, including but not limited to hospitals, retirement facilities, rehabilitation facilities, etc.

However, some of the above embodiments are more applicable at certain locations. For example, embodiments that measure potentially rather critical aspects of gastrointestinal function that may have immediate and severe impacts on patient health are typically more applicable at medical care facilities in which patients housed, such as in hospitals, retirement facilities, etc. Embodiments that measure less critical aspects of gastrointestinal function may be especially applicable in homes, e.g., to monitor heart rates of adults, children, or infants.

In fact, as disclosed above in other contexts, some embodiments include sensor(s) and sensor systems(s) having elements and/or functionalities at different locations. For example, data obtained by the disclosed sensor(s) and sensor systems(s) can be transmitted to other locations. Some of the locations receiving this data may be relatively local or proximal to the patient, such as at a nurses station in the hospital in which the patient is receiving treatment. Alternatively, this data may be transmitted more remotely from the patient, such as to a central receiving station or medical information repository, that is disposed hundreds or thousands of miles from the patient.

Embodiments are intended to cover or otherwise include any known, related art, or later developed technologies usable to perform the disclosed gastrointestinal function monitoring. Some of these embodiments use or otherwise include apparatus and methods disclosed herein in different contexts, such as incline monitoring, fall prevention monitoring, respiratory monitoring, heart rate monitoring, etc., and apply them, in whole or in part, to gastrointestinal function monitoring. For example, many of the disclosed embodiments include an accelerometer to measure various physiological conditions indicative of various aspects of gastrointestinal function. Other embodiments use or otherwise include apparatus and methods different than those disclosed above, and instead include and/or use apparatus and methods specifically tailored to gastrointestinal function monitoring.

Various applications of gastrointestinal function monitoring according to some embodiments are disclosed below for exemplary purposes. However, these aspects are not intended as an exhaustive listing of all aspects of gastrointestinal function monitoring covered by the various embodiments.

A. Assessing Gastrointestinal Motility Via Accelerometer(s)

Some of the embodiments are directed to monitoring physiological conditions enabling assessment of gastrointestinal motility. These embodiments are intended to include any type of sensor enabling monitoring of these physiological conditions, including but not limited to accelerometer(s), such as those that measure dynamic acceleration, i.e., vibration.

There may be a number of vibration sources in the gastrointestinal tract related to motility. For example, the rhythmic motion of peristalsis in the stomach and small intestines produces vibrations. By measuring these vibrations and then correlating over time, there is an opportunity to capture the time and duration of specific phases of digestion. There is significant evidence the bowel sounds are correlated with motility. In a study by Watson W C and Knox E C. Phonoenterography: the recording and analysis of bowel sounds. *Gut,* 1967; 8, 88 ("Watson") the well-established sound patterns of peristalsis were measured and correlated with the digestion of a meal. For example, Watson measured the signature crescendo sounds of peristalsis as 1-6 seconds in duration with a 12-20 second interval.

Another source of vibrations is the result of oscillating gas bubbles in the small intestine. There is evidence these gas bubbles are continually present in the small intestine. In a study by Liu C J et al. Oscillating Gas Bubbles as the Origin of Bowel Sounds: A Combined Acoustic and Imaging Study. *Chin J Physiol.* 2010 Aug. 31; 53(4):245-53 ("Liu"), it was determined that bubbles could be identified by their oscillating frequencies. Further, the size of the bubbles could also be determined by the measured frequency. Liu also determined the size of the bubbles changed as they moved within the different sized structures of the small intestine. One embodiment is to analyze the pattern and frequency of the bubbles to assess gastrointestinal motility and other gastric functions.

Embodiments are intended to monitor any physiological condition enabling assessment of gastrointestinal motility. For example, an increase of intestinal contractions/motility may be used as evidence of a healthy or reasonably healthy gastric function, or vice versa, and care may be provided accordingly. Thus, some embodiments include sensor(s)/sensor system(s) that measure/monitor intestinal contractions/motility over time, determine whether an increase has occurred or is occurring, or vice versa, and provide indications/alarms accordingly.

Figure 6:
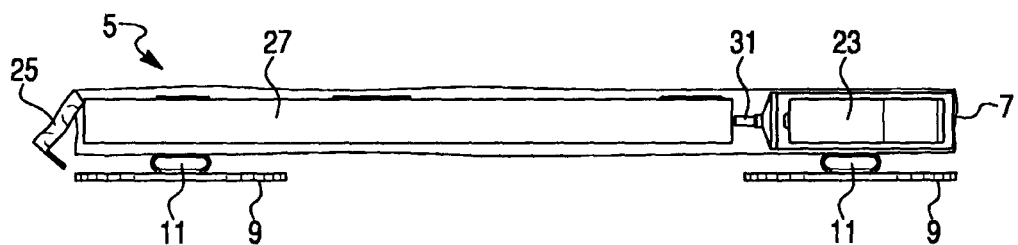
FIG. 6 is a side view of the attachment mechanism of FIGS. 2-5.

In one exemplary embodiment, a sensor, such as an accelerometer, is placed on the skin overlying the abdomen or even chest to capture vibrations associated with gastrointestinal motility. FIG. 6 is a schematic of an apparatus in accordance with an exemplary embodiment that includes a motility sensor for measuring gastrointestinal motility. The exemplary embodiment of FIG. 6 includes a wireless motility sensor 130 that is disposed at an appropriate location to detect the patient's gastrointestinal motility, and wirelessly transmits the detected gastrointestinal motility values to any of the disclosed indicators/controllers 8, 20. However, the wireless sensor 130 shown in FIG. 6 is not intended to be limiting, and exemplary embodiments are intended to cover any method and apparatus for obtaining the gastrointestinal motility values.

A gastrointestinal challenge agent, such as pentagastrin, may be used to challenge the gastrointestinal system, such as by injection into the patient. Injection of the challenge agent into a patient with a relatively healthy gastrointestinal system (such as would be evidenced by sufficient perfusion) will typically prompt motility after a period, such as less than one hour, while no, or reduced, motility is typically prompted by a relatively unhealthy gastrointestinal system. This process occurs because, in healthy patients, the challenge agent transiently increases blood flow in the gastric mucosa (lining of the stomach), causes contraction of smooth muscle of the LES, and increases motor activity of the colon and rectum.

Thus, monitoring for motility in this manner can be used to determined relative gastrointestinal health. However, exemplary embodiments are not limited to the use of pentagastrin, and are intended to cover any currently known method, apparatus, pharmaceutical, etc., capable of providing the effects discussed above or other effects useful in determining gastric function.

In an exemplary embodiment, bowel sounds can be auscultated, and the presence of bowel sounds (in conjunction with results from changes in gastric pH changes after pharmacological challenge) can be used to guide decisions to initiate, modify, or terminate enteral feeding. Auscultation of bowel sounds can be performed directly, e.g., with a stethoscope, however, in one exemplary embodiment, bowel sounds are recorded with an electronic stethoscope or microphone, which is coupled with a recorder that can monitor, record, and enable display of continuous data. This exemplary embodiment enables detection of less intense sounds compared with direct auscultation. In other words, direct auscultation is more likely to only allow detection of bowel sounds that are louder, and the sampling period is shorter due to the need for the person listening to be tethered to the patient via the stethoscope. In contrast, use of an electronic stethoscope, microphone, or accelerometer in conjunction with a recording device enables detection of less intense (less loud) and less frequent bowel sounds, which still indicate that there is adequate gastrointestinal motility to allow for enhanced, improved, and/or even successful enteral nutrition. In another exemplary embodiment, the vibrations from these bowel sounds can be detected and recorded via an accelerometer.

In one exemplary embodiment, the accelerometer is placed within the stomach to capture vibrations associated with motility, per FIG. 12. In another exemplary embodiment, the accelerometer is placed externally along the sternum of the patient. This location may be optimal in capturing GI related vibrations as well as other vibration related physiological information, such as heart rate, respiratory rate and function, etc. There may additionally be other advantageous locations for placement of the accelerometer, or multiple accelerometers. For example, accelerometer sensors could be placed over the diaphragm or along areas of the abdomen that are proximal to specific locations along the small and large intestine since these locations may enhance the auscultation of bowel sounds.

In another exemplary embodiment, the pattern of recorded bowel sounds can be interpreted in the context of the patient's care to determine if there is adequate motility. For example, the above embodiments can be performed alone or in conjunction with a pharmacological challenge. In one embodiment, administration of a prokinetic agent (e.g., metaclopromide, 10 mg every 6 hours intravenously, or erythromycin, 100 mg every 12 hours intravenously) is performed, and an increase in bowel sounds is used to help determine whether there is response to this medication and whether there is adequate motility for successful enteral nutrition. In another exemplary embodiment, bowel sounds and gastric juice pH are analyzed after administration of pentagastrin, and the presence of both bowel sounds and a positive pH response (i.e., decrease) to pentagastrin provides a very high level of confidence that enteral nutrition can be initiated with enhanced, improved and/or successful tolerance by the patient.

The various measures of motility can be combined with alerts and other mechanisms to help the clinician monitor the status of the patient. In one exemplary embodiment, an alarm can be set to alert the clinician if a specific level of motility was not reached in any of the above measurement techniques. By comparing the measured level of motility with specific targets and patterns, an assessment can be determined and an alarm triggered if the measured motility is to not sufficient. An alarm can take many exemplary forms, such as an audible or visual alert at the nurse's station, a visual alert integrated into the enteral feeding machine, or an alert directly to the clinician via a text message or other electronic messaging technologies.

An exemplary alerting mechanism may combine measured motility data with other measured data, such as heart or respiration data. In this exemplary embodiment, an indication of insufficient motility combined with lower heart and respiratory measurements may indicate the patient's condition is worsening and alert the clinician. In another exemplary embodiment, insufficient motility combined with evidence of esophageal reflux may indicate the patient is not tolerating nutrition and alert the nurse or clinician to adjust care. Specific sensed conditions may initiate additional one time and periodic measurements to better determine the patients' condition. In an exemplary embodiment, detected gastrointestinal motility may initiate more frequent measurements to monitor the patient more frequently and assess the patients' condition. As one example, the device may monitor gastrointestinal motility, heart rate, and other vital signs every 10 minutes, but upon changes in measurements indicating gastrointestinal motility, may increase the frequency of such measurements to better assess gastrointestinal motility. If the subsequent measurements indicate gastrointestinal motility is no longer active, the frequency and type of measurements may be decreased to conserve battery life.

B. Assessing Gastrointestinal Motility Via Substance Indicator(s)

Embodiments are disclosed above that monitor physiological conditions enabling assessment of gastrointestinal motility using accelerometers and/or microphones. However, embodiments are intended to include any useful or beneficial apparatus and methods for diagnosing and monitoring adequate gastrointestinal motility. Thus, other embodiments include any type of sensor enabling monitoring of these physiological conditions, including but not limited to substance indicator(s).

In the related art, an acetaminophen absorption test can be used to assess gastric emptying, but is not practical in routine care. Gastric residuals can be measured, but may be of limited use.

Thus, in one embodiment, a catheter is inserted into the small bowel from the nares. The catheter includes a sensor in the distal tip and a proximal port a certain distance, such as 35 cm, from the distal tip through which an indicator substance can be injected. Alternatively, the indicator substance can be injected into the stomach through any indwelling catheter, e.g., PEG feeding tube. An effective volume (e.g., 20 ml) of the indicator substance is introduced into the stomach. A certain amount, such as a majority, of the indicator substance migrating to the sensor, disposed at a relevant location such as in the small bowel, may evidence adequate gastric motility/emptying.

Embodiments are intended to cover any substance that can operate as the indicator substance disclosed above, such as glucose. Embodiments are also intended to cover other or additional sensors to provide any other useful data. In one such embodiment, a sensor is also provided in the stomach to provide data confirming the amount of indicator substance traveling to the small bowel. In one exemplary embodiment, the amount of indicator substance is measured as the concentration of the substance. In one example, an indicator substance is injected in to the stomach, and a sensor in the stomach measures the concentration of the indicator substance. In this example a second sensor located in the small bowel measures the concentration of the indicator substance. By measuring the differences in concentration and the time elapsed of such measurement differences, it may be possible to assess the relative level of motility of the gastric contents.

Still other embodiments provide additional or alternative types of sensors to supply data for determining motility. In one such embodiment, sensors monitor blood composition to measure amounts of indicator substance introduced into, and absorbed by, the gastrointestinal system, e.g. the small bowel, to determine motility. For example, some substances, such as Tylenol, are only absorbed by the small bowel. Thus, determining the amount of Tylenol absorbed into the patient's blood stream following introduction of a known quantity into the stomach will indicate the quantity of Tylenol passed from the stomach into the small bowel, i.e. gastric motility.

In addition, or as an alternative, to the blood composition sensors disclosed above, other embodiments include vapor sensors that measure quantities of indicator substance in the patient's breath. For example, in order to assess gastric motility an indicator substance that is only absorbed in the small bowel can be introduced into the stomach. If gastric motility is normal, this substance will move into the small bowel, be absorbed in the small bowel, and then be absorbed into blood traveling to the lungs, transferred to air in the lungs at the level of the alveoli and ejected as the patient exhales.

The patient's exhaled breath can then be analyzed to determine the amounts and time course of indicator substance present therein. Poor or absent gastric motility would be manifested by a delay in the time from administration of the indicator substance to first appearance of the indicator substance in the exhaled breath. A reduction in the total quantity of exhaled substance can be assessed in several ways. For example, an Area Under the Curve analysis can be done, with a lower Area Under the Curve value reflecting a reduced level of absorption.

C. Assessing Other Aspects of Gastrointestinal Function Via Accelerometer(s)

Embodiments are disclosed above that monitor physiological conditions enabling assessment of gastrointestinal motility using accelerometers and substance indicators. However, embodiments are intended to cover or otherwise include accelerometers for measuring, directly or indirectly, any physiological condition from which any relevant aspect of gastrointestinal function can be gleaned or condition diagnosed. For example, as disclosed in more detail below, some embodiments include accelerometers to measure vibrations in or around a patient's gastrointestinal system for the purpose of diagnosing various conditions, including but not limited to Small Intestinal Bacterial Overgrowth (SIBO), Irritable Bowel Syndrome (IBS), diarrhea, constipation, malabsorption, etc.

It is normal for the digestive tract to produce gas at various locations and during specific stages of digestion. Many indications such as SIBO, IBS, diarrhea, constipation, and malabsorption are associated with inappropriate bacteria in the digestive tract that produce abnormal amounts of gas. In the study by Lin H C. Small Intestinal Bacterial Overgrowth, A Framework for Understanding Irritable Bowel Syndrome. *JAMA* 2004, August 18; 292:7 ("Lin"), it was noted how excess gas was confirmed in IBS patients via abdominal films, computed tomography of the abdomen and plethysmographic measurements. Lin further described how excess gas is produced due to colonic bacteria being inappropriately located in the small bowel and causing the fermentation of food before it can be naturally absorbed. This inappropriate fermentation creates excess gas excretion such as hydrogen and methane.

An exemplary embodiment of an accelerometer is to measure patterns and frequency of bowel sounds and correlate these sounds with specific indications such as SIBO, IBS, diarrhea, constipation and malabsorption. In an exemplary embodiment, this could be accomplished by the measurement of gas bubble oscillations as described by Liu. The measurement of gas bubbles may vary by indication and/or type of bacteria that is causing the excess gas excretion.

In an exemplary embodiment, these measurements of bowel sounds could be correlated with the results of a hydrogen breath test, which is used to determine a relative amount of bacteria that may be present the GI tract of a patient. In another exemplary embodiment, the measurements of bowel sounds could be correlated with the results of bacterial cultures of various locations in the small bowel. The result is the measurement of bowel sounds in a patient may then be able to help the clinician more quickly and easily identify specific types and quantities of bacteria that may be present in the patient.

X. SENSOR(S) AND SENSOR SYSTEM(S)

Exemplary embodiments are intended to cover any apparatus and/or method for performing operations disclosed in any and all of the above sections, including known, related art and later developed technologies. A few structures are disclosed below for exemplary purposes, and are not intended to be an exhaustive listing of structures covered by the various embodiments.

A. Exemplary Sensor(s), Indicator(s), and Controller(s)

A few exemplary structures are disclosed below, mainly in the context of incline measurement/monitoring. However, this disclosure is merely provided for exemplary purposes, and is not intended to be an indication that embodiments are only directed to incline measurement/monitoring. To the contrary, embodiments are intended to cover or otherwise include any and all of the measurements/monitoring disclosed above, as well as other measurements/monitoring otherwise covered by the above disclosures and/or that would be considered covered by one of ordinary skill in the art.

Numerous different sensors, combined sensor and attachment mechanisms, and indicators/controllers are disclosed below. It is important to note that any and all features of the various embodiments can be added to or otherwise used in the context of other embodiments. For example, a certain disclosed feature of one sensor embodiment can be applied to or used with a different sensor embodiment. As another example, a certain feature of the indicator/controller shown in FIGS. 7-11 can be applied to or otherwise used with the indicator/controllers 8, 20 of FIGS. 12-16. In other words, the following disclosure is intended to cover all possible permutations of combinations of all structures, features and operations disclosed below.

1. Exemplary Sensor(s) and/or Attachment Mechanisms a. Summary

Embodiments are intended to cover or otherwise include incline sensors having any configuration that is relevant or otherwise useful. FIG. 1 is a schematic of an apparatus in accordance with an exemplary embodiment that includes an incline sensor and attachment mechanism to determine an angle of incline of a patient. However, the structures of FIG. 1 are merely provided for exemplary purposes, and are not intended as limiting with regard to methods and apparatus for determining the patient's angle of incline.

Incline sensors in accordance with some embodiments can be used with or otherwise include an attachment mechanism that includes a strip of various lengths, such as substantially elongated strips, that are attachable to patients. For example, the strips of some embodiments are approximately 1-4 cm wide and approximately 10-40 cm long. In some embodiments, the strip is relatively long in length to provide enhanced accuracy. For example, a strip that is relatively short may be affected by body crevices, such as by falling into the crevices and thus providing imprecise measurements, i.e., providing a measurement of the crevice as opposed to the overall body inclination. Contrarily, a sufficiently long strip may bridge and thus be unaffected by such crevices, thereby providing more accurate measurements of overall body inclination.

The incline sensors can be formed integrally or unitarily with all or parts of the attachment mechanism, or alternatively can be formed completely separately from the attachment mechanism such that the sensor and attachment mechanism constitute separate and discrete components.

The incline sensors and/or attachment mechanism can be formed of, or otherwise include, any material that is relevant or otherwise useful. For example, the strip can be formed of a material that is sufficiently rigid to resist or prevent bending under certain conditions. In other words, the material and/or shape of the sensor strip can be selected to provide a desired rigidity to reduce, minimize or prevent the sensor strip from bending to facilitate, enable or insure that the attached incline sensor accurately measures the incline of a relevant body area (e.g., upper abdomen/chest). However, other factors can be used alternatively, or in addition to, the above factors to select the sensor strip material and/or shape.

In some embodiments, various elements of the sensor and/or attachment mechanism can be formed of a material that is amenable to being disposed or otherwise removed after one or a limited number of uses. Disposability of incline sensor element(s) can be advantageous for numerous reasons, such as reducing, minimizing or avoiding the transfer of germs, bacteria, etc., among patients or others in contact with element(s) of the sensors. Various factors enable disposability of sensor element(s), such as cost, ability to replace old element(s) with new element(s), etc. In some such disposable embodiments, the sensor and/or attachment mechanism includes a disposable synthetic resin sheath that covers all or at least some other elements of the sensor during use. In other words, the synthetic resin sheath can be disposed of or otherwise removed after a single, or limited number of, uses, while some or all of the other sensor elements covered by the sheath can be re-usable.

The sensor and/or attachment mechanism can include a material or other apparatus that is attachable to a patient's body, either directly or indirectly. For example, the attachment material/apparatus can be directly attached to the patient's upper abdomen/chest, back, etc., using any attachment method, such as by using a medical grade adhesive, or indirectly attached, such as by being attached to the patient's cloths, such as the patient's hospital gown or other article of clothing.

In some embodiments that directly attach to the patient, it may be useful for the attachment material/apparatus to form a sufficiently strong bond with the patient's body, but then to also be easily removable from the patient's body after use. It may be especially helpful if removal of this attachment material/apparatus can be accomplished with reduced or without patient discomfort, trauma, damage, etc. In some of these embodiments, the attachment material/apparatus includes an adhesive.

Some embodiments that indirectly attach to the patient include more mechanical attachment devices, such as clips. In one such embodiment, a clip at opposite ends of the incline sensor attaches to the patient's hospital gown or other article of clothing. This embodiment may be beneficial for various reasons, including reducing or avoiding skin irritation that may otherwise be caused by extended contact (such as over several days) of an adhesive with the patient's skin, as well as avoiding unintentional removal of the sensor from the patient's body caused by adhesive failure, which may occur due to patient perspiration, adhesive degradation over time, etc.

In another embodiment, the strip/sensor and/or attachment mechanism can be attached to one or more belts or belt-like devices positioned at a relevant body area, e.g., upper abdomen/chest. This type of attachment may be beneficial by reducing, minimizing or avoiding use of an adhesive that could potentially cause skin irritation, and may also be beneficial by reducing, minimizing or avoiding strip/sensor movement that would otherwise be caused by very loose fitting clothing such as a loose fitting hospital gown. Exemplary embodiments are intended to cover any beneficial structure of such belt-like devices. For example, the belt-like devices or belts can be lightweight, with or without elasticity, and/or otherwise structured to reduce, minimize or avoid interference with a patient's ability to breath or other functions. Some belts incorporated into some exemplary embodiments include belts used in related art or commercially available heart rate monitors as well as in fetal heart rate monitoring.

The above embodiments include incline sensors and/or attachment mechanisms that are separate from other structures and devices. However, other embodiments integrate or otherwise combine incline sensors, including any of the incline sensors and/or attachment mechanisms disclosed above, with other apparatus. These embodiments can be advantageous for various reasons. For example, integrating the incline sensors with feeding tubes or other catheters/devices, which are used for purposes related or unrelated to incline sensing, obviates attaching a separate strip to patients.

The combined structures can either be formed by attaching or connecting separate elements, or alternatively a single integrated or even unitary structure. For example, some incline sensors integrate a level or other incline sensing mechanism with a catheter, such as a catheter indwelling in a patient's upper GI tract, e.g., esophagus and/or stomach. In some such embodiments, the incline sensor is integrated into an 18F Salem Sump type nasogastric/orogastric tube. In another embodiment, the incline sensor is integrated into a longer feed tube, e.g., 140 cm, which is positioned with the distal tip in the small intestine, e.g., duodenum. In this embodiment, the incline sensor can be located at any relevant distance, such as approximately 25 cm, proximal to the distal tip to facilitate or ensure proper sensor positioning.

However, the above sensor(s) are merely disclosed for exemplary purposes, and embodiments are not intended to be limiting. For example, embodiments are intended to cover or otherwise include any and all other structures capable of performing operations disclosed herein.

b. Anterior Attachment

FIG. 1 is a schematic of an apparatus in accordance with an exemplary first embodiment that includes an incline sensor and attachment mechanism attached to an anterior portion of a patient to determine an angle of incline of the patient. FIG. 1 shows the combined sensor and attachment mechanism system 1 as being attached to the patient's anterior at the sternum 3.

It may be beneficial to position the combined sensor and attachment mechanism system 1 on the patient so as to extend along the direction of elongation of the sternum 3. The combined sensor and attachment mechanism system 1 can extend along the entire length of the sternum, even projecting beyond the sternum 3, or alternatively only extend along less than the entire length of the sternum 3.

The length of the combined sensor and attachment mechanism may be determined based on various issues, such as patient comfort, accuracy of patient inclination angle measurements, strength of attachment, ease of removal, etc. For example, the accuracy of patient inclination angle measurements may be affected by the length of the combined sensor and attachment mechanism based on the type of sensor or sensing mechanism used. For example, in some embodiments, a sensor or sensing mechanism is attached at or adjacent to opposing longitudinal ends of an elongated attachment mechanism, and the patient's inclination angle is determined based on the differential (such as vertical differential) between the sensors or sending mechanisms. In this case, the length of the attachment mechanism, and thus the distance separating the sensors or sensing mechanisms, affects accuracy of the measurements. To some extent, accuracy in enhanced as the distance between the sensors or sensing elements increases. However, an upper limit of this distance exists, such that an increase beyond the upper limit fails to enhance, and in some cases decreases, accuracy. For example, disposing the sensors or sensing elements at or adjacent opposing ends of the sternum may provide enhanced accuracy, such as for reasons discussed above, i.e., providing a relatively large separation between the sensors while still limiting the sensor placement to locations proximate the patient's bone as opposed to at or near larger areas of soft tissue, etc.

However, in other embodiments, the length of the attachment mechanism may not substantially affect, or have any affect at all, accuracy of patient inclination angle. For example, in some embodiments, inclination angle is not determined based on the differential between multiple sensors or sensing mechanisms. In some of these embodiments, a single accelerometer or multiple accelerometers determine the inclination angle. In one such embodiment, a single accelerometer is disposed in, on, or at the attachment mechanism, such as at a location equidistant or approximately equidistant from opposing longitudinal ends of the attachment mechanism. In this case, the length of the attachment mechanism is determined based on other factors, such as patient comfort, strength of the attachment, ease of removal, etc.

Attaching the sensor and attachment mechanism to the front (anterior) side of the patient, such as at the sternum, may be beneficial by making it more comfortable for the patient (i.e., so that the sensor and attachment mechanism are not disposed between the patient and a surface on which the patient rests, such as a bed, back of a chair, etc.), easier to attach/apply the sensor to the patient, and/or facilitating determinations that the sensor is initially attached (and remains attached) at the correct position. Attaching the sensor and attachment mechanism to the patient's sternum may also be more comfortable, such as by the patient being less aware of its presence, because the sternum constitutes a part of the human anatomy close to the skin and with a decreased amount of soft tissue and nerves therebetween.

This location may also result in more accurate determinations of the patient's incline angle because of its central location relative to the patient's anatomy, i.e., the sternum is at a location that extends along the center of the chest region. In addition, more accurate determinations of the patient's incline angle are provided by virtue of the fact that the sternum constitutes a part of the human anatomy close to the skin (with a decreased amount of soft tissue therebetween) because it constitutes a rather static surface as compared to other parts of the human anatomy. For example, other sections of the patient's body with include larger amounts of soft tissue can be subject to relatively more movement that is not directly related to the patient's angle of inclination, such as based on the patient's breathing, movement of the patient's extremities, etc. Attaching to the sternum may be advantageous in measuring heart rate, respiratory rate, and respiratory depth given the proximal location to the heart and lungs.

Figure 2:
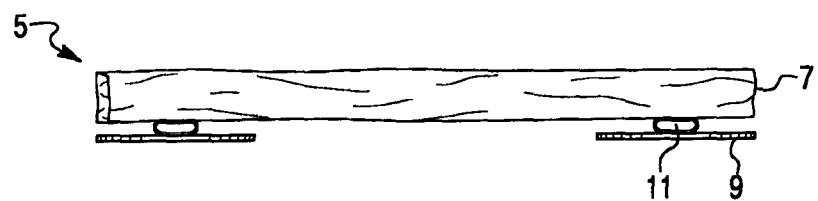
FIG. 2 is a side view of an exemplary attachment mechanism of the apparatus of FIG. 1.

FIG. 2 is a side view of an exemplary attachment mechanism of the apparatus of FIG. 1. As shown in FIG. 2, the attachment mechanism 5 includes a sensor attachment portion 7 for attachment to one or multiple sensors that measure the patient's inclination angle, and a patient attachment portion 9 for attachment to the patient, either directly or indirectly. For example as discussed above, some embodiments attach the attachment mechanism directly to the patient, such as to the patient's skin proximate the sternum, while the attachment mechanism of other embodiments is indirectly attached to the patient, such as to the patient's clothing (e.g., hospital gown). In the embodiment shown in FIG. 2, the patient attachment portion 9 can be directly attached to the patient's skin. The attachment mechanism also includes a connector 11 that connects the sensor attachment portion 7 to the patient attachment portion 9.

Figure 3:
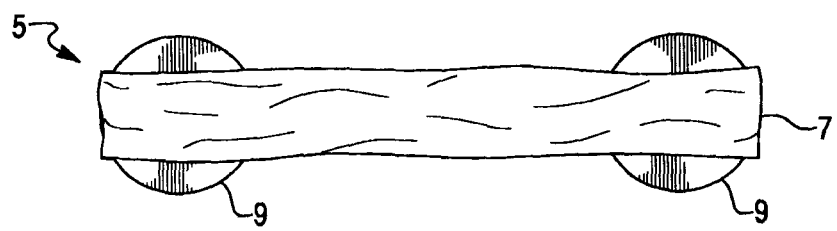
FIG. 3 is a top view of the exemplary attachment mechanism of FIG. 2.

FIG. 3 is a top view of the exemplary attachment mechanism of FIG. 2. As shown in FIG. 3, the patient attachment portion 9 is circular (or substantially circular) and the sensor attachment portion 7 is elongated and rectangular (or substantially rectangular) in top plan view. Alternative exemplary shapes and positioning may be used to achieve the desired results.

The diameter of the patient attachment portion 9 is also greater than the width of the sensor attachment portion 7 in the embodiment shown in FIG. 3, which may be beneficial by increasing the amount of surface contact with the patient, such as with the patient's skin at the sternum, to provide enhanced strength of attachment with the patient. This structure may also be beneficial by reducing the size of the sensor attachment portion 7 in embodiments where the sensor(s) is miniaturized, thus requiring a relatively small surface area of contact between the sensor(s) and the sensor attachment portion 7 to provide sufficient a strength of attachment therebetween. Minimizing surface area can be important since a larger surface area of adhesive can increase risk of a skin reaction to the adhesive.

Figure 4:
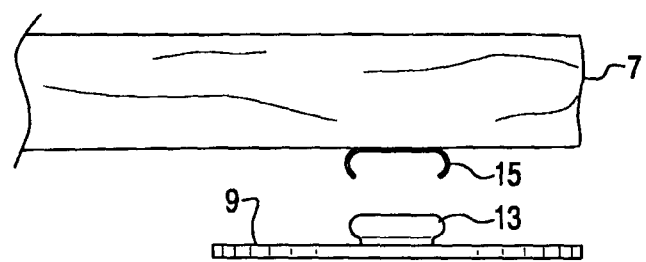
FIG. 4 is a schematic of a portion of the exemplary attachment mechanism of FIGS. 2 and 3.
Figure 4A:
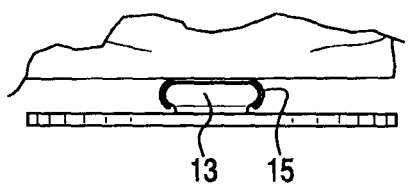

FIG. 4 is a schematic of a portion of the exemplary attachment mechanism of FIGS. 2 and 3, and in particular an exemplary patient attachment portion 9, a portion of an exemplary sensor attachment portion 7, and an exemplary connector 11. In the embodiment of FIG. 4, the connector 11 is in the form of a snap or banana clip, and includes a male portion 13 and a female portion 15. In the embodiment of FIG. 4, the male portion 13 is attached to, integral, or unitary with the patient attachment portion 9, while the female portion 15 is attached to, integral, or unitary with the sensor attachment portion 7. However, these components can be reversed, such that the male portion 13 is attached to, integral, or unitary with the sensor attachment portion 7, while the female portion 15 is attached to, integral, or unitary with the patient attachment portion 9.

However, embodiments are intended to include or to otherwise cover any and all structures and methods to perform the above operations of the attachment mechanism 5, such as to dispose one or multiple sensors at an appropriate location to determine patient inclination angle. For example, the sensor attachment portion 7 can include any structure for providing attachment to one or multiple sensors that measure the patient's inclination angle, and the patient attachment portion 9 can include any structure for providing attachment to the patient, either directly or indirectly. In some embodiments, the patient attachment portion 9 is or includes related art apparatus for attachment to patients, such as for other uses, e.g., EKG also known as ECG.

Similarly, the connector 11 can include any structure for providing a connection between the sensor attachment portion 7 and the patient attachment portion 9. In some embodiments, the connector 11 is or includes related art apparatus providing attachment of similar devices, such as in the context of EKG apparatus.

In fact, two or all of the components of the attachment mechanism 5, i.e., the sensor attachment portion 7, patient attachment portion 9, and connector 11, can be integral or unitary. For example, the entire attachment mechanism 5 can be formed as a single unitary structure.

Figure 5:
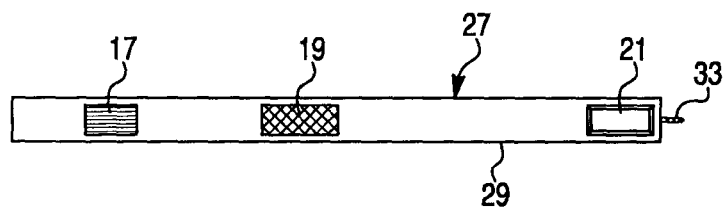
FIG. 5 is a top view of a sensor strip for insertion into the attachment mechanism of FIGS. 2 and 3, the sensor strip including the sensor and other components disposed therein or thereon.

FIG. 5 is a top view of a sensor strip for insertion into the attachment mechanism of FIGS. 2 and 3, the sensor strip including the sensor and other components disposed therein or thereon. The sensor strip 27 includes an elongated housing 29 that houses the sensor 17 and/or additional components therein or thereon. For example, the housing 29 can also house a transmitter and/or receiver 19, a controller 21, etc. Embodiments are intended to cover or otherwise include any apparatus and methods for attaching the sensor 17 and/or other components to the housing 29. For example, the sensor 17 and/or other components may be attached to the housing 29 by glue or epoxy, fitted and disposed within flaps or chambers of the housing 29, etc. The sensor 17 and/or other components may be permanently attached to the housing 29 to form an integral or even unitary structure, or alternatively be removably attached to the housing 29.

The sensor strip 27 may be dimensioned to fit within the sensor attachment portion 7 shown in FIGS. 2, 3 and 6. As discussed in more detail with regard to FIG. 6, the sensor strip 27 may be inserted into the sensor attachment portion 7 via one end of the sensor attachment portion 7. It may also be beneficial for the sensor strip 27 to remain relatively static within the sensor attachment portion 7 for various reasons, such as to enhance accuracy of measurements. Embodiments are intended to cover any apparatus and methods for achieving this substantially static disposition. For example, in some embodiments, the sensor strip 27 fits snugly within the sensor attachment portion 7 so as to remain substantially static therein. In other words, the sensor attachment portion and/or sensor strip 27 can include a mechanism to fix these elements together, such as via Velcro, etc.

In the embodiment shown in FIG. 5, the sensor 17 is shown as being disposed at the left side of the sensor strip 27. However, the sensor can be disposed at any location at, in, or on the sensor strip 27 that enables the patient's inclination angle to be measured.

In some embodiments, the sensor 17 is in the form of an accelerometer, and includes its own power source at the sensor strip 27, such as a battery. In other words, the sensor 17 of these embodiments includes its own self-contained power source. However, in other embodiments, power is supplied to the sensor 17 from a location remote from the sensor 17. For example, the power source, such as a battery, can be disposed at, in, or on another location of the sensor strip 27, and spaced from the sensor 17, such that power is supplied from the battery via wires to the sensor. In some of these embodiments, conductors can be printed on the sensor strip 27 connecting the sensor 17 and the battery. In other embodiments, the power source (which can provide either AC or DC voltage) can be disposed at a location spaced and separate from the sensor strip 27, sensor attachment portion 7, and/or attachment mechanism 5. For example, in some of these embodiments, power can be supplied to the sensor 17 from a power source that supplies power to other medical equipment.

Other components that are related or unrelated to the sensor and its operation can be disposed at, in, or on other locations of the sensor strip 27, sensor attachment portion 7, and/or the attachment mechanism 5, such as at, in or on the sensor attachment portion 7. A few additional components are shown in FIG. 5 for exemplary purposes, and are not intended to be an exhaustive group of components that are envisioned to be covered by the various inventive concepts.

In some embodiments, the transmitter and/or receiver 19 can be disposed at, in or on the sensor strip 27. The transmitter and/or receiver 19 can provide any function or operation that is beneficial. For example, in some embodiments, the transmitter and/or receiver 19 can be structured or otherwise configured to be in communication with the sensor 17 and/or any other components, such as wirelessly or via wires, to receive patient incline angle measurements and transmit them to another device spaced from the combined sensor and attachment mechanism system 1. The controller 21, such as in the form of a microcontroller, can also be provided at, in or on the sensor strip 27. The controller 21 can be structured or otherwise configured to be in communication with the sensor 17 and/or any other components (e.g., transmitter and/or receiver 19), such as wirelessly or via wires, for the purpose of providing or facilitating any beneficial operation, such as controlling the number or rate of patient incline measurements taken by the sensor 17 and transmitted by the transmitter and/or receiver 19.

FIG. 6 is a side view of the attachment mechanism of FIGS. 2-5. As shown in FIG. 6, the sensor attachment portion 7 of the attachment mechanism 5 is hollow, so that various of the component(s) disclosed above can be disposed therein. For example, as discussed with regard to FIG. 5, the sensor strip 27 can be disposed within the sensor attachment portion 7. In the embodiment of FIG. 6, the interior of the hollow sensor attachment portion 7 is accessible, such as by the user (e.g., medical care provider), for any of numerous reasons.

As one example where the sensor attachment portion 7 is disposable, the sensor attachment portion 7 may be structured so that the user can access and remove the sensor strip 27 and/or sensor 17 after use and prior to discarding the sensor attachment portion 7. Disposing of the sensor attachment portion 7 may be beneficial to prevent or reduce the spread of germs, bacteria, etc. among patients because the sensor attachment portion 7 contacts the user, and being able to access and remove the sensor strip 27 and/or sensor 17 enables the sensor strip 27 and/or sensor 17 to be used multiple times and among multiple patients. Disposing the sensor strip 27 and/or sensor 17 within the sensor attachment portion 7 avoids or reduces the spread of germs, bacteria, etc. among patients because the sensor strip 27 and/or sensor 17 is shielded from direct contact with the patient by virtue of it being disposed within the sensor attachment portion 7. It is especially beneficial to reuse the sensor strip 27 and/or sensor 17 because of the relatively high complexity and cost of the sensor strip 27 and/or sensor 17, i.e., reusing the sensor strip 27 and/or sensor 17 (which is some embodiments is the most complex and expensive part of the apparatus) multiple times and among multiple patients saves costs.

The above embodiment only focuses on disposing the sensor strip 27 and/or sensor 17 within the sensor attachment portion 7, however other embodiments dispose any or all of the above or other devices within the sensor attachment portion 7. For example, in the embodiment of FIG. 6, the sensor attachment portion 7 includes a battery receiver 23 that houses a battery. In one such embodiment, the battery receiver 23 includes a female receiver 31 that communicates with a male end 33 at the end of the sensor strip 27. The battery disposed within the battery receiver is in electrical communication with the male end 33 via the female receiver 31, which is wired or otherwise in electrical communication with other electronic components at the sensor strip 27 so that the battery by virtue of being connected to the male end 33 supplies power to the electronic components at the sensor strip 27.

It may be especially beneficial for the sensor attachment portion 7 to include the battery receiver 23 and thus the battery for a variety of reasons. For example, the sensor attachment portion 7, as well as the battery disposed therein, are disposable. The sensor attachment portion 7 and battery are configured to be manufactured at low cost, and thus disposability after each use is not financially significant. Disposability of these components is also beneficial because it ensures that fresh or previously unused sensor attachment portions 7 and batteries are provided for patients to initiate monitoring. Thus, users, such as medical care providers, are not burdened with battery replacement, which reduces their workload. In many cases, use of the sensor attachment portion terminates before the battery fails, and the package (sensor attachment portion 7 and battery) are discarded.

However, other embodiments provide more accessibility to the battery. For example, some embodiments are configured to enable a user, such as a medical care provider, to insert a battery into the sensor attachment portion 7. This operation can be performed prior to the first use of the sensor attachment portion, i.e., where the user inserts the battery into the sensor attachment portion prior to its first use. In this case, the battery can be provided in the same packaging as the sensor attachment portion, however, in some embodiments, the battery can be provided completely separate from the sensor attachment portion 7 packaging. Alternatively or additionally, the sensor attachment portion 7 can be configured for battery replacement, i.e., to facilitate removal of an existing battery (such as in the case where the existing battery is out or low in charge) and insertion of a new or fresh battery.

An alternative exemplary embodiment for attaching the battery would be to have an alternatively designed sensor strip 27 that contains an integrated placement of the battery via an integrated battery receiver 23. In this embodiment, the battery receiver 23 is not located in sensor attachment portion 7, but instead is located in sensor strip 27. Locating the battery in sensor strip 27 may be advantageous in simplifying the design and lowering the cost of the sensor attachment portion 7. This exemplary alternative location for the battery may also allow the use of different materials for the sensor attachment portion 7.

Embodiments are intended to include or otherwise cover any apparatus or method of disposing and/or accessing the sensor strip 27, sensor and/or other components within the sensor attachment portion 7. The embodiment shown in FIG. 6 includes a pivoting arm 25 that provides access to the interior of the sensor attachment portion 7. For example, one end of the arm 25 is attached to the sensor attachment portion 7 so as to be pivotable thereabout such as at an upper corner or surface of the sensor attachment portion 7, while the opposing end of the arm 25 is removably attachable a bottom or lower surface of the sensor attachment portion 7. Any apparatus or method can be used to removably attach the opposing end of the arm 25 to the bottom or lower surface of the sensor attachment portion 7, such as Velcro, snaps, adhesive, folds in the material, buttons, etc.

The combined sensor and attachment mechanism system 1 or any components thereof (such as the sensor 17) can be directly or indirectly connected to any of the indicators/controllers disclosed herein to assess, manipulate or otherwise use the data provided by the sensor 17. For example, in some embodiments, the indicator/controller indicates an angle of inclination of the patient with respect to the floor or other relevant surface. The indicator/controller can be located at the combined sensor and attachment mechanism system 1, proximate the patient, or remote from the patient, such as at a nurse's station, central monitoring station, etc.

As indicated above, embodiments are intended to include or otherwise cover any apparatus or method of attaching the sensor to the attachment mechanism. As one example, FIG. 6 shows a sensor attachment portion 7 that is entirely or substantially entirely hollow to enable any number of devices, including the sensor 17, to be disposed therein. However, embodiments are intended to cover any number of alternative structures. For example, in one alternative embodiment, instead of disposing the sensor strip 27 within the sensor attachment portion 7, the sensor strip 27, sensor 17 and/or other device is disposed in a pouch defined at the top outer surface of the sensor attachment portion 17. In some such embodiments, the pouch is sized to retain the sensor strip 27, sensor 17 and/or other device in a static or substantially static condition relative to the sensor attachment portion 7. For example, the pouch can be provided in a size to define a space that is only slightly greater than the size of the sensor strip 17, sensor 17 and/or other device so that the sensor 17 or other device fits snugly therein and thereby is retained in a static or substantially static condition relative of the sensor attachment portion 7. In some such embodiments, the sensor attachment portion 7 is made of a material, such as certain synthetic resins, that deform to facilitate this snug fit.

c. Posterior Portion Attachment

FIG. 12 is a schematic of an apparatus that includes a second exemplary embodiment of an incline sensor and attachment mechanism attached to a posterior of a patient to determine an angle of incline of the patient, and a second exemplary embodiment of an indicator and/or controller relating to the patient inclination angle as well as any other data and operations that may be beneficial and/or otherwise useful. The alternative embodiment shown in FIG. 12 is merely shown for exemplary purposes, and is not intended as an indication of all alternatives covered by the scope of the present invention. In fact, other embodiments cover various other related and/or unrelated aspects of patient incline monitoring.

As one example, FIG. 12 shows a patient 2 lying on a hospital bed 112. An exemplary strip-shaped incline sensor and/or attachment mechanism 114 is provided at the patient's back, such that a top end 116 of the sensor/attachment mechanism is disposed at or approximately at the patient's sternal notch, and a bottom end 118 of the sensor/attachment mechanism is provided at or approximately at a location proximate or otherwise corresponding to the patient's umbilicus.

The sensor/attachment mechanism can be attached to the back (posterior) side of the patient (as described above and shown in FIG. 12), or in some patients it may be beneficial for the sensor to be attached to the front (anterior) side of the patient (as shown in FIG. 1). However, embodiments are intended to cover attachment at any other or additional location at or on a patient. Attaching the sensor/attachment mechanism to the patient's back as shown in FIG. 1 may be beneficial in providing accurate patient incline angle data. However, as indicated above, attaching the sensor/attachment mechanism to the front (anterior) side of the patient may be relatively beneficial by making it more comfortable for the patient, easier to attach/apply the sensor/attachment mechanism to the patient, and/or facilitating determinations that the sensor/attachment mechanism is initially attached (and remains attached) at the correct position. The anterior (front) side of the patient, specifically on the sternum, may be particularly beneficial to patients who are obese since this sternum area often contains less fat and thus may provide a more consistent attachment point and measurement readings. In fact, the sensor and/or attachment mechanism 114 shown in FIG. 12 can alternatively be attached to a patient's anterior.

As with the previously disclosed embodiments, the sensor/attachment mechanism 114 of the embodiment shown in FIG. 12 can be connected to any of the indicators/controllers disclosed herein to assess, manipulate or otherwise use the data provided by the sensor. For example, in some embodiments, the indicator/controller indicates a relative angle defined between a line connecting the sensor top and bottom ends 116, 118, with respect to the floor. The indicator/controller can be located at the sensor 114, proximate the patient, or remote from the patient, such as at a nurse's station, central monitoring station, etc.

Some exemplary indicators/controllers are disclosed below for exemplary purposes, and are not intended to be limiting. In fact, embodiments are intended to cover or otherwise include any beneficial or useful indicator/controller configuration and/or operation.

2. Exemplary Indicator(s)/Controller(s)

Figure 7:
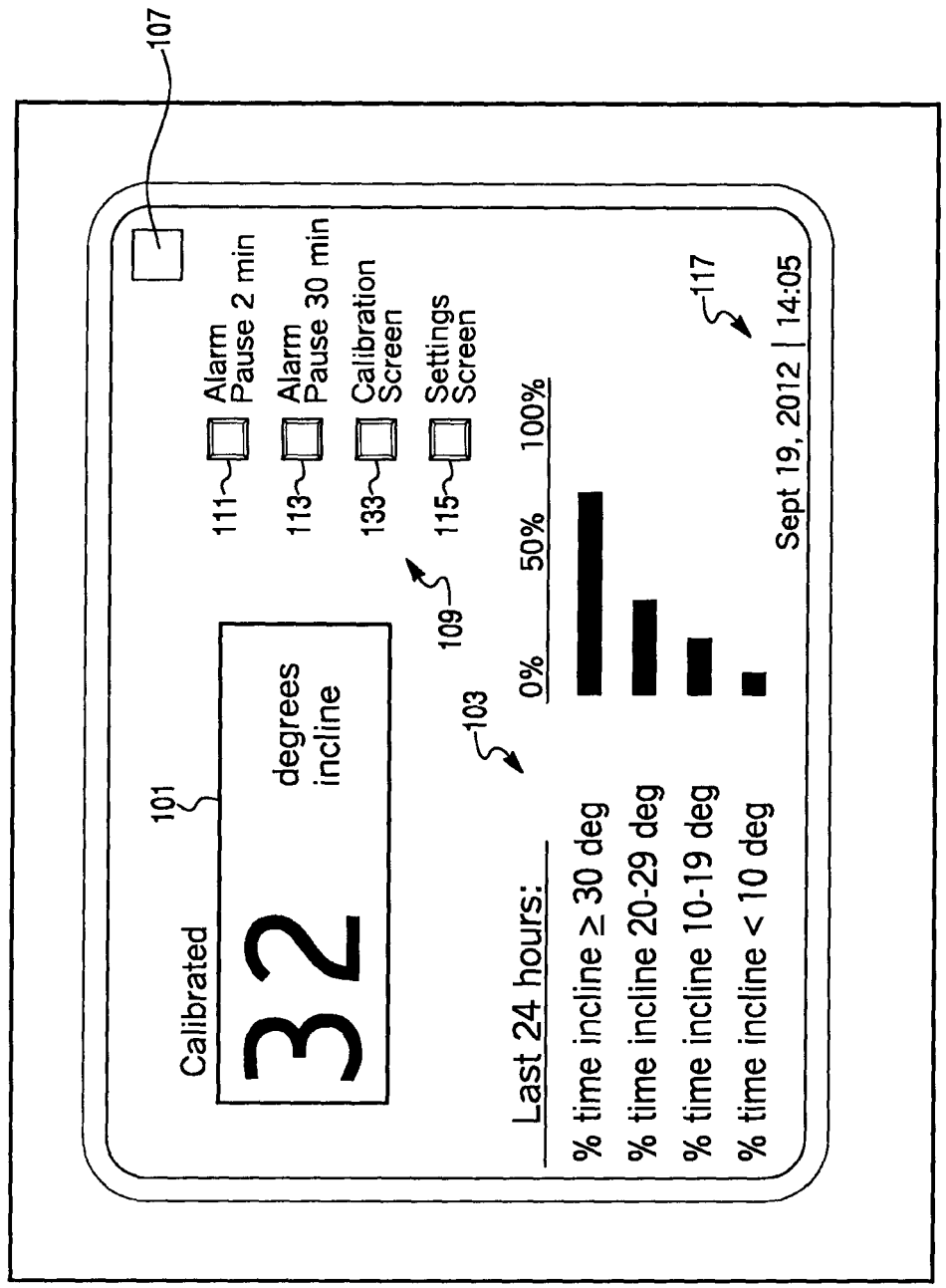
FIG. 7 is a schematic of a main or default screen of a first exemplary embodiment of an indicator and/or controller in accordance with an exemplary first embodiment.

FIG. 7 is a schematic of a main or default screen (hereinafter main screen) of a first exemplary embodiment of an indicator and/or controller (hereinafter indicator/controller) in accordance with an exemplary first embodiment. The main screen, which is discussed in more detail below, is merely provided for exemplary purposes and is not intended to be limiting or indicative of the only such manner of indication provided by the various embodiments. To the contrary, embodiments are intended to include or otherwise cover any manner or expression of indication that is beneficial or otherwise useful.

In addition, embodiments are intended to include or otherwise cover any known, related art, and/or later developed apparatus or technologies for providing the relevant indications to the user, such as a medical care provider. For example, in some embodiments, the indications are provided on a computer screen, such as at a hospital nurse's station, on a portable display apparatus PDA) utilizing touch screen display, on the combined sensor and attachment mechanism system 1 itself, etc. Further, embodiments are intended to include or otherwise cover any apparatus or method of communication between the combined sensor and attachment mechanism system 1 and the indicator/controller, including wires, wireless technologies, etc.

In the embodiment shown in FIG. 7, the indicator/controller provides an indication of the patient's current angle of inclination in region 101, which is shown as being 32 degrees. It may be beneficial for region 101 to be configured so as to prominently display or otherwise indicate to the user (e.g., medical care provider) the current angle of inclination, which may be the primary or significant focus of some embodiments. Region 101 shown in FIG. 7 therefore displays the current inclination angle in relatively large print in generally the upper left portion of the indicator/controller.

The main screen of the indicator/controller can be configured to include any other information that may be relevant or otherwise useful for monitoring incline angles, or any other purpose unrelated to incline angles. As one example, the main screen of FIG. 7 includes a region 117 that provides the current date and time. However, other embodiments include alternative or additional dates and/or times, such as the date and/or time of initiation of monitoring, date and/or time of cessation of monitoring, etc.

The main screen of the indicator/controller shown in FIG. 7 also includes region 103 that provides an indication of the history of the patient's inclination angle, such as over a period covering the previous 24 hours. However, this exemplary historical period is merely provided for exemplary purposes, and embodiments are intended to include or otherwise cover any useful historical period, which may be dependent on the type of care or condition that is relevant to the monitoring of the inclination angle (i.e., the reason or purpose of the monitoring).

In region 102, the historical inclination angles are provided in the following increments: 1) less than 10 degrees; 2) 10-19 degrees; 3) 20-29 degrees; 4) greater than or equal to 30 degrees. However, these increments are merely provided for exemplary purposes, and embodiments are intended to include or otherwise cover any number of increments or magnitude of increments. For example, the number and magnitude of increments may be selected based on the type of care or condition that is relevant to the inclination angle monitoring being performed, i.e., the purpose or reason for the inclination angle monitoring.

In fact, in some embodiments, the indicator/controller is configured so that the user, e.g., health care provider, can set the number and magnitude of increments. In some of these embodiments, the user, e.g., health care provider, can enter the relevant patient condition, such as the patient receiving enteral feeding, and the indicator/controller is configured to automatically display a recommended number and magnitude of increments. Further, in some of these or other embodiments, the user can then modify the automatically displayed number and magnitude of increments.

In the embodiment shown in FIG. 7, the patient's inclination angle history is provided in the form of a bar graph based on percentage of time over the historical period, i.e., the patient's inclination angle was 20-29 degrees for approximately 25% of the previous 24 hours, the patient's inclination angle was less than 10 degrees for approximately 5% of the previous 24 hours, etc. However, the manner or type of expression shown in FIG. 7 is merely provided for exemplary purposes, and embodiments are intended to include or otherwise cover any type or manner or type of expression of this historical information, such as via indicating exact numerical percentages for the displayed increments (i.e., the patient's inclination angle was 20-29 degrees for exactly 26.7% of the previous 24 hours), a pie graph, a chart, such as with the x-axis representing inclination angle and the y-axis representing time, etc.

The indicator/controller can be configured to provide any type or manner of expression of this historical information. For example, the indicator/controller can display a certain type or manner of expression of this historical information based on the user's entry of the relevant patient condition, such as the patient receiving enteral feeding. In some of these or other embodiments, the user can then modify or change the automatically displayed type or manner of expression of this historical information.

In some embodiments, the indicator/controller is configured to provide additional detailed information relevant to certain increments. For example, in some of these embodiments, a user can select a certain increment, such as the increment of 20-29 degrees, and the indicator/controller is configured to display additional information relevant to that period, such as the times of day that the patient's inclination angle was in that range, a more detailed breakdown of inclination angles and times for that range, etc. This feature may be especially beneficial when monitoring certain medical conditions, such as conditions where certain inclination angles are very relevant, e.g., in the context of enteral feeding.

In fact, the embodiment shown in FIG. 7 includes a visual blinking alert/alarm 107 that provides the user, e.g., medical care provider with an indication of certain significant or otherwise relevant events. For example, in the above example where it is very important for the patient's inclination angle to never fall below 10 degrees during enteral feeding, the indicator/controller can be configured to activate the visual blinking alert/alarm 107 so that the user becomes aware of the fact that the patient is or has been at an incline of less than 10 degrees. This feature may be especially beneficial, such as by prompting the user to take steps to correct the patient's inclination angle. However, the visual blinking alert/alarm 107 is merely provided for exemplary purposes, and embodiments are intended to include or otherwise cover alternative or additional types of alarms, including but not limited to other types of alarm indicators, such as known, related art and/or later developed visual, audible, vibration, etc. indicators at any location, such as proximate the patient, at a location remote from the patient (e.g., nurses' station), etc.

The main screen of the indicator/controller can be configured to include a region 109 that enables the user to control certain other aspects of the inclination angle monitoring. Certain of these aspects are merely shown in FIG. 7 for exemplary purposes, and embodiments are intended to enable the user to control any relevant aspect of the inclination angle monitoring.

For example, the embodiment shown in FIG. 7 enables the user to pause the alarm for certain periods. Embodiments are intended to provide any pausing type operation that is relevant to the incline monitoring and/or any other reason, such as to disengage the incline monitoring for a specified or unspecified period. This type of pausing operation can be beneficial for numerous reasons, such as in situations where the patient needs to be moved, the patient's needs to be reoriented, some other event occurs that would cause an aberration in the incline data, etc. For example, pausing the incline monitoring in these situations prevents the historical data from being affected and thereby corrupted by incline data generated while the patient is being moved, reoriented, etc. Pausing the incline monitoring in these situations also prevents the alarm, such as the visual blinking alert/alarm 107, from being activated, which would be unnecessary for certain embodiments. For example, in embodiments where an alarm is activated if the patient's angle varies within a certain number of degrees (such as 10 degrees) from a 30 degree incline, it would be unhelpful and even disadvantageous (such as by being distracting) for the alarm to be activated in situations where the patient is being moved, reoriented, etc. by medical care providers.

A first actuator 111 enables the alarm to be paused for a relatively short specified period, e.g., 2 minutes. Thus, actuation of the first actuator 111 disengages the alarm, compilation of incline data, and/or incline monitoring itself, for a 2 minute period. Pausing the system in this manner for a relatively short period may be advantageous in situations where the patient is being manipulated in a manner that would cause an aberration in the incline data, needlessly actuate the alarm, etc. for a brief period, such as in situations where a caregiver needs to reorient the patient, briefly remove the patient from a hospital bed, etc.

A second actuator 113 enables the alarm to be paused for a relatively longer specified period, e.g., 30 minutes. Thus, actuation of the second actuator 113 disengages the alarm, compilation of incline data, and/or incline monitoring itself, for a 30 minute period. Pausing the system in this manner for a relatively longer period may be advantageous in situations where the patient is being manipulated in a manner that would cause an aberration in the incline data, needlessly actuate the alarm, etc. for a relatively longer period, such as in situations where a caregiver needs to remove the patient from a hospital bed such as for testing, etc.

Figure 8:
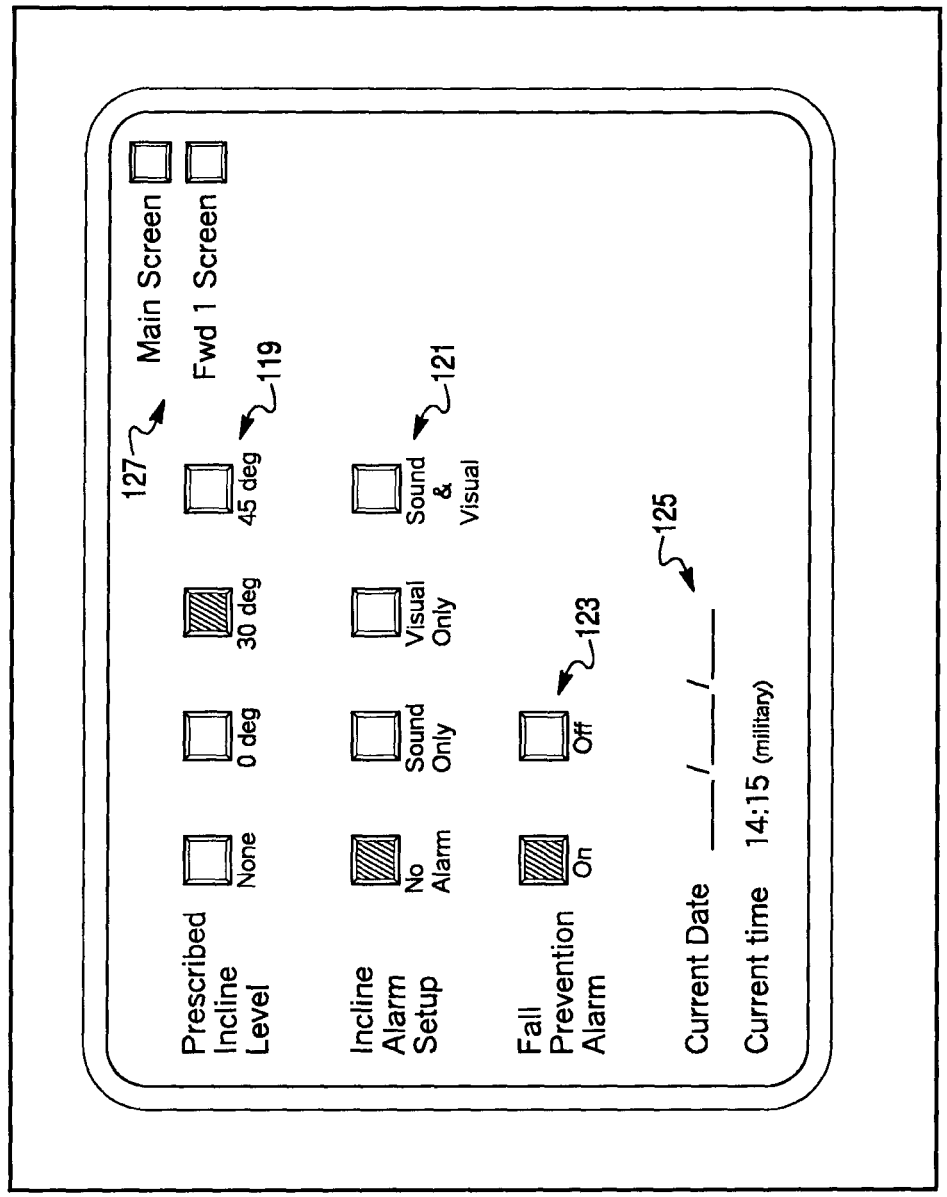
FIG. 8 is a schematic of a general settings screen of the exemplary indicator and/or controller of FIG. 7.

A settings prompt 115 enables the user, such as a medical care provider, to manipulate or set various settings of the indicator/controller or other operations relevant to the incline monitoring. In the embodiment shown in FIG. 7, actuation of the settings actuator 115 causes a settings screen to display, such as the settings screen of FIG. 8, which is a schematic of a general settings screen of the exemplary indicator and/or controller of FIG. 7. The settings shown in FIG. 8 are merely provided for exemplary purposes, and embodiments are intended to include or otherwise cover any settings that may be beneficial or useful to incline monitoring, or other settings unrelated to incline monitoring. In fact, in other embodiments, settings can be manipulated by the user via the main screen or via any other method.

In the embodiment of FIG. 8, the settings screen includes a region 119 that enables the user to set a prescribed incline level. This feature may be especially beneficial in situations where it is relevant for the patient to be disposed at a certain inclination angle, above or below a certain inclination angle, within a certain range of inclination angles, etc. The user is provided with the following inclination angle choices: none, 0 degrees, 30 degrees, and 45 degrees. The user can either overtly select one of the choices, or the indicator/controller can automatically provide a default setting. The setting for 30 degrees is shown as either being selected by the user or resulting from the default setting, which causes the indicator/controller to perform operations based on this angle. However, in other embodiments, the indicator/controller is configured to enable the user to set the exact incline angle desired, instead of being provided with a finite number of choices. In fact, embodiments are intended to include indicators/controllers and sensors that provide any level of precision for the incline angle monitoring and processing, such as in the range of single degrees, tenths of degrees, hundredths of degrees, etc.

Exemplary operations performed by the indicator/controller that are relevant to the inclination angle setting include actuating the alarm 111 should the patient's inclination angle: 1) vary from the set angle, 2) vary from the set angle by a certain amount (i.e., deviate from 30 degrees by more than 5 degrees), 3) exceed or fall below the set angle, exceed or fall below the set angle by a certain amount, etc. The indicator/controller can be configured to automatically perform the desired operation based on selected incline angle, or configured to enable the user to choose the desired operation.

The settings screen shown in FIG. 8 also includes a region 121 that enables the user to set the type of alarm actuation. For example, the user can be provided with the following alarm options: 1) no alarm, 2) sound only, 3) visual only, and 4) sound and visual. The user can either overtly select one of the choices, or the indicator/controller can automatically provide a default setting. However, these alarm choices are merely provided from exemplary purposes, and embodiments are intended to include or otherwise cover any type or manner or alarm that is beneficial or useful for inclination angle monitoring or for any other purpose. In the embodiment of FIG. 8, the no alarm setting is shown as either being selected by the user or resulting from the default setting.

The settings screen can also include a region 123 that enables the user to activate or deactivate a fall prevention alarm, and the indicator/controller can be configured to monitor the incline angle or other movements of the patient that may precede the patient falling. I the embodiment shown in FIG. 8, the fall prevention alarm is activated.

The fall prevention alarm may be duplicative or completely separate from the alarm discussed above. In other words, the fall prevention alarm can be based on the same or different conditions that result in activation of the alarm upon deviation from the incline angle set in region 119, and the same or different alarm indicators can also be used. In some embodiments, the fall prevention alarm is activated by similar conditions as the alarm based on deviation from the incline angle set in region 119. For example, the indicator/controller may be configured such that the alarm based on deviation from the incline angle set in region 119 may be activated if the patient's incline angle falls below a 30 degree incline, while the fall prevention alarm may be activated if the patient's incline angle rises above 60 degrees incline. In addition, the type or manner of alarm may be different, such that the medical care provider can determine or quickly perceive which of the above two conditions has occurred.

The settings screen can include any other information or data that is useful or beneficial for incline monitoring of for any other purpose. For example, the embodiment of FIG. 8 includes a region that provides the current date and time. However, other embodiments include alternative or additional dates and/or times, such as the date and/or time of initiation of monitoring, date and/or time of cessation of monitoring, date and/or time of the previous alarm activation, etc.

The setting screen, and/or any of the other screens provided by the indicator/controller, can include a region 127 that enables a user to more easily navigate the multiple screens. In the embodiment shown in FIG. 8, region 127 includes a main screen prompt that enables the user to navigate directly to the main screen, and/or a forward 1 screen prompt that enables the user to navigate directly to the next subsequent screen. However, embodiments are intended to include or otherwise cover any known, related art and/or later developed apparatus or methods that facilitate a user's navigation among the various operations, settings, etc. of the indicator/controller.

Alternative or additional settings can be provided via any number of additional screens. For example, the embodiment shown in FIG. 9 includes one such additional screen, and in particular is a schematic of a separate alarm volume settings screen of the exemplary indicator/controller of FIGS. 7 and 8. The additional settings screen of FIG. 9 can be provided to the user via any apparatus or method, such as the user actuating the forward 1 screen prompt in region 127 of FIG. 8.

Figure 9:
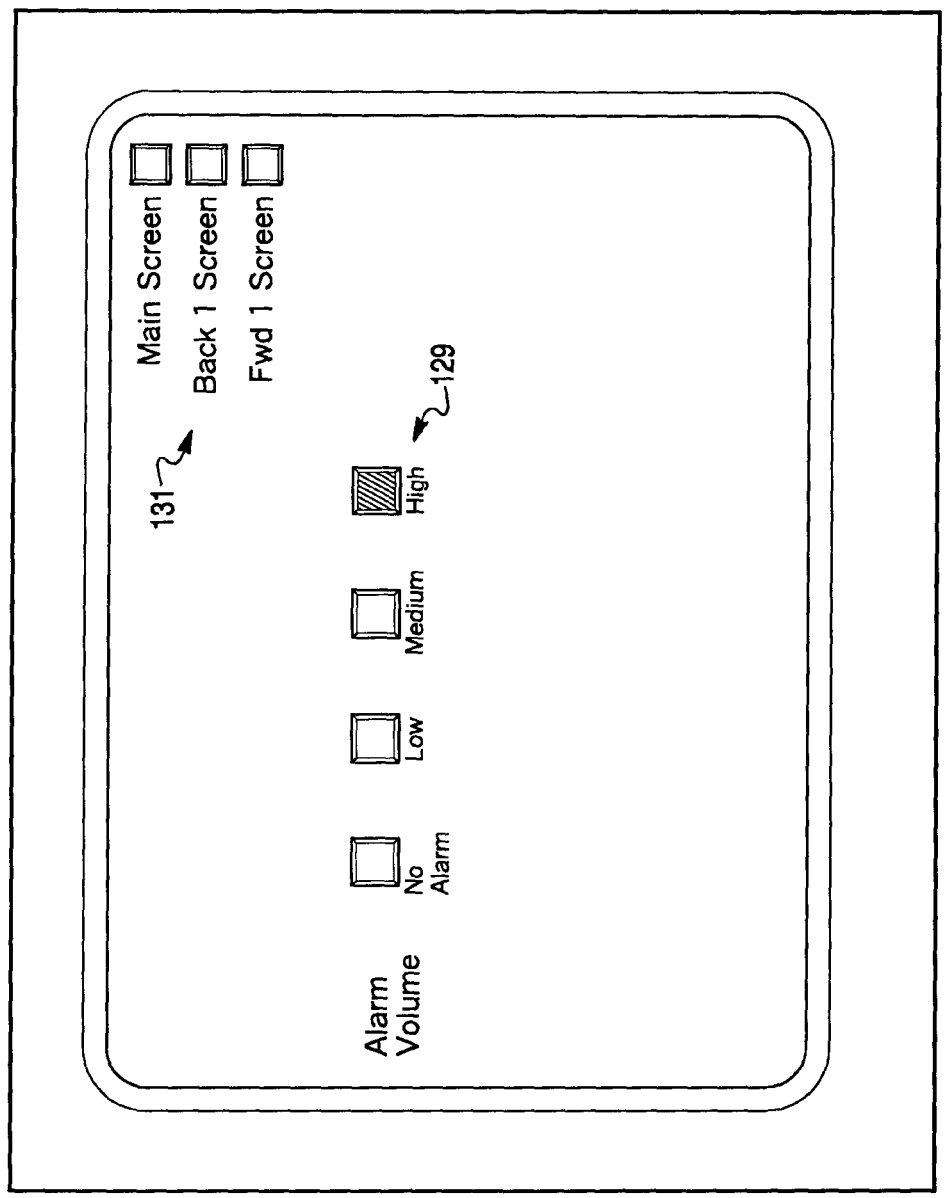
FIG. 9 is a schematic of a separate alarm volume settings screen of the exemplary indicator and/or controller of FIGS. 7 and 8.

The alarm volume settings screen of FIG. 9 includes a region 129 that enables the user to set the alarm volume, including but not limited to the alarm based on deviation from the incline angle set in region 119 and/or the fall prevention alarm. The user can be provided with a number of volume options, including: 1) no alarm, 2) low, 3) medium, and 4) high. However, embodiments are intended to include or otherwise cover any beneficial or useful variation in alarm volume settings. In addition, the indicator/controller can be configured to provide a default alarm volume setting. In the embodiment shown in FIG. 9, the alarm volume setting is high.

The alarm volume setting screen can also include a region 131 that enables a user to more easily navigate the multiple screens. In the embodiment shown in FIG. 9, region 131 includes a main screen prompt that enables the user to navigate directly to the main screen, a back 1 screen prompt that enables the user to navigate directly to the immediately previous screen, and/or a forward 1 screen prompt that enables the user to navigate directly to the next subsequent screen.

The indicator/controller can be configured to provide calibration operations relating to the patient incline measurements. Embodiments are intended to include or otherwise cover any type or manner of calibration that is relevant or useful to the incline measurements. For example, some embodiments are directed to enhancing accuracy of incline measurements, and in particular addressing the difficulty in accurately determining incline measurements based on differences among various patients, such as different body types, genders, weights, and/or other characteristics.

As discussed in more detail below, in some embodiments, the patient is directed to lie in a flat supine position with the combined sensor and attachment mechanism 1 attached to the patient's chest, and the resulting sensor incline measurement is calibrated as 0 degrees. The patient is then instructed to either assume a fully erect seated position or to stand if possible, each with the patient's back extending in a vertical direction, and the resulting sensor measurement is calibrated as 90 degrees.

Figure 10:
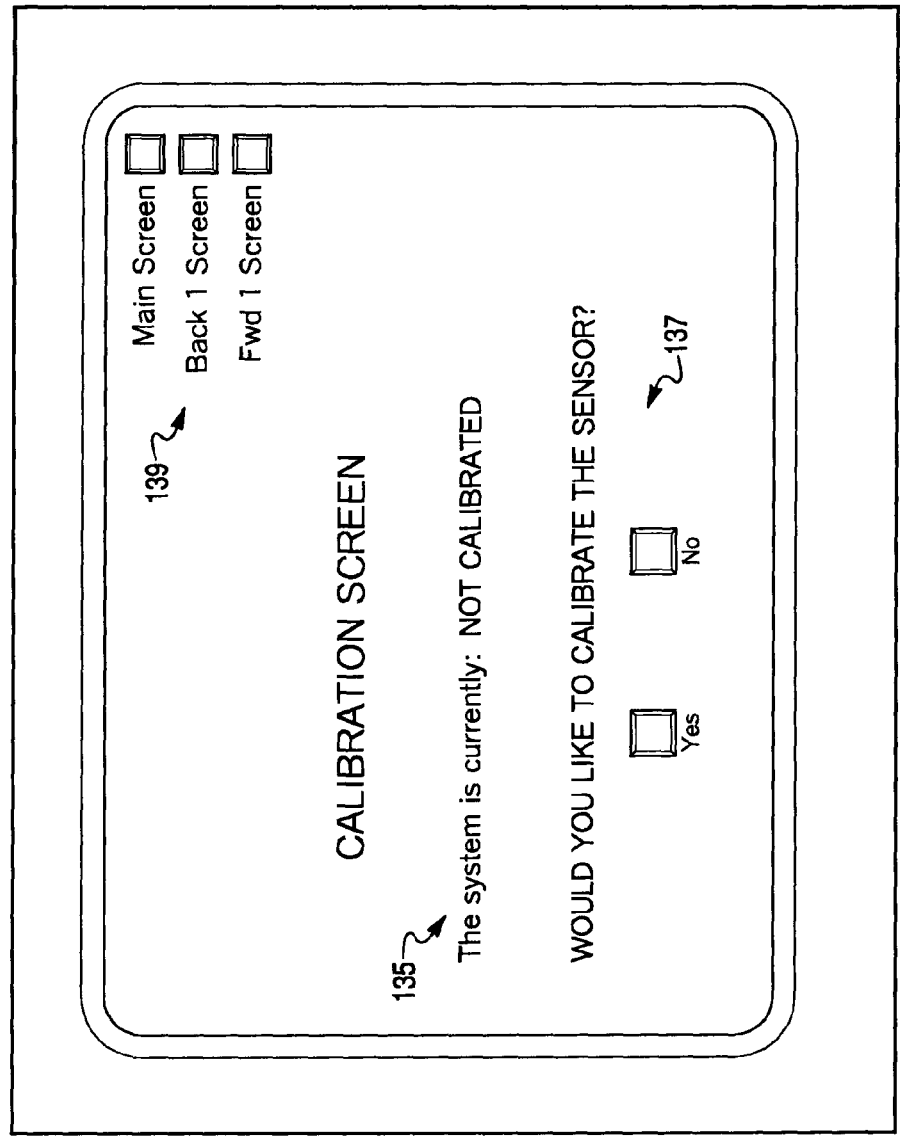
FIG. 10 is a schematic of a first calibration screen of the exemplary indicator and/or controller of FIGS. 7-9.

In the embodiment of FIG. 7, region 109 includes a calibration prompt 133 that enables the user, such as a medical care provider, to set or otherwise engage in calibration operations relevant to the incline monitoring. In the embodiment shown in FIG. 7, actuation of the calibration prompt causes a calibration screen to display, such as the calibration screen of FIG. 10, which is a schematic of a first calibration screen of the exemplary indicator and/or controller of FIGS. 7-9. However, the calibration operations, prompts, etc. shown in FIG. 10 are merely provided for exemplary purposes, and embodiments are intended to include or otherwise cover any calibration operations, prompts, etc. that may be beneficial or useful to incline monitoring, or other settings unrelated to incline monitoring. In fact, in other embodiments, calibrations operations, prompts, etc. can be manipulated by the user via the main screen or via any other method.

The embodiment shown in FIG. 10 includes a region 135 that indicates whether the combined sensor and attachment mechanism 1, indicator/controller, and/or any other relevant apparatus (system) is currently calibrated. In the embodiment shown in FIG. 10, region 135 indicates that the system is currently not calibrated.

The embodiment shown in FIG. 10 also includes a region 137 that enables the user to change the system's calibration status. In this embodiment, region 137 is labeled "WOULD YOU LIKE TO CALIBRATE THE SENSOR?" and provides "YES" and "NO" actuators to enable the user to enter the desired instruction. For example, if the system is currently not calibrated (i.e., region 135 indicates "NOT CALIBRATED" as shown in FIG. 10), then the user can select the "YES" actuator in region 137 to instruct the indicator/controller to begin calibration operations or otherwise indicate the user's willingness or desire to calibrate the system. Alternatively, if the system is currently calibrated (i.e., region 135 indicates "CALIBRATED," which is not shown in FIG. 10), then the user can select the "NO" actuator in region 137 to instruct the indicator/controller to remove the current calibration or cease calibration operations if such operations are underway (or otherwise indicate the user's willingness or desire to remove the current calibration or cease calibration operations).

Removal of the current calibration enables a new calibration to be set. In the case where the current calibration is removed, the indicator/controller can either delete the removed calibration or save the removed calibration. In situations where the removed calibration is saved, the indicator/controller can enable a user to identify the saved calibration, such as by identifying the saved calibration using a patient's name or unique medical record number, which provides the opportunity for the user to later reinstall or reactivate the saved calibration.

This feature may be especially beneficial in situations where the system and/or components thereof are used to measure incline angles of multiple patients, and also incline angles of at one of the patients on multiple occasions. Once a calibration is set and saved for an identified patient, the calibration can be removed and recalibrated so that the system can then be used for other patient(s). The system can subsequently be used for the identified patient by recalling or otherwise reapplying the identified saved calibration, thereby obviating the calibration process for the identified patient. In other words, the calibration process only needs to be performed once per patient, which saves the user time each time at initiation of the incline monitoring.

The calibration screen of FIG. 10 also includes a region 139 that enables a user to more easily navigate the multiple screens. In the embodiment shown in FIG. 10, region 139 includes a main screen prompt that enables the user to navigate directly to the main screen, a back 1 screen prompt that enables the user to navigate directly to the immediately previous screen, and/or a forward 1 screen prompt that enables the user to navigate directly to the next subsequent screen.

Figure 11:
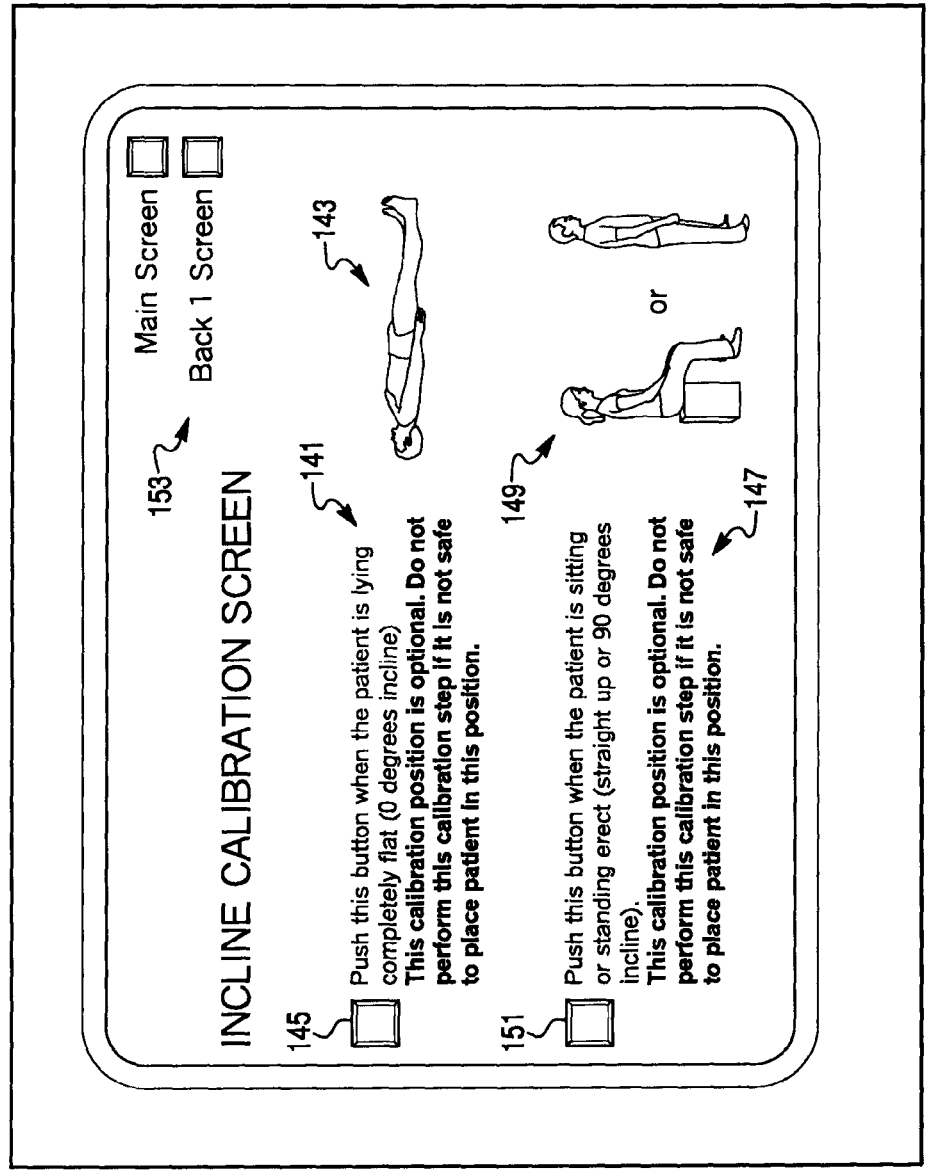
FIG. 11 is a schematic of a second calibration screen of the exemplary indicator and/or controller of FIGS. 7-10.

Selection of either the forward 1 screen prompt or the "YES" actuator in region 137 instructs the indicator/controller to begin calibration operations or otherwise indicate the user's willingness or desire to calibrate the system, by providing the user with access to the second calibration screen of FIG. 11, i.e., FIG. 11 is a schematic of a second calibration screen of the exemplary indicator and/or controller of FIGS. 7-10. As shown in FIG. 11, calibration can be performed via either a one or multiple step process.

As one optional step, the calibration screen of FIG. 11 is provided with a region 141 that enables calibration based on a user assuming a supine position. An example of the recommended patient supine position is shown in region 143 adjacent to region 141 for reference by the user and/or patient. In accordance with this calibration operation, a patient assumes a supine position (as shown in region 143), and the user actuates a supine calibration actuator 145 while the patient is in the supine position. The indicator/controller than calibrates that patient position as being 0 degrees.

An alternative or additional region 147 is provided to enable calibration based on a user assuming an erect sitting or standing position. Examples of the recommended patient erect sitting or standing position are shown in region 149 adjacent to region 147 for reference by the user and/or patient. In accordance with this calibration operation, a patient assumes an erect position (as shown in region 149), and the user actuates an erect calibration actuator 151 while the patient is in the supine position. The indicator/controller than calibrates that patient position as being 90 degrees.

Performing both the supine and erect calibrations may be beneficial by providing enhanced calibration accuracy. However, some patients may not be able to assume one of the designated positions, i.e., either the supine position or one of the erect positions, and thus configuring the indicator/controller to perform the calibration based on only one of these positions is beneficial by enabling calibration for these patients.

The second calibration screen of FIG. 11 also includes a region 153 that enables a user to more easily navigate the multiple screens. In the embodiment shown in FIG. 11, region 153 includes a main screen prompt that enables the user to navigate directly to the main screen, and a back 1 screen prompt that enables the user to navigate directly to the immediately previous screen.

3. Alternative Exemplary Indicator(s)/Controller(s)

Figure 13:
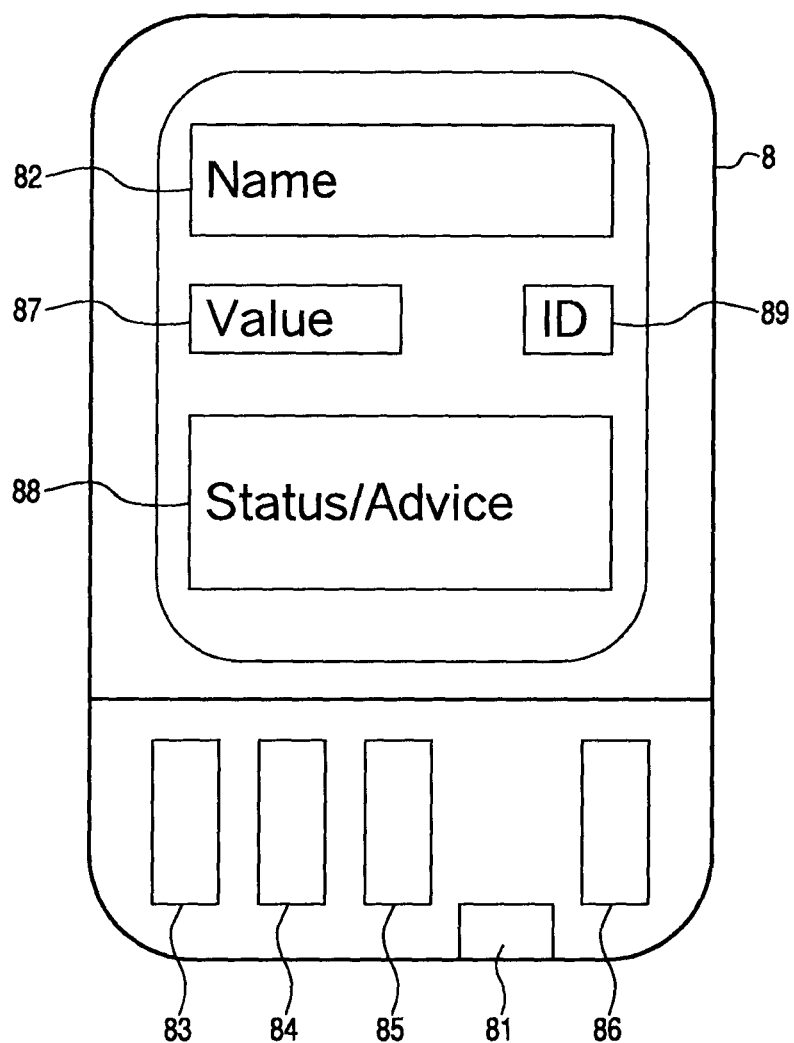
FIG. 13 is a schematic of a first variation of the second exemplary embodiment of the indicator and/or controller shown in FIG. 12.
Figure 14:
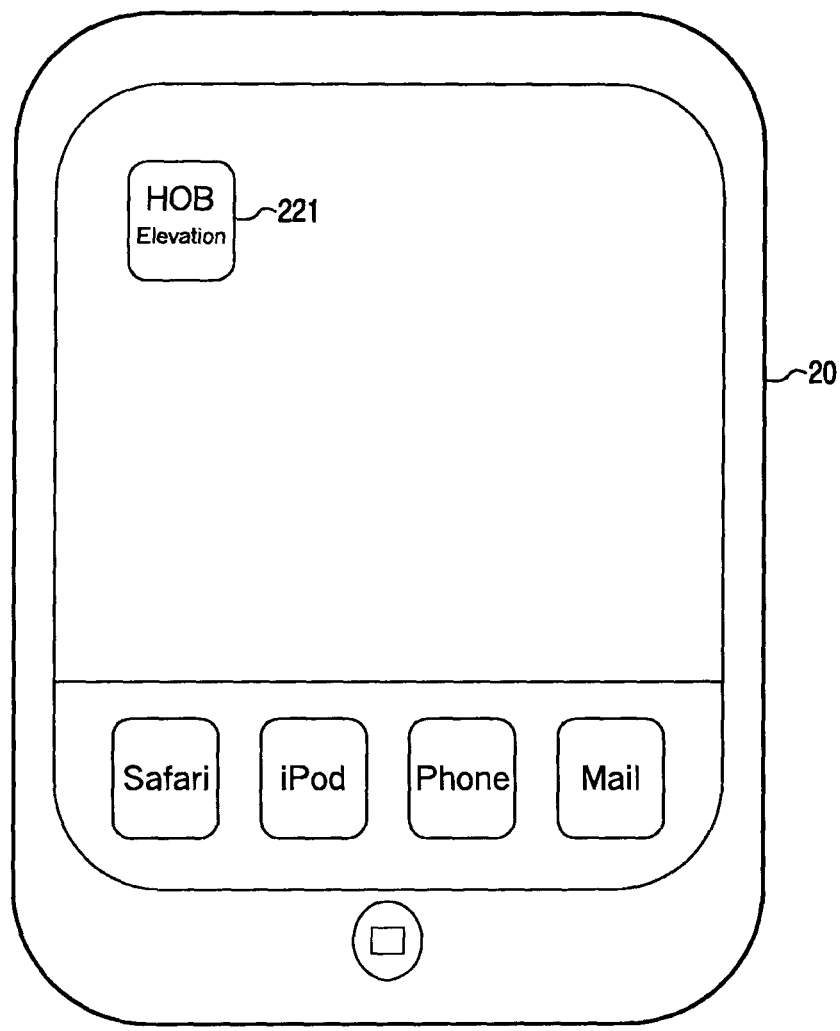
FIG. 14 is a schematic of a main or default screen of a second variation of the second embodiment of the indicator and/or controller of FIG. 12.
Figure 15:
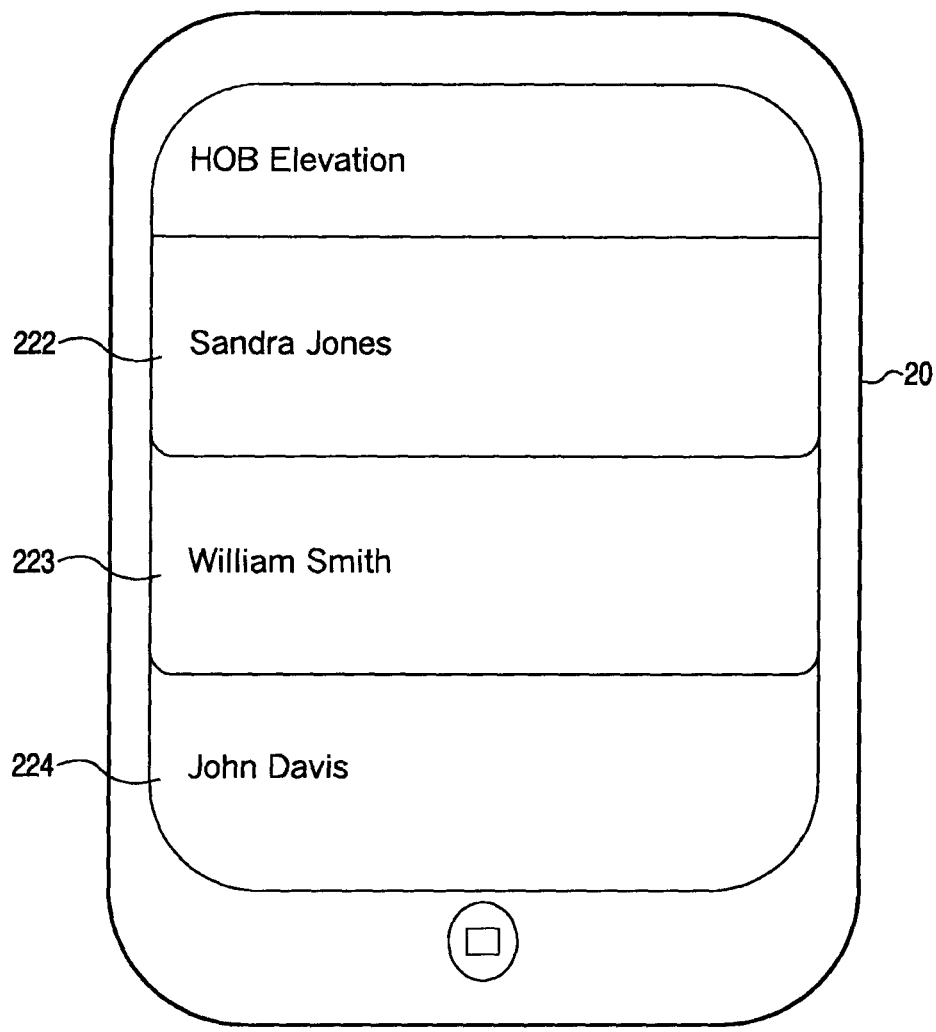
FIG. 15 is a schematic of an exemplary pop-up screen that is displayed once the HOB Elevation is selected for the second variation of the second embodiment of the indicator and/or controller of FIG. 14.
Figure 16:
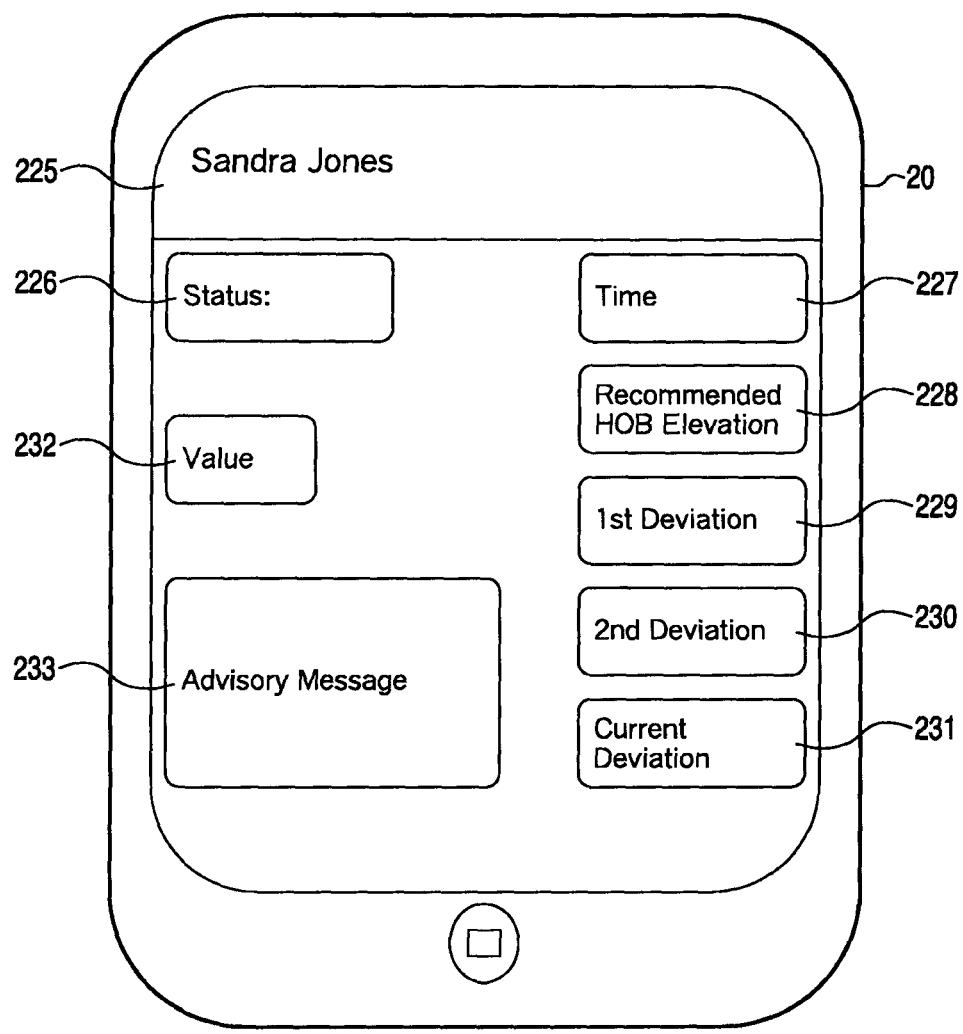
FIG. 16 is a schematic of an exemplary pop-up screen that is displayed once a certain patient is selected for the second variation of the second embodiment of the indicator and/or controller of FIGS. 14 and 15.

As indicated above, FIG. 12 is a schematic of, among other apparatus, an exemplary second embodiment of an indicator/controller. However, the indicator/controller 8, 20 shown in FIG. 12 is merely provided for exemplary purposes, and embodiments are intended to include or cover many variations thereof. In fact, FIG. 13 is directed to a first exemplary variation (indicator/controller 8), and FIGS. 14-16 are directed to a second exemplary variation (indicator/controller 20) of the second embodiment of the indicator/controller of FIG. 12. The two variations of exemplary second embodiment of an indicator/controller 8, 20 shown in FIGS. 13-16 are disclosed below.

a. Dedicated Inputs/Outputs

FIG. 13 is a schematic of the first variation of the second exemplary embodiment of the indicator and/or controller 8 shown in FIG. 12. Exemplary indicators/controllers 8 can include any variety of features, including but not limited to the exemplary features discussed above with regard to the exemplary first embodiment of the indicator/controller shown in FIGS. 7-11, such as input mechanisms and indicators, to facilitate any number of operations including but not limited to those discussed above. Some exemplary features are discussed below in the context of the exemplary indicator/controller 8 shown in FIG. 13 that includes dedicated inputs and outputs (as opposed to the touch screen display of FIGS. 7-11). However, exemplary embodiments are not limited to the features discussed below, and these features are merely provided as examples.

The indicator/controller 8 shown in FIG. 13 includes an input 83 to instruct the indicator/controller 8 to read and/or store patient incline angle data, such as the patient's head-of-bed elevation. In other words, an operator can actuate input 83 so that the indicator/controller 8 is prepared to read and/or store patient incline angle data.

The indicator/controller 8 shown in FIG. 13 can simultaneously store calibration data for several elevation sensors. For example, the indicator/controller 8 would receive data relating to a first patient's head-of-bed elevation. The indicator/controller 8 may then be moved to measure a different patient's head-of-bed elevation. A unique identifying number, e.g., the patient's hospital medical record number (MRN), may be entered into the controller/recorder by the user.

The indicator/controller 8 may keep track of all measurements for a certain patient, including head-of-bed elevation and time of each elevation measurement. The indicator/controller 8 may also keep track of calibration information for a unique patient preventing the need to remove and recalibrate each elevation sensor before another measurement if the controller/recorder had been used on a different patient previously. The above features enable use of a single controller/recorder in a clinical unit (e.g., ICU) thus obviating multiple controllers/recorders.

Embodiments are intended to include indicator(s)/controller(s) 8 that have any other or additional functionalities that may be beneficial or otherwise relevant. For example, the indicator/controller 8 may have a printer function allowing it to print source documents for these readings, and/or may transmit (by wire or wirelessly) this data to a central station such as to archive the above or other measurements.

Additional inputs can be provided to facilitate the above and/or other operations. One or more other inputs can be provided to facilitate the reading and/or storing of other tests. For example, a second input 84 can be operated similarly to input 83 to enable the indicator/controller 8 to read and store elevation over time. A third input 85 can be operated similarly to inputs 83 and 84 to enable the indicator/controller 8 to read and store other data including data not directly or indirectly related to patient incline, such as patient heart rate, respiration, etc. Any number of other or additional inputs can also be provided to handle additional tests.

The exemplary embodiment of FIG. 13 can include a treatment display 88 that displays or otherwise indicates to an operator, such as a medical care provider, recommended care, procedure(s), and/or other information instructing or otherwise helpful to medical care providers. For example, in one exemplary embodiment, upon a change of at least 5 degrees, bed elevation is to be immediately increased until the desired head-of-bed elevation is achieved, e.g., start elevation increase when patient head-of-bed elevation drops below threshold angle of 30 degrees. Thus, this recommended treatment could be displayed in treatment display 88.

In accordance with some exemplary embodiments, one or more components of the sensor 114 and/or indicator/controller 8 may need to be subjected to one or any combination of the following: service, cleaning, repair, replacement, calibration, or other operations. One or any combination of the above operations may need to be performed on a periodic basis, such as after a certain number of uses or after a certain period such as one week.

In this case, the indicator/controller 8 can include an output 81 to apprise an operator that the sensor 114 and/or indicator/ controller 8 is ready for the operation to be performed or that the condition precedent for the operation has passed. The output can be in any form, such as a visual display (including but not limited to a written warning, blinking or lit light, etc.) or sound output (including a buzzer, siren, artificially generated voice, etc.), for example.

In some exemplary embodiments, the indicator/controller 8 handles a single patient at a time. In these embodiments, the indicator/controller 8 can be located proximate the patient, such as at or adjacent to a patient's bed in an ICU, hospital room, etc.

However, the indicator/controller 8 of other exemplary embodiments can be adapted to handle multiple patients simultaneously or in succession, such that information of the multiple patients is stored and operated upon separately. This can be accomplished by entering patient identifying information, such as the patient's name, a code or medical record number representing the patient, etc., via identifying input 89. The identifying input 89 can use any currently known or later developed method or apparatus, such as a keypad, keyboard, voice actuation, etc. In fact, RFID technology can be used to perform the identifying input, wherein the information is transmitted from a patient's badge or wristband to the indicator/controller 8. In these exemplary embodiments, the identifying information is then displayed at identifying display 82.

In the above exemplary embodiment that is capable of handling multiple patients, the treatment display 88 can be used to display any variety of information relating to the patient identified in identifying input 82, such as any relevant updated information including results of the most recent sensor reading, most recent recommended treatment, etc., for example.

As another example, if the patient has already been subjected to incline measurement and a medical care provider returns to the patient after 45 minutes, while the indicator/controller 8 could have been used on other patients in the meantime, the information corresponding to this patient may be accessed and displayed on the treatment display 88. Also, a different display 87 may display the most recent measurement value corresponding to the patient on whom the device is currently used.

b. Touchscreen Display

FIGS. 14-16 are schematics of a second variation of the second embodiment of the indicator and/or controller of FIG. 12, wherein FIG. 14 is a schematic of a main or default screen of the second embodiment. In this exemplary embodiment, software applications for performing operations, such as those discussed above with regard to the indicator/controller 8 of FIG. 13, are incorporated into another type of electronic device 20, i.e., a handheld electronic device, such as an iPad 20, that includes touchscreen displays enabling inputs to be performed via the display. The software can be used on other non-handheld devices or handheld devices, such as iPhone, PDAs, etc.

In this exemplary embodiment, all or some of the inputs discussed with regard to FIG. 13 may be the same, except that touchscreen technology is used rather than hard physical buttons. FIG. 14 shows the startup screen of an iPad 20, where display 221 shows an icon corresponding to an application for the LCD, which can be identified as desired.

For purposes of the exemplary description of FIG. 14, the application is identified as head of bed (HOB) elevation. However, the startup screen can be identified to correspond to any other function/operation performed, including but not limited to other patient elevations and/or non-elevation data, including but not limited to patient heart rate, respiration, etc.

FIG. 15 is a schematic of an exemplary pop-up screen that is displayed once the HOB Elevation is selected for the second variation of the second embodiment of the indicator and/or controller of FIG. 14. In particular, FIG. 15 is a schematic of a pop-up screen that is displayed once the HOB Elevation is selected in the exemplary indicator/controller 20 of FIG. 14. The pop-up screen of FIG. 15 indicates the names or other identifying information of patients (such as all patients) 222, 223, 224 whose conditions are being monitored or who are otherwise under examination and/or treatment.

Selecting the identifying information of any of the patients 222, 223, 224 instructs the indicator/controller 20 to read and display information relevant to the selected patient. FIG. 16 is a schematic of an exemplary pop-up screen that is displayed once a certain patient is selected for the second variation of the second embodiment of the indicator and/or controller of FIGS. 14 and 15. In particular, FIG. 16 is a schematic of an exemplary pop-up screen displaying such information relevant to the selected patient, including updated HOB Elevation data, other test results, current treatment recommendations, etc. Although exemplary embodiments are intended to cover and include any relevant display configuration, the orientation of features of the exemplary embodiment of FIG. 16 is described below.

In the exemplary pop-up screen shown in FIG. 16, patient identifying information, such as the patient's name, can be displayed at patient identifying display 225, which can be disposed at a top section of the pop-up screen. This screen can also include a status display 226 that indicates any information relevant to the patient. For example, the status display 226 may indicate the most current medical or treatment status of the patient. In this example, for a new patient who has not been subjected to any testing, the status display 226 may indicate that the patient is "ready for HOB Elevation monitoring." Alternatively, if the patient is to be subjected to HOB Elevation monitoring, then the message can be, for example, "HOB Elevation monitoring to be performed for" a specified period.

Alternatively, the same or other status information can be indicated on other more specifically tailored displays. For example, a timing display 227 can be used to indicate the time remaining until the HOB Elevation monitoring is no longer needed. Still further, the timing display 227 may provide further indications, such as an indication that HOB Elevation monitoring is no longer needed, such as by another type of visual indication, e.g., flashing. This flashing or other indication, which can take any form, helps warn a medical care provider, such as a nurse, of this situation.

Exemplary embodiments are intended to cover and include any relevant and applicable operation of the displays 228, 229, 230. For example, display 228 can indicate the recommended HOB Elevation, or recommended parameters. Displays 229 and 230 can display relevant historical data, such as first, second, etc., significant deviations from the recommended HOB Elevation or recommended parameters. In other words, display 229 indicates data relating to the first significant deviation from the recommended HOB Elevation or recommended parameters, such as the amount of deviation, length of deviation, etc. Display 230 similarly indicates data relating to the second significant deviation from the recommended HOB Elevation, or recommended parameters. The determination of whether a deviation is significant and thus appropriate for indication at display 229, 230 can depend on the patient conditions, purpose of HOB Elevation monitoring, etc.

Display 231 can be used to indicate other data, such as the current deviation, i.e., deviation from the current recommended HOB Elevation, that may or may not be determined significant. As an alternative, display 231 may be used solely as an input to be actuated. In other words, the display 231 may be used to instruct the indicator/controller 20 to calculate the differential.

The indicator/controller 20 can include any other number of displays. For example, the indicator/controller 20 can include display 232 to indicate other data/values, such as heart rate, respiration, etc.

The exemplary pop-up screen of FIG. 16 can also include a treatment display 233 that provides information similar to the exemplary treatment display 218 of the previously disclosed embodiments. For example, the treatment display 233 may display an advisory message providing relevant information to medical care providers, such as treatment advice.

c. Exemplary Operation

An exemplary application of some of the disclosed methods and apparatus is discussed below. However, the below application is merely intended as an example, and is not intended as an exhaustive disclosure of applications according to all embodiments.

Current national guidelines recommend elevation of the head of the bed of at least 30 degrees (and up to 45 degrees) for mechanically ventilated patients and/or for patients receiving enteral nutrition and at risk of aspiration of gastric contents. Elevating the head of the bed reduces the risk of aspiration such as by virtue of gravity. Elevation of the head allows gravity to reduce the likelihood of gastric contents moving retrograde (backwards) into the esophagus. If gastric contents do not enter the esophagus, then they are less likely to enter the tracheobronchial tree (i.e., aspiration). Other clinical scenarios exist where it is desirable to have the patient lie flat or alternatively be inclined to a certain extent. Unfortunately, the angle of the bed does not necessarily indicate the angle of the patient, because it is common for patients to slide down in the bed, such that only the patient's head is elevated (due to neck flexion).

Thus, in one exemplary embodiment, the sensor 114 shown in FIG. 12 (provided in the shape of a strip) is connected to any of the indicators/controllers 8, 20 disclosed above (including the indicator/controller of FIGS. 7-11). In the context of applying the sensor 114 of FIG. 12 to the patient's anterior, the top (superior) end 116 of the sensor 114 may be located beneath a patient's neck (for example, at the sternal notch), and the bottom (inferior) end 118 of the sensor 114 located over the patient umbilicus (belly button). Any of the above disclosed indicators/controllers, or a separate remote monitor, may assess the two sensor locations, and provide an indication of the relative angle defined between a line connecting these sensor locations with respect to the floor or to the indicator/controller or monitor, which is level and hence represents 0 degrees elevation.

The indicator/controller indicates the elevation of the sternal notch relative to the umbilicus, e.g., 0 degrees, 20 degrees, 30 degrees, 35 degrees. In many cases, it may be desirable to maintain the angle at least 30 or 45 degrees, as in enteral nutrition, to reduce or minimize the risk of aspiration. Other uses include cases where it is desirable to elevate the head of the bed, such as with some neurosurgical patients experiencing increased intracranial pressure, making it desirable to have the HOB elevated at least 30 degrees. In this application, the sensor may be positioned with the superior end by the head and the inferior end by the sternum or umbilicus. Another exemplary embodiment uses this technology to ensure that the patient's head is not elevated, e.g., in cases of patients at risk of lumbar leakage of cerebrospinal fluid.

The above functions/operations are not intended as limiting, and are merely provided as examples of potentially beneficial functions/operations that can be provided in conjunction with the disclosed methods and apparatus.

d. Alternative or Additional Functionalities

Figure 17:
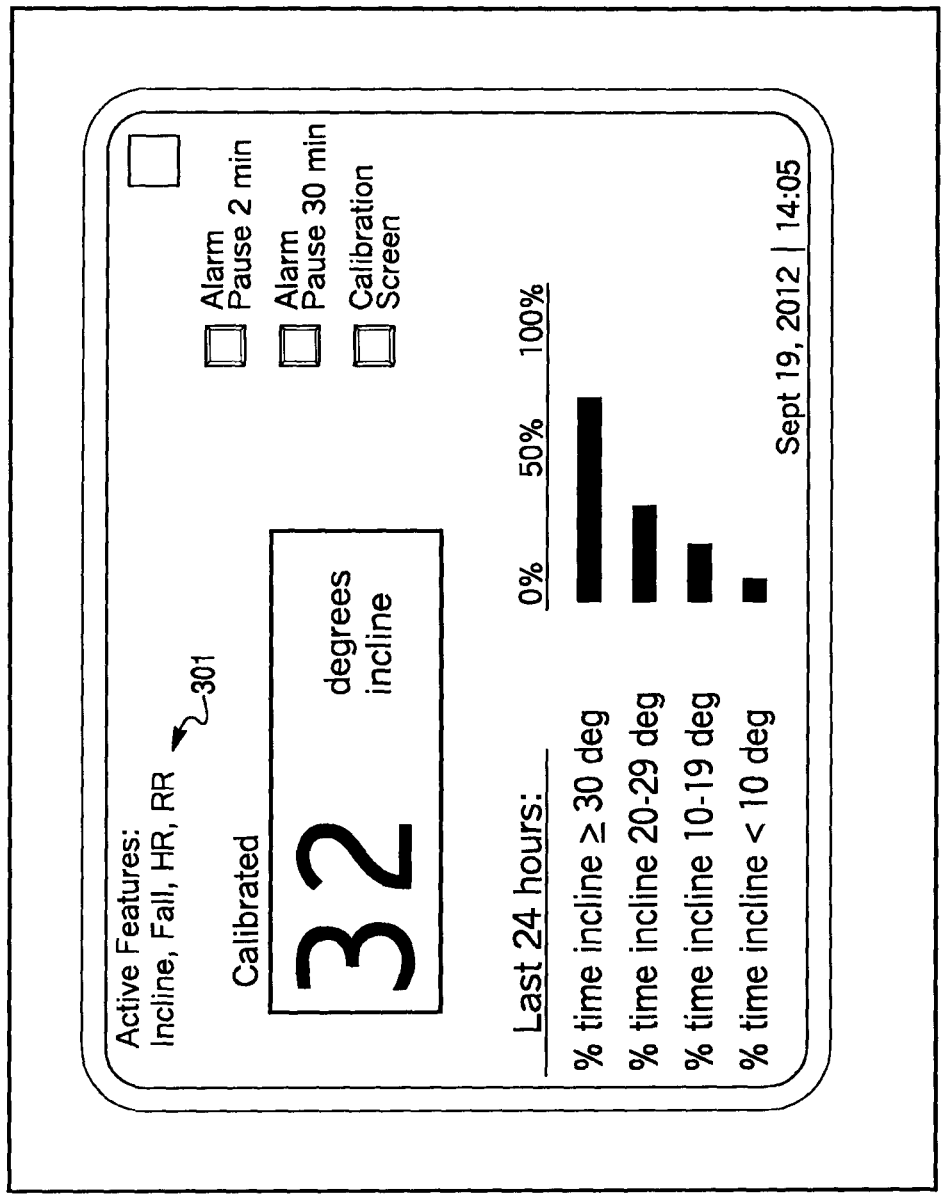
FIG. 17 is a schematic of a main or default screen as an alternative to the screen shown in FIG. 7

Other embodiments include or otherwise cover alternative indicator/controllers that provide alternative or additional functionalities. For example, FIG. 17 is a schematic of a main or default screen as an alternative to the screen shown in FIG. 7. The screen shown in FIG. 17 includes active features region 301 that, in addition to incline and fall monitoring, provides access to or otherwise enables heart rate and respiratory rate monitoring.

Combining the monitoring of numerous conditions, including but not limited to incline, fall prevention, heart rate, respiratory rate, respiratory depth, gastrointestinal motility, sleep analysis, seizure detection, etc. is beneficial for numerous reasons. For example, this configuration enables a single device to monitor multiple conditions and thereby reduces equipment costs because a separate apparatus does not need to be dedicated to monitoring each condition. In addition, users, such as medical care providers, do not need to be trained for multiple devices, which reduces training and workload, while at the same time reduces user errors by simplifying usage, Embodiments are intended to include or otherwise cover any methods and apparatus for implementing the above, especially configurations that facilitate and simplify use. As one example, a dashboard or other display configuration can be provided at a certain location of the user interface, such as at the top or bottom. The dashboard can include icons showing or otherwise indicating which patient conditions or monitoring functionalities are active at any time.

Combining the monitoring of numerous conditions as disclosed herein is also beneficial because it enables or facilitates monitoring or increased monitoring of patients and patient conditions that are not typically monitored or closely monitored in the related art. For example, in the related art, hospital patients who are not in the ICU, such as patients "on the floor," typically only have their conditions, such as vital signs, monitored once every four or eight hours. This infrequent monitoring is based on a variety of factors, such as workload constraints of health care providers, e.g., a single health care (such as a nurse) being responsible for a relatively large number of patients (such as 20 patients). The related art technique is also disadvantageous because it typically involves waking the patient in cases where the patient is asleep when the vital signs need to be monitored.

However, the above apparatus enables various patient conditions, including vital signs, of patients on the floor to be monitored more frequently, such as every ten minutes or even continuously, without incurring the above workload constraints, or disturbing/waking the patient in cases where the patient is asleep. If any of the above patient conditions or vital signs warrants intervention, then closer monitoring will enable faster intervention by the medial care provider. In order to facilitate faster intervention, an appropriate communication or alarm can be provided to the medical care providers if any of the monitored patient conditions warrants such intervention.

Embodiments are also intended to use and combine the data gathered from multiple different patient conditions for any beneficial use. As one example, if the monitored patient conditions indicate that the patient is sleeping or otherwise unconscious, then the fall prevention monitoring can be performed less frequently, or even discontinued, until the monitored conditions indicate that the patient is awake, which may be beneficial for various reasons, such as to increase battery life. Sampling rates of other conditions can similarly be modified, such as increased or decreased, depending on the various monitored conditions, e.g., heart rate, respiratory rate, respiratory depth, etc.

In the embodiment shown in FIG. 17, the incline monitoring is selected, and thus the patient's incline is displayed. In some of these embodiments, selecting any of the other types of monitoring results in the data of that type of monitoring being displayed in place of the incline data shown in FIG. 17.

Figure 18:
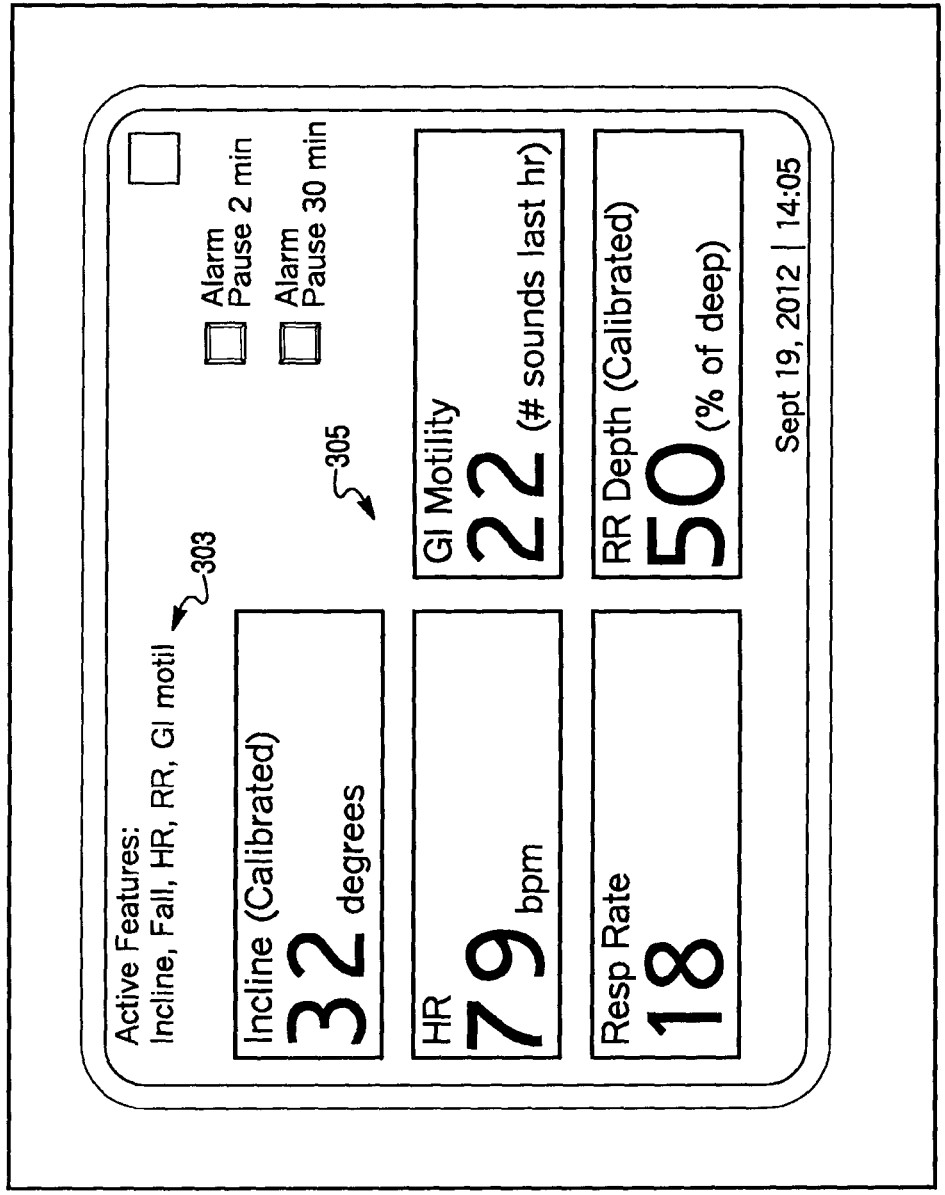
FIG. 18 is a schematic of a main or default screen as another alternative to the screen shown in FIGS. 7 and 17.

FIG. 18 is a schematic of a main or default screen of another alternative to the screen shown in FIGS. 7 and 17. The screen shown in FIG. 18 includes an alternative active features region 303 that, in addition to the incline, fall, heart rate, and respiratory rate monitoring, also provides access to or otherwise enables gastrointestinal motility monitoring.

In the embodiment of FIG. 18, the incline monitoring is displayed in the same location as with the embodiments of FIGS. 7 and 17. However, a separate monitoring region 305 is provided that displays data for the other types of monitoring. As an alternative to the embodiment shown in FIG. 18, selecting any of the types of monitoring results in the data of that type of monitoring being displayed in place of the incline data shown in the figure.

Figure 19:
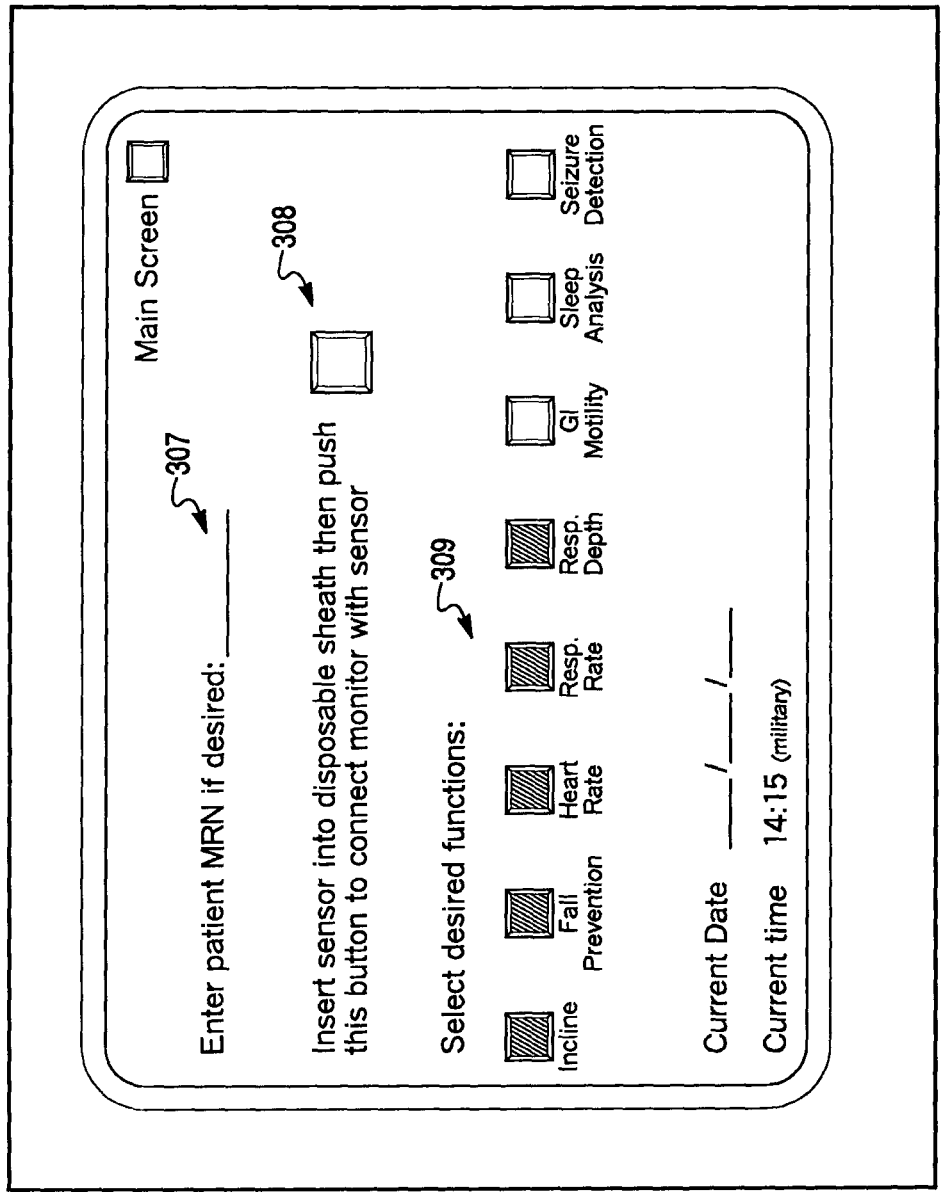
FIG. 19 is a schematic of a monitor functions screen as an additional or alternative screen to the screens of FIGS. 7, 17 and 18.

FIG. 19 is a schematic of a monitor functions screen as an additional or alternative screen to the screens of FIGS. 7, 17 and 18. For example, the monitor functions screen can be selected for display from the main or default screen.

The monitor functions screen can include a patient identification region 307 that enables display of a certain patient's monitored data. This function may be beneficial in a variety of situations, such as where a certain indicator/controller is being used to monitor data of multiple patients. In some embodiments, this region 307 permits the user to enter a patient's medical records number (MRN).

The monitor functions screen of FIG. 19 also includes a connect monitor with sensor region 308 that enables a data connection between the monitor and the sensor. In the embodiment of FIG. 19, selecting this option enables a process to establish a data connection between the monitor and the sensor. Thus, selecting this option establishes a data connection between the sensor and monitor, further enabling the monitor to receive, process, and display the data.

The monitor functions screen of FIG. 19 also includes a monitor functions region 309 that enables selection of one or more types of monitoring. In the embodiment of FIG. 19, in addition to the types of monitoring disclosed with regard to FIG. 18, the monitoring functions region 309 also enables monitoring of respiratory depth, sleep analysis, and seizure detection. Thus, selection of any or all of these types of monitoring enables access to data relating to the corresponding type of monitoring.

Figure 20:
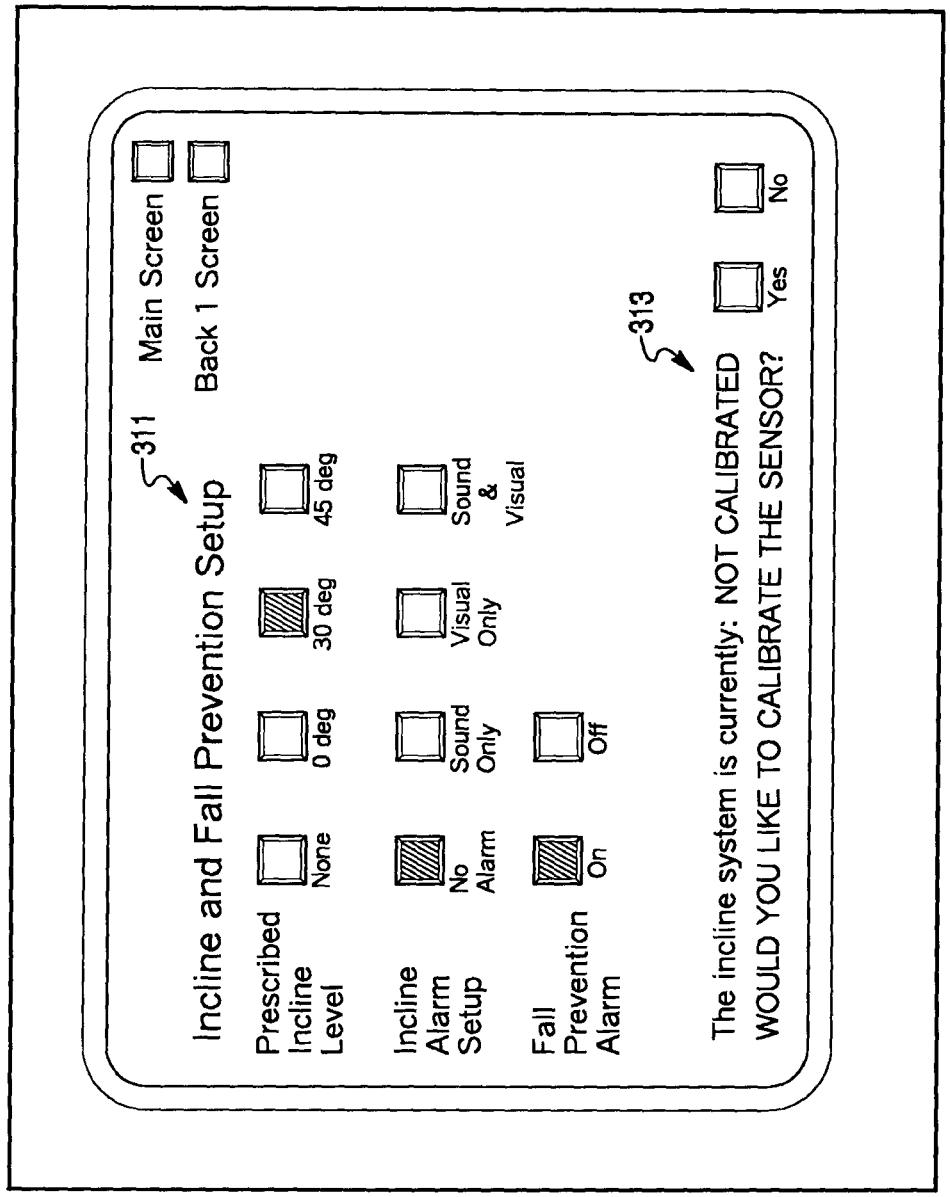
FIG. 20 is a schematic of an incline and fall prevention setup screen as an alternative to the screen of FIG. 8.

FIG. 20 is a schematic of an incline and fall prevention setup screen as an alternative to the screen of FIG. 8. The screen includes an identification region 311 that identifies the type of monitoring that is the subject of the setup procedures, which in the case of FIG. 20 is incline and fall prevention. In the context of this type of monitoring, the screen of FIG. 20 provides the same types of setup options as the screen of FIG. 8, i.e., prescribed incline level, incline alarm setup, and fall prevention alarm.

However, the screen of FIG. 20 differs from the screen of FIG. 8 by its inclusion of a calibration region 313, which indicates whether the particular type of selected monitoring is currently calibrated, and enables the user to select whether or not to initiate calibration operations. For example, the screen of FIG. 20 provides yes and no actuators, and thus the user's selection of the yes actuator initiates calibration operations.

Figure 21:
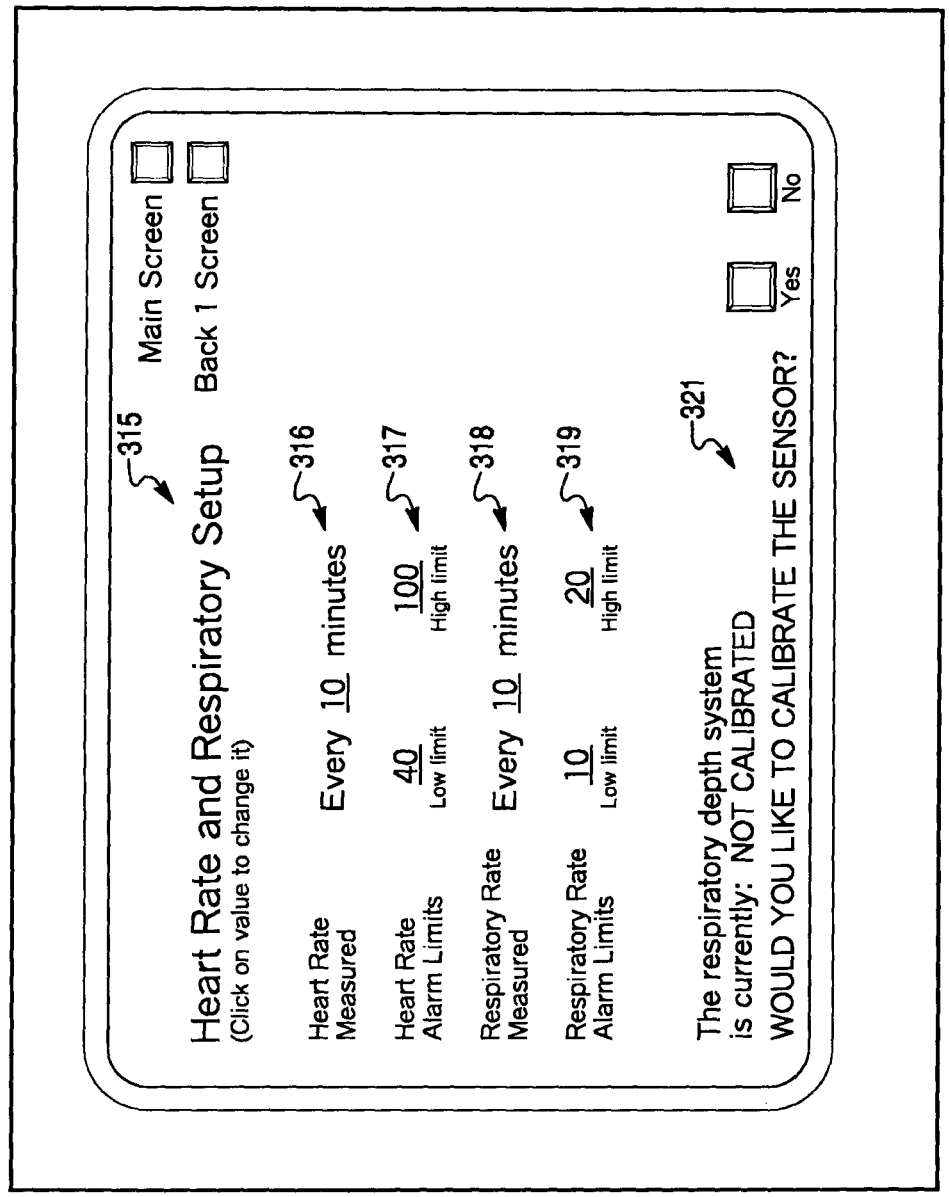
FIG. 21 is a schematic of an exemplary heart rate and respiratory rate setup screen.

FIG. 21 is a schematic of an exemplary heart rate and respiratory rate setup screen. The screen of FIG. 21 can be displayed pursuant to any sequence of operation, such as following selection of the heart rate and respiratory types of monitoring shown in FIG. 19.

The exemplary screen shown in FIG. 21 includes heart rate measured region 316, which enables setting the frequency for how often the heart rate is measured. In the screen shown in FIG. 21, the frequency is set for 10 minutes. Thus, the heart rate will be measured at each set interval, i.e. every 10 minutes. In this exemplary embodiment, the heart rate may be measured for 10 seconds, which would be sufficient to capture an effective measure of the heart rate. In another exemplary embodiment, the sensor may measure heart rate and respiratory rate for 30 seconds, which would be sufficient to capture an effective measure of the heart rate and the respiratory rate. In this exemplary embodiment, the sensor would then be turned off until the next frequency interval in order to conserve battery life. Embodiments are intended to provide any type of beneficial or otherwise useful frequency for measuring the heart rate.

The exemplary screen shown in FIG. 21 also includes respiratory rate measured region 318, which enables setting the frequency for how often the respiratory rate is measured. In the screen shown in FIG. 21, the frequency is set for 10 minutes. Thus, the respiratory rate will be measured at each set interval, i.e. every 10 minutes. Embodiments are intended to provide any type of beneficial or otherwise useful frequency for measuring the respiratory rate.

The exemplary screen shown in FIG. 21 includes a heart rate alarm limits region 317, which enables the user to set lower and high/upper limits of the heart rate. In the screen shown in FIG. 21, the lower limit is set at 40 beats, and the high/upper limit is set at 100 beats. Thus, deviation of the monitored heart rate below or above these limits, i.e., less than 40 beats or greater than 100 beats per minute, causes the indicator/controller to register an alarm condition. Embodiments are intended to provide any type of operations upon registering an alarm condition that may be beneficial or otherwise useful. For example, in some embodiments, registering an alarm condition results in the indicator/controller communicating the condition to medical care providers, such as via an audible or visual alarm.

The exemplary screen shown in FIG. 21 also includes a respiratory rate alarm limits region 319, which enables the user to set lower and high/upper limits of the respiratory rate. In the screen shown in FIG. 21, the lower limit is set at 10 breaths, and the high/upper limit is set at 20 breaths per minute. Thus, deviation of the monitored respiratory rate below of above these limits, i.e., less than 10 breaths or greater than 20 breaths per minute, causes the indicator/controller to register an alarm condition. Embodiments are intended to provide any type of operations upon registering an alarm condition that may be beneficial or otherwise useful. For example, in some embodiments, registering an alarm condition results in the indicator/controller communicating the condition to medical care providers, such as via an audible or visual alarm.

The screen of FIG. 21 also includes a calibration region 321, which indicates whether the particular type of selected monitoring is currently calibrated, and enables the user to select whether or not to initiate calibration operations. For example, the screen of FIG. 21 provides yes and no actuators, and thus the user's selection of the yes actuator initiates calibration operations.

Figure 22:
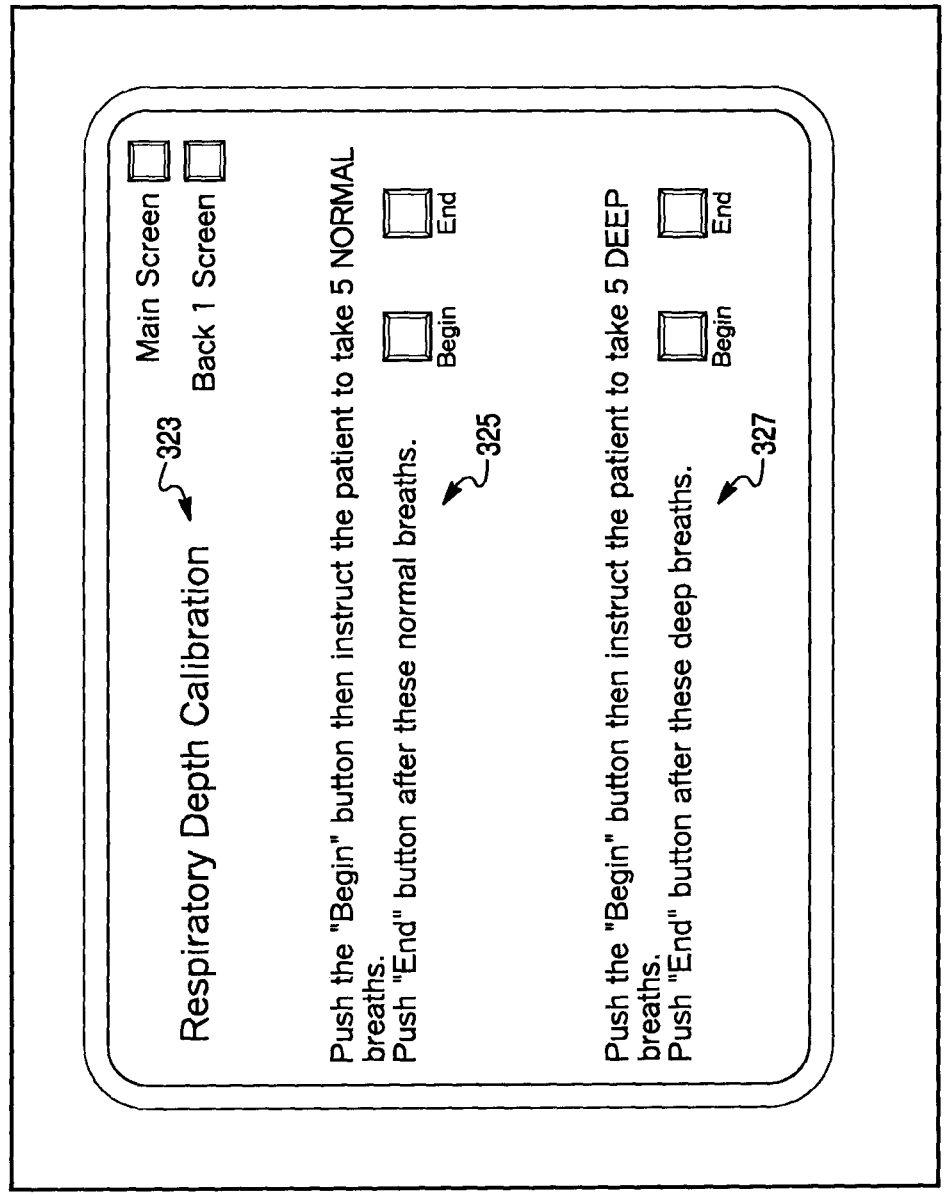
FIG. 22 is a schematic of an exemplary respiratory depth calibration screen.

FIG. 22 is a schematic of an exemplary respiratory depth calibration screen. The screen of FIG. 22 can be accessed pursuant to any sequence of operations, such as subsequent to selection of the respiratory monitoring of FIG. 19, and upon actuation of the yes actuator of FIG. 21.

The screen of FIG. 22 includes a screen indication region 323 that indicates the type of monitoring subject to calibration, which in the case of FIG. 22 is respiratory depth. A 5 normal breaths region 325 enables calibration based on a patient taking normal breaths. A begin actuator in this region is activated as the patient begins taking 5 normal breaths, and an end actuator in this region activated after the patient has taken the 5 normal breaths.

The screen of FIG. 22 also includes a 5 deep breaths region 327 that enables calibration based on a patient taking 5 deep breaths. A begin actuator in this region is activated as the patient begins taking 5 deep breaths, and an end actuator in this region activated after the patient has taken the 5 deep breaths.

B. Exemplary Equipment Packaging

1. Kit

Exemplary embodiments are intended to cover any beneficial grouping, packaging or presentation of any one or any combination of any of the apparatus disclosed above.

In one exemplary embodiment, the kit includes all elements of the sensor and/or sensor system. For example, the kit includes at least one incline sensor with mechanism for attachment to the patient (either directly or indirectly), the indicator/controller, and any other apparatus required or otherwise helpful to facilitate communication there between, such as wires.

However, other embodiments only include subset(s) of the above apparatus and/or other equipment. For example, some embodiments only include the sensor(s) and/or attachment mechanism. In some embodiments that include a reusable sensor, the kit may only include one (or a small number of) sensors, and multiple (such as a relatively large number of) attachment mechanisms. In other words, these kits enable one (or a small number of) sensors to be reused via a larger number of attachment mechanisms; wherein the attachment mechanisms are disposed of following each use, while the sensor(s) are reused.

Alternatively, in other embodiments that include disposable sensors, i.e., sensors intended for disposal following one or a small number of uses, the kit may include a larger number of sensors and attachment mechanisms. In some of these embodiments, the sensor(s) are attached, or otherwise operatively connected to, the attachment mechanism(s) in the kit, and can thereby be used, i.e., attached to the patient, upon removal from the kit with reduced effort.

The above exemplary embodiments are merely provided for illustrative purposes, and other exemplary embodiments are intended to cover any beneficial grouping, packaging or presentation of the disclosed apparatus and/or pharmaceuticals.

2. Processor

Some exemplary embodiments are intended to cover supply and packaging of only one of the elements disclosed above or various sub-combinations of the disclosed elements. For example, some exemplary embodiments are solely directed to a processor for guiding medical care of a patient, such as based on detected HOB Elevation. Exemplary embodiments are intended to cover all processors capable of performing all of the various heretofore-disclosed determinations, calculations, etc., for the above purposes, such as determining HOB Elevation.

3. Computer Program

Some exemplary embodiments are intended to cover supply and packaging of only one of the elements disclosed above or various sub-combinations of the disclosed elements. In addition to the exemplary processors disclosed above, some exemplary embodiments are solely directed to software or computer programs for guiding medical care of a patient, such as based on HOB Elevation. In fact, some exemplary embodiments are directed solely to the software or computer programs that perform various determinations, calculations, etc., for the purpose of guiding medical care, such as based on HOB Elevation.

Exemplary embodiments are intended to cover all software or computer programs capable of performing the various heretofore-disclosed determinations, calculations, etc., for the purpose of determining HOB Elevation. For example, exemplary embodiments are intended to cover all software or computer programs capable of enabling the processors disclosed above to implement the disclosed processes. In other words, exemplary embodiments are intended to cover all systems and processes that configure a document operating system to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed above.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, Cobol, C, C++, Java, Pascal, or scripting languages such as JavaScript, Python, Ruby, PHP, Perl or other sufficient programming languages.

What is claimed is:

1. An apparatus for monitoring patient orientation, comprising:

a reusable sensor configured to detect inclination angles of an anterior region of the patient; and an elongated disposable attachment device having a first end and a second end, a distance between the first end and the second end defining a length of the elongated disposable attachment device, the length of the elongated disposable attachment device being greater than a maximum width of the elongated disposable attachment device that is perpendicular to a first direction between the first end and the second end of the elongated disposable attachment device, the elongated disposable attachment device configured for removable attachment to both the sensor and the patient's anterior region such that the first direction of the attachment device extends along a longitudinal axis of a sternum of the patient, the attachment device including:
- a sensor attachment portion configured for removable attachment to the sensor such that the sensor is prevented from direct contact with the patient,
- a patient attachment portion configured for removable attachment to the patient's anterior region, and
- a first connector attached to the sensor attachment portion and a second connector attached to the patient attachment portion, the first connector and the second connector being configured to detachably mate to each other.

2. The apparatus for monitoring patient orientation according to claim 1, wherein the sensor attachment portion is elongated and opposite ends of the elongated sensor attachment portion comprise the first and second ends of the elongated disposable attachment device, respectively, and the patient attachment portion includes two separate, physically distinct and non-integral attachment portions that are each individually removably attachable to locations adjacent the opposite ends of the elongated sensor attachment portion.

3. The apparatus for monitoring patient orientation according to claim 2, wherein at least a part of the sensor attachment portion is hollow and configured for disposing the sensor therein.

4. The apparatus for monitoring patient orientation according to claim 2, wherein the sensor attachment portion defines a sealable pouch that is configured for disposing the sensor therein.

5. The apparatus for monitoring patient orientation according to claim 4, wherein the pouch is defined at an upper surface of the sensor attachment portion.

6. The apparatus for monitoring patient orientation according to claim 1, wherein the sensor is an accelerometer.

7. The apparatus for monitoring patient orientation according to claim 1, further including a sensor sheath that houses the sensor and that is insertable into the sensor attachment portion.

8. The apparatus for monitoring patient orientation according to claim 7, further comprising a controller that is spaced apart from and physically unconnected with the sensor, and a transmitter that wirelessly transmits signals between the sensor and the controller, the sensor sheath housing the transmitter.

9. The apparatus for monitoring patient orientation according to claim 8, wherein the controller includes an indicator that enables viewing of the incline angles detected by the sensor.

10. The apparatus for monitoring patient orientation according to claim 8, wherein the controller controls the sensor to vary the frequency of incline measurements.

11. The apparatus for monitoring patient orientation according to claim 8, wherein the controller provides an alarm indication if the sensor detects certain incline angles.

12. The apparatus for monitoring patient orientation according to claim 11, wherein the controller provides an alarm indication if the sensor detects that the patient's incline angle falls below a certain angle.

13. The apparatus for monitoring patient orientation according to claim 12, wherein the controller provides an alarm indication if the sensor detects that the patient's incline angle falls below 30 degrees.

14. The apparatus for monitoring patient orientation according to claim 11, wherein the controller provides an alarm indication if the sensor detects that the patient's incline angle indicates that the patient is attempting to stand.

15. The apparatus for monitoring patient orientation according to claim 11, wherein the controller provides an alarm indication if the sensor detects that the patient's incline angle exceeds a certain angle.

16. The apparatus for monitoring patient orientation according to claim 8, wherein the controller is configured to monitor the patient conditions, including at least one of heart rate, respiratory rate, respiratory depth, GI motility, sleep analysis, and seizure detection.

17. The apparatus for monitoring patient orientation according to claim 16, wherein the controller is configured to control an aspect of sensing of at least one of the monitored conditions based on at least one of another of the monitored conditions.

18. The apparatus for monitoring patient orientation according to claim 17, wherein the controller is configured to affect the frequency of monitoring of patient incline based on data of at least one of the other monitored conditions.

19. The apparatus for monitoring patient orientation according to claim 18, wherein the controller is configured to reduce the frequency of monitoring of patient incline if data of at least one heart rate, respiratory rate, and respiratory depth indicates that the patient is asleep.

20. The apparatus for monitoring patient orientation according to claim 1, wherein the sensor attachment portion comprises a pouch configured to fully encapsulate the sensor.

21. An apparatus for monitoring patient orientation, comprising:
- a reusable sensor configured to detect inclination angles of an anterior region of the patient; and
- an elongated disposable attachment device having a first end and a second end, a distance between the first end and the second end defining a length of the elongated disposable attachment device, the length of the elongated disposable attachment device being greater than a maximum width of the elongated disposable attachment device that is perpendicular to a first direction between the first end and the second end of the elongated disposable attachment device, the elongated disposable attachment device configured for removable attachment to both the sensor and the patient's anterior region such that the first direction of the attachment device extends along a longitudinal axis of a sternum of the patient, the attachment device including:
  - a sensor attachment portion configured for removable attachment to the sensor such that the sensor is prevented from direct contact with the patient, and
  - a patient attachment portion configured for removable attachment to the patient's anterior region,
- wherein the sensor at attachment portion is configured to connect to the reusable sensor such that the reusable sensor has an alignment having a fixed relationship to the first direction, and,
- wherein the patient attachment portion is configured for removable attachment to skin of the patient at the sternum of the patient.

22. The apparatus for monitoring patient orientation according to claim 21, wherein the maximum width of the elongated disposable attachment device is less than a width of the sternum of the patent that is perpendicular to the longitudinal axis of the sternum of the patient.

23. The apparatus for monitoring patient orientation according to claim 22, wherein the length of the elongated disposable attachment device is greater than at least half of a length of the sternum along the longitudinal axis of the sternum.

24. The apparatus for monitoring patient orientation according to claim 21, wherein the sensor attachment portion comprises a sealable encasement that is configured to dispose the sensor therein.

25. The apparatus for monitoring patient orientation according to claim 21,
wherein the sensor attachment portion defines a sensor housing that is configured to dispose the sensor therein to fully encapsulate the sensor,
wherein a first end of the sensor housing comprises a pivoting arm to open the sensor housing to facilitate insertion of the sensor into the sensor housing, and
wherein the battery receiver is disposed within the sensor housing at a second end of the sensor housing, opposite the first end of the sensor housing.

26. An apparatus for monitoring patient orientation, comprising:
a reusable sensor configured to detect inclination angles of an anterior region of the patient; and
an elongated disposable attachment device having a first end and a second end, a distance between the first end and the second end defining a length of the elongated disposable attachment device, the length of the elongated disposable attachment device being greater than a maximum width of the elongated disposable attachment device that is perpendicular to a first direction between the first end and the second end of the elongated disposable attachment device, the elongated disposable attachment device configured for removable attachment to both the sensor and the patient's anterior region such that the first direction of the attachment device extends along a longitudinal axis of a sternum of the patient, the attachment device including:
a sensor attachment portion configured for removable attachment to the sensor such that the sensor is prevented from direct contact with the patient, and
a patient attachment portion configured for removable attachment to the patient's anterior region,
wherein the sensor attachment portion defines a pouch that is configured to dispose the sensor therein to fully encapsulate the sensor, the pouch comprising a sealable opening to facilitate insertion of the sensor into the pouch.

27. The apparatus for monitoring patient orientation according to claim 26, wherein a first end of the pouch comprises a pivoting arm to open the pouch to facilitate insertion of the sensor into the pouch.

28. The apparatus for monitoring patient orientation according to claim 26, wherein the sensor attachment portion of the elongated disposable attachment device comprises a battery receiver configured to house a battery to provide power to the reusable sensor.

29. The apparatus for monitoring patient orientation according to claim 28,
wherein the sensor attachment portion comprises a sensor housing that is configured to dispose the sensor therein to encapsulate the sensor,
wherein the battery receiver is disposed within the sensor housing at a second end of the sensor housing, opposite the first end of the sensor housing.

30. The apparatus for monitoring patient orientation according to claim 29,
wherein the battery receiver comprises a first connector and the reusable sensor comprises a second connector,
wherein the first connector and the second connector are configured to mate with each other to supply power to the reusable sensor.

* * * * *